(12) United States Patent
Kestesz et al.

(10) Patent No.: US 7,998,969 B2
(45) Date of Patent: Aug. 16, 2011

(54) NON-NUCLEOSIDE REVERSE TRANSCRIPTASE INHIBITORS

(75) Inventors: Denis John Kestesz, Mountain View, CA (US); Christine E. Brotherton-Pleiss, Sunnyvale, CA (US); Minmin Yang, Shanghai (CN)

(73) Assignee: Roche Palo Alto LLC, South San Francisco, CA (US)

( * ) Notice: Subject to any disclaimer, the term of this patent is extended or adjusted under 35 U.S.C. 154(b) by 914 days.

(21) Appl. No.: 12/001,947

(22) Filed: Dec. 13, 2007

(65) Prior Publication Data
US 2008/0146595 A1 Jun. 19, 2008

Related U.S. Application Data

(60) Provisional application No. 60/874,673, filed on Dec. 13, 2006.

(51) Int. Cl.
*C07D 401/14* (2006.01)
*C07D 403/12* (2006.01)
*A61K 31/502* (2006.01)

(52) U.S. Cl. ........ 514/272; 514/275; 544/296; 544/321; 544/323; 544/324

(58) Field of Classification Search .................. 544/296, 544/321, 323, 324; 514/272, 275
See application file for complete search history.

(56) References Cited

FOREIGN PATENT DOCUMENTS

| WO | WO 00/03998 A1 | 1/2000 |
|---|---|---|
| WO | WO 03/016306 A1 | 2/2003 |
| WO | WO 2006/035067 A2 | 4/2006 |
| WO | WO 2006/035067 A3 | 4/2006 |
| WO | WO 2006/035068 A2 | 4/2006 |
| WO | WO 2006/035068 A3 | 4/2006 |
| WO | WO 2006/035369 A2 | 4/2006 |
| WO | WO 2006/035369 A3 | 4/2006 |
| WO | WO 2006/045828 A1 | 5/2006 |
| WO | WO 2006/087387 A1 | 8/2006 |
| WO | WO 2006/094930 A1 | 9/2006 |

OTHER PUBLICATIONS

Miles, Medline Abstract (Community Pract, vol. 78, Issue 8, pp. 292-294) Aug. 2005.* van Heeswijk et al., PubMed Abstract (Antivir Ther. 6(4):201-29) Dec. 2001.*

Marcus et al., PubMed Abstract (Intervirology 45(4-6):260-6) 2002.*

Brugel, T.A., et. al. "Development of N-2,4-pyrimidine-N-phenyl-N'-phenyl ureas as inhibitors of tumor necrosis factor alpha (TNF-α) synthesis. Part 1," *Bioorganic & Medicinal Chemistry Letters* (2006) vol. 16, pp. 3510-3513.

Das, K., et. al. "Roles of Conformational and Positional Adaptability in Structure-Based Design of TMC125-R165335 (Etravirine) and Related Non-nucleoside reverse Transcriptase Inhibitors that are Highly Potent and Effective Against Wild-type and Drug—Resistant HIV-1 Variants," *J. Med. Chem.* (2004) vol. 47, pp. 2550-2560.

Guillemont, J., et. al. "Synthesis of Novel Diarylpyrimidine Analogues and Their Antiviral Activity against Human Immunodeficiency Virus Type 1," *J. Med. Chem.* (2005) vol. 48, pp. 2072-2079.

Janssen, P.A., et. al. "In Search of a Novel Anti-HIV Drug: Multidisciplinary Coordination in the Discovery of 4-[[4-[[4-[(1E)-2,6-dimethylphenyl]amino]-2-pyrimidinyl]amino]benzonitrile (R278474, Rilpivirine)," *J. Med. Chem.* (2005) vol. 48, pp. 1901-1909.

* cited by examiner

*Primary Examiner* — Deepak Rao
(74) *Attorney, Agent, or Firm* — Brian L. Buckwalter

(57) ABSTRACT

The present invention provides for compounds useful for treating an HIV infection, or preventing an HIV infection, or treating AIDS or ARC. The compounds of the invention are of formula I wherein $R^1$, $R^2$, $R^3$, $R^4$, $R^{5a}$, $R^{5b}$, $R^{6a}$, $R^{6b}$ and X are as herein defined. Also disclosed in the present invention are methods of treating an HIV infection with compounds defined herein and pharmaceutical compositions containing said compounds.

(I)

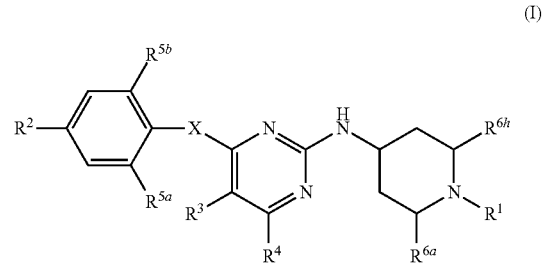

18 Claims, No Drawings

SEQUENCE LISTING

<160> NUMBER OF SEQ ID NOS: 2

<210> SEQ ID NO 1
<211> LENGTH: 18
<212> TYPE: DNA
<213> ORGANISM: Artificial sequence
<220> FEATURE:
<223> OTHER INFORMATION: sequence is synthesized

<400> SEQUENCE: 1
gtccctgttc gggcgcca                                              18

<210> SEQ ID NO 2
<211> LENGTH: 47
<212> TYPE: RNA
<213> ORGANISM: Artificial sequence
<220> FEATURE:
<223> OTHER INFORMATION: sequence is synthesized

<400> SEQUENCE: 2
gggucucucu gguuagacca cucuagcagu ggcgcccgaa  cagggac              47

NON-NUCLEOSIDE REVERSE TRANSCRIPTASE INHIBITORS

CROSS REFERENCE TO PRIOR APPLICATIONS

This application is claims benefit of U.S. Provisional Application No. 60/874,673, filed Dec. 13, 2006, which is hereby incorporated by reference in its entirety.

FIELD OF THE INVENTION

The invention relates to the field of antiviral therapy and, in particular, to non-nucleoside compounds that inhibit HIV reverse transcriptase and are useful for treating Human Immunodeficiency Virus (HIV) mediated diseases. The invention provides novel pyrimidine compounds according to formula I, for treatment or prophylaxis of HIV mediated diseases, AIDS or ARC, employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the CD4+ T-cell, with attendant susceptibility to opportunistic infections. HIV infection is also associated with a precursor AIDS-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. Montaner et al., *Antiretroviral therapy: 'the state of the art' Biomed & Pharmacother.* 1999 53:63-72; R. W. Shafer and D. A. Vuitton, *Highly active retroviral therapy (HAART) for the treatment of infection with human immunodeficiency virus type, Biomed. & Pharmacother.* 1999 53:73-86; E. De Clercq, *New Developments in Anti-HIV Chemotherap. Curr. Med. Chem.* 2001 8:1543-1572). Two general classes of RTI inhibitors have been identified: nucleoside reverse transcriptase inhibitors (NRTI) and non-nucleoside reverse transcriptase inhibitors. Currently the CCR5 co-receptor has emerged as a potential target for anti-HIV chemotherapy (D. Chantry, *Expert Opin. Emerg. Drugs* 2004 9(1):1-7; C. G. Barber, *Curr. Opin. Invest. Drugs* 2004 5(8):851-861; D. Schols, *Curr. Topics Med. Chem.* 2004 4(9):883-893; N. A. Meanwell and J. F. Kadow, *Curr. Opin. Drug Discov. Dev.* 2003 6(4):451-461).

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity (R. W. Buckheit, Jr., *Non-nucleoside reverse transcriptase inhibitors: perspectives for novel therapeutic compounds and strategies for treatment of HIV infection, Expert Opin. Investig. Drugs* 2001 10(8)1423-1442; E. De Clercq, *The role of non-nucleoside reverse transcriptase inhibitors (NNRTIs) in the therapy of HIV infection, Antiviral Res.* 1998 38:153-179; E. De Clercq, *New Developments in Anti-HIV Chemotherapy, Current medicinal Chem.* 2001 8(13):1543-1572; G. Moyle, *The Emerging Roles of Non-Nucleoside Reverse Transcriptase Inhibitors in Antiviral Therapy*, Drugs 2001 61(1): 19-26). Although over thirty structural classes of NNRTIs have been identified in the laboratory, only three compounds have been approved for HIV therapy: efavirenz, nevirapine and delavirdine.

Initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, *Eur. Soc. Clin. Microbiol. and Inf. Dis.* 2003 9(3):186-193) The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

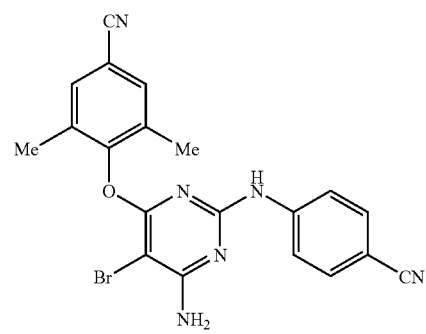

8a

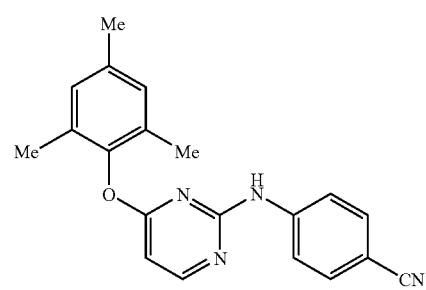

8b

Pyrimidine compounds that inhibitor HIV-1 reverse transcriptase have been disclosed (J. Guillemont et al., WO2006/035068 published Apr. 6, 2006; J. Guillemont et al., WO2006/035067 published Apr. 6, 2006; J. Guillemont et al., WO2006/045828 published May 4, 2006; J. Guillemont et al., WO2006/035369 published Apr. 6, 2006; H. A. De Kock and P. Wigerinck, WO2006/094930 published Sep. 14, 2006; H. A. De Kock and P. Wigerinck, WO2006/087387 published Aug. 24, 2006; P. A. J. Jansen et al., *J. Med. Chem.* 2005 48(6):1901-09; K. Das et al., *J. Med. Chem.* 2004 47(10): 2550-2660; J. Guillemont et al., *J. Med. Chem.* 2005 48(6): 2072-2079). Pyrimidine compounds reported to exhibit effective inhibition of HIV reverse transcriptase include TMC125 (8a) and TMS120 (8b)

SUMMARY OF THE INVENTION

The present invention relates to a compound according to formula I

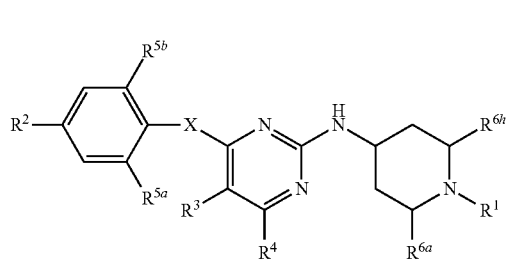

wherein:

$R^1$ is $CO_2$-tert-Bu, $CO_2Et$, phenyl $C_{1-3}$ alkyl, heteroaryl $C_{1-3}$ alkyl, phenyl or heteroaryl wherein said heteroaryl group is selected from the group consisting of pyridinyl, pyridine-N-oxide, pyrimidinyl, thiophenyl, pyrrolyl, thiazolinyl, imidazolinyl or quinolyl and said phenyl or said heteroaryl is optionally substituted with one to three groups independently selected from the group consisting of:

(a) $C_{1-6}$ alkyl
(b) $C_{1-6}$ alkoxy
(c) $C_{1-6}$ haloalkyl
(d) $C_{1-6}$ haloalkoxy
(e) carboxyl
(f) $CONR^{7a}R^{7b}$
(g) $C_{1-6}$ alkoxycarbonyl
(h) cyano
(i) $SO_2$—$C_{1-6}$ alkyl
(j) $SO_2NR^{8a}R^{8b}$
(k) halogen,
(l) nitro,
(m) $C_{1-3}$ cyanoalkyl;
(n) $NR^{10a}R^{10b}$; and,
(o) $NR^{10a}SO_2C_{1-6}$ alkyl
(p) $CHR^{11a}R^{11b}COR^{12}$,
(q) hydroxyl, and
(r) $C_{1-6}$ heteroalkyl;

$R^2$ is —CN, —CH=CHCN, $C_{1-3}$ alkyl or halogen;
$R^3$ is hydrogen, halogen, amino or $C_{1-6}$ haloalkyl;
$R^4$ is hydrogen or amino;
$R^{5a}$ and $R^{5b}$ are independently hydrogen, $C_{1-6}$ alkyl, $C_{1-6}$ alkoxy or halogen;

$R^{6a}$ and $R^{6b}$ independently are hydrogen or together are ethylene;

$R^{7a}$ and $R^{7b}$
(i) taken independently, one of $R^{7a}$ and $R^{7b}$ is hydrogen, $C_{1-6}$ alkyl or $C_{3-7}$ cycloalkyl and the other of $R^{7a}$ and $R^{7b}$ is selected from the group consisting of hydrogen, $C_{1-6}$ alkyl, $C_{1-6}$ heteroalkyl, $C_{1-6}$ alkylsulfonyl, $C_{1-6}$ hydroxyalkyl, $C_{1-3}$ aminoalkyl-$C_{1-6}$ alkyl, $C_{1-3}$ dialkylamino-$C_{1-6}$ alkylalkyl and $C_{1-6}$ aminoalkyl;
(ii) taken together with the nitrogen atom to which they are attached, form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or,
(iii) taken together are $(CH_2)_2$—$X^1$—$(CH_2)_2$;

$R^{8a}$ and $R^{8b}$
(i) taken independently, one of $R^{8a}$ and $R^{8b}$ is hydrogen or $C_{1-6}$ alkyl and the other of $R^{8a}$ and $R^{8b}$ is selected from the group consisting of hydrogen, $C_{1-6}$ alkyl, $C_{1-6}$ acyl and $C_{1-6}$ heteroalkyl;
(ii) taken together with the nitrogen atom to which they are attached, form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or,
(iii) taken together are $(CH_2)_2$—$X^1$—$(CH_2)_2$;

$R^9$ is hydrogen, $C_{1-3}$ alkyl or $C_{1-3}$ acyl;
$R^{10a}$ and $R^{10b}$ are independently hydrogen, $C_{1-3}$ alkyl or $C_{1-6}$ acyl; $R^{11a}$ is hydrogen or halogen;
$R^{11b}$ is hydrogen, halogen, $C_{1-6}$ alkyl, $C_{1-6}$ alkoxy or $C_{1-6}$ hydroxyalkyl;
$R^{12}$ is hydroxyl, $C_{1-6}$ alkoxy or $NR^{7a}R^{7b}$;
X is NH or O;
$X^1$ is O, $S(O)_p$ or $NR^9$
p is an integer from 0 to 2; or,
pharmaceutically acceptable salts thereof.

Compounds of formula I inhibit HIV-1 reverse transcriptase and afford a method for prevention and treatment of HIV-1 infections and the treatment of AIDS and/or ARC. HIV-1 undergoes facile mutations of its genetic code resulting in strains with reduced susceptibility to therapy with current therapeutic options. The present invention also relates to compositions containing compounds of formula I useful for the prevention and treatment of HIV-1 infections and the treatment of AIDS and/or ARC. The present invention further relates to compounds of formula I that are useful in mono therapy or combination therapy with other anti-viral agents.

DETAILED DESCRIPTION OF THE INVENTION

The phrase "as defined herein above" refers to the broadest definition for each group as provided in the Summary of the Invention or the broadest claim. In other embodiments provided below, substituents present in each embodiment which are not explicitly defined retain the broadest definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, $10^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

When any variable (e.g., $R^1$, $R^{4a}$, Ar, $X^1$ or Het) occurs more than one time in an constituent or in any formula depicting and describing compounds employed or claimed in the present invention, its definition on each occurrence is independent of its definition at every other occurrence. Also, combinations of substituents and/or variables are permissible only if such compounds result in stable compounds. (Merck WO2007/002368)

The symbols "*" at the end of a bond or "------" drawn through a bond each refer to the point of attachment of a functional group or other chemical moiety to the rest of the molecule of which it is a part. Thus, for example:

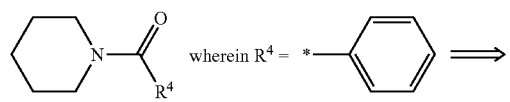

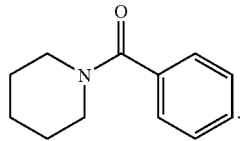

In one embodiment of the present invention there is provided a compound according to formula I wherein $R^1$, $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, X, $X^1$ and p are as defined herein above. The terms "as defined above" and "as defined herein above" when referring to a variable incorporates by reference the broadest definition of the variable provided in the Summary of the Invention or the broadest claim.

In another embodiment of the present invention there is provided a compound according to formula I wherein $R^{7a}$, $R^{7b}$, $R^{8a}$ and $R^{8b}$ are hydrogen and $R^1$, $R^2$, $R^3$, $R^4$, $R^{5a}$, $R^{5b}$, $R^{6a}$, $R^{6b}$, $R^9$, $R^{10a}$, $R^{10b}$, $R^{11a}$, $R^{11b}$, $R^{12}$ and X are as defined herein above In yet another embodiment of the present invention there is provided a compound according to formula I wherein $R^1$ is optionally substituted phenyl and $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, X, $X^1$ and p are as defined herein above In yet another embodiment of the present invention there is provided a compound according to formula I wherein $R^1$ is optionally substituted phenyl; $R^{7a}$, $R^{7b}$, $R^{8a}$ and $R^{8b}$ are hydrogen; and $R^2$, $R^3$, $R^4$, $R^{5a}$, $R^{5b}$, $R^{6a}$, $R^{6b}$, $R^9$, $R^{10a}$, $R^{10b}$, $R^{11a}$, $R^{11b}$, $R^{12}$, X, $X^1$ and p are as defined herein above In still another embodiment of the present invention there is provided a compound according to formula I wherein $R^1$ is phenyl substituted with $CONR^{7a}R^{7b}$, $SO_2NR^{8a}R^{8b}$ or $SO_2$—$C_{1-6}$ alkyl and wherein the phenyl group is optionally further substituted with a group selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro; $R^{5a}$ and $R^{5b}$ are $CH_3$; and, $R^2$, $R^3$, $R^4$, $R^{6a}$, $R^{6b}$, $R^{7a}$, $R^{7b}$, $R^{8a}$, $R^{8b}$, $R^9$, X, $X^1$ and p are as defined herein above.

In a further embodiment of the present invention there is provided a compound according to formula I wherein $R^1$ is phenyl substituted with $CONH_2$, $SO_2NH_2$ or $SO_2$—$C_{1-6}$ alkyl and wherein the phenyl group is optionally further substituted with a group selected from the 9 group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro; $R^{5a}$ and $R^{5b}$ are $CH_3$; and, $R^2$, $R^3$, $R^4$, $R^{6a}$, $R^{6b}$ and X are as defined herein above.

In yet another embodiment of the present invention there is provided a compound according to formula I wherein $R^1$ is phenyl substituted with $CONH_2$, $SO_2NH_2$ or $SO_2$—$C_{1-6}$ alkyl and wherein the phenyl group is optionally further substituted with a group selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro; $R^3$ is hydrogen or bromine; $R^4$ is hydrogen; $R^{5a}$ and $R^{5b}$ are $CH_3$; and, $R^2$, $R^{6a}$, $R^{6b}$ and X are as defined herein above.

In still another embodiment of the present invention there is provided a compound according to formula I wherein $R^1$ is phenyl substituted at the three position with $CONH_2$, $SO_2NH_2$ or $SO_2$—$C_{1-6}$ alkyl and wherein the phenyl group is optionally further substituted with a group selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, 24 and, (k) nitro; $R^{5a}$ and $R^{5b}$ are $CH_3$; and, $R^2$, $R^3$, $R^4$, $R^{6a}$, $R^{6b}$ and X are as defined herein above.

In another embodiment of the present invention there is provided a compound according to formula I wherein $R^1$ is 3-carboxamido-phenyl, 3-aminosulfonyl-phenyl or 3-methanesulfonyl-27 phenyl; $R^3$ is hydrogen or bromine, and $R^4$ is hydrogen; $R^{5a}$ and $R^{5b}$ are $CH_3$; and, $R^2$, $R^{6a}$, $R^{6b}$ and X are as defined herein above.

In a further embodiment of the present invention there is provided a compound according to formula I wherein $R^1$ is optionally substituted phenyl $C_{1-3}$ alkyl or optionally substituted heteroaryl $C_{1-3}$ alkyl; $R^{10a}$ and $R^{10b}$ are hydrogen; and, $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $X$, $X^1$ and p are as defined herein above.

In a further embodiment of the present invention there is provided a compound according to formula I wherein $R^1$ is optionally substituted phenyl $C_{1-3}$ alkyl and $R^2$, $R^3$, $R^4$, $R^5$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $X$, $X^1$ and p are as defined herein above.

In still another embodiment of the present invention there is provided a compound according to formula I wherein $R^1$ is phenyl $C_{1-3}$ alkyl substituted with $CONR^{7a}R^{7b}$, $SO_2NR^{8a}R^{8b}$ or $SO_2$—$C_{1-6}$ alkyl and wherein the phenyl group is optionally further substituted with a group selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro; $R^{5a}$ and $R^{5b}$ are $CH_3$; and, $R^2$, $R^3$, $R^4$, $R^{6a}$, $R^{6b}$, $R^{7a}$, $R^{7b}$, $R^{8a}$, $R^{8b}$, $R^9$, $X$, $X^1$ and p are as defined herein above In a further embodiment of the present invention there is provided a compound according to formula I wherein $R^1$ is phenyl $C_{1-3}$ alkyl substituted at the four position with $CONH_2$, $SO_2NH_2$ or $SO_2$—$C_{1-6}$ alkyl and wherein the phenyl group is optionally further substituted with a group selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro; $R^{5a}$ and $R^{5b}$ are $CH_3$; and, $R^2$, $R^3$, $R^4$, $R^{6a}$, $R^{6b}$ and X are as defined herein above.

In a further embodiment of the present invention there is provided a compound according to formula I wherein $R^1$ is phenyl $C_{1-3}$ alkyl substituted at the four position with $CONH_2$, $SO_2NH_2$ or $SO_2$—$C_{1-6}$ alkyl and wherein the phenyl group is optionally further substituted with a group selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro; $R^3$ is hydrogen or bromine; $R^4$ is hydrogen; $R^{5a}$ and $R^{5b}$ are $CH_3$; and, $R^2$, $R^{6a}$, $R^{6b}$ and X are as defined herein above.

In another embodiment of the present invention there is provided a compound according to formula I wherein $R^1$ is optionally substituted heteroaryl $C_{1-3}$ alkyl or heteroaryl; $R^4$, $R^7$, $R^{7b}$, $R^{8a}$ and $R^{8b}$ are hydrogen and $R^1$, $R^2$, $R^3$, $R^4$, $R^{5a}$, $R^{5b}$, $R^{6a}$, $R^{6b}$, $R^9$, $R^{10a}$, $R^{10b}$ and X are as defined herein above.

A compound according to claim 1 wherein $R^1$ is phenyl substituted with $CR^{11a}R^{11b}COR^{12}$ and $R^{11a}$ and $R^{11b}$ are hydrogen and $R^{12}$ is $C_{1-6}$ alkoxy or $NR^{7a}R^{7b}$.

In still another embodiment of the present invention there is provided a compound according to claim 1 which compound is a free base or a pharmaceutically acceptable salt of a compound selected from a compound in TABLE 1-5.

In another embodiment of the present invention there is provided a method for treating an HIV-1 infection, or preventing an HIV-1 infection, or treating AIDS or ARC, comprising administering to a host in need thereof a therapeutically effective amount of a compound according to formula I wherein $R^1$, $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, $X$, $X^1$ and p are as defined herein above.

In another embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, $X$, $X^1$ and p are as defined herein above and at least one compound selected from the group consisting of HIV protease inhibitors, nucleoside reverse transcriptase inhibitors, non-nucleoside reverse transcriptase inhibitors, CCR5 antagonists and viral fusion inhibitors. In still another embodiment of the present invention the compound of formula I can be co-administered with at least one compound selected from the group consisting of HIV protease inhibitors, nucleoside reverse transcriptase inhibitors, non-nucleoside reverse transcriptase inhibitors, integrase inhibitor, CCR5 antagonists and viral fusion inhibitors.

In another embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, $R^4$, $R^{5a}$, $R^{1b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, $X$, $X^1$ and p are as defined herein above and at least one compound selected from the group consisting of zidovudine, lamivudine, didanosine, zalcitabine, stavudine, rescriptor, sustiva, viramune, efavirenz, nevirapine, delavirdine, saquinavir, ritonavir, nelfinavir, indinavir, amprenavir, lopinavir and enfuvirtide. In still another embodiment of the present invention the method comprises co-administering at least one compound selected from the group consisting of zidovudine, lamivudine, didanosine, zalcitabine, stavudine, emtricibine, abacavir, tenofovir, efavirenz, nevirapine or delavirdine saquinavir, ritonavir, nelfinavir, indinavir, amprenavir, atazanavir, lopinavir, enfuvirtide, maraviroc and raltegravin In another embodiment of the present invention there is provided a method for inhibiting HIV-1 reverse transcriptase in a host infected with HIV-1 comprising administering to a host in need thereof a therapeutically effective amount of a compound according to formula I wherein $R^1$, $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, $X$, $X^1$ and p are as defined herein above.

In another embodiment of the present invention there is provided a method for inhibiting HIV-1 reverse transcriptase in a host infected with HIV-1 wherein the HIV-1 reverse transcriptase with at least one mutation compared to wild type HIV-1 comprising administering to a host in need thereof a therapeutically effective amount of a compound according to formula I wherein $R^1$, $R^2$, $R^3$, $R^4$, $R^5$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, $X$, $X^1$ and p are as defined herein above.

In another embodiment of the present invention there is provided a method for inhibiting HIV-1 reverse transcriptase in a host infected with HIV-1 wherein the HIV-1 reverse transcriptase exhibits reduced susceptibility to efavirenz, nevirapine or delavirdine comprising administering to a host in need thereof a therapeutically effective amount of a compound according to formula I wherein $R^1$, $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, $X$, $X^1$ and p are as defined herein above.

In an embodiment there is provided a pharmaceutical composition comprising a compound according to formula I wherein $R^1$, $R^2$, $R^3$, $R^4$, $R^{5a}$, $R^{5b}$, $R^{6a}$, $R^{6b}$, $R^{7a}$, $R^{7b}$, $R^{8a}$, $R^{8b}$, $R^9$, $R^{10a}$, $R^{10b}$, $R^{11a}$, $R^{11b}$, $R^{12}$, X, $X^1$ and p are as defined herein above and at least one carrier, excipient or diluent.

In another embodiment of the present invention there is provided a compound according to formula I wherein: $R^1$ is $CO_2$-tert-Bu, $CO_2Et$, phenyl $C_{1-3}$ alkyl, heteroaryl $C_{1-3}$ alkyl, phenyl or heteroaryl wherein said heteroaryl group is selected from the group consisting of pyridinyl, pyrimidinyl, thiophenyl, pyrrolyl, thiazolinyl, imidazolinyl or quinolyl and said phenyl or said heteroaryl is optionally substituted with one to three groups independently selected from the group consisting of: (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $CONR^{7a}R^{7b}$, (g) $C_{1-6}$ alkoxycarbonyl, (h) cyano, (i) $SO_2$—$C_{1-6}$ alkyl, (j) $SO_2NR^{8a}R^{8b}$, (k) $C_{1-6}$ acyl-amino, (l) halogen, (m) nitro, (n) $C_{1-3}$ cyanoalkyl, (o) $NR^{10a}R^{10b}$; and (p) $NR^{10a}SO_2C_{1-6}$ alkyl; $R^2$ is —CN, —CH=CHCN, $C_{1-3}$ alkyl or halogen; $R^3$ is hydrogen, halogen or $C_{1-6}$ haloalkyl; $R^4$ is hydrogen or amino; $R^{5a}$ and $R^{5b}$ are independently hydrogen, $C_{1-6}$ alkyl, halogen; $R^{6a}$ and $R^{6b}$ independently are hydrogen or together are ethylene; $R^{7a}$ and $R^{7b}$ (i) taken independently, one of $R^{7a}$ and $R^{7b}$ is hydrogen or $C_{1-6}$ alkyl and the other of $R^{7a}$ and $R^{7b}$ is selected from the group consisting of hydrogen, $C_{1-6}$ alkyl and $C_{1-6}$ heteroalkyl; (ii) taken together with the nitrogen atom to which they are attached, form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or, (iii) taken together are $(CH_2)_2$—$X^1$—$(CH_2)_2$; $R^{8a}$ and $R^{8b}$ (i) taken independently, one of $R^{8a}$ and $R^{8b}$ is hydrogen or $C_{1-6}$ alkyl and the other of $R^{8a}$ and $R^{8b}$ is selected from the group consisting of hydrogen, $C_{1-6}$ alkyl, $C_{1-6}$ acyl and $C_{1-6}$ heteroalkyl; (ii) taken together with the nitrogen atom to which they are attached, form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or, (iii) taken together are $(CH_2)_2$—$X^1$—$(CH_2)_2$; $R^9$ is hydrogen, $C_{1-3}$ alkyl or $C_{1-3}$ acyl; $R^{10a}$ and $R^{10b}$ are independently hydrogen or $C_{1-3}$ alkyl; X is NH or O; $X^1$ is O, $S(O)_p$ or $NR^9$; p is an integer from 0 to 2; or, pharmaceutically acceptable salts thereof.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-3}$ alkyl" as used herein refers to an alkyl composed of 1 to 3 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, and 3-phenylpropyl. The terms "arylalkyl" or "aralkyl" are interpreted similarly except R' is an aryl radical. The terms "(hetero)arylalkyl" or "(hetetero)aralkyl" are interpreted similarly except R' is optionally an aryl or a heteroaryl radical. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2CH$(i-Pr)$CH_2$—), unless otherwise indicated. The open valences of an alkylene group are not attached to the same atom. Examples of alkylene radicals include, but are not limited to, methylene, ethylene ($CH_2CH_2$), propylene, 2-methyl-propylene, 1,1-dimethyl-ethylene, butylene, 2-ethylbutylene.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "haloalkoxy" as used herein refers to a group —OR where R is haloalkyl as defined herein. The term "haloalkylthio" as used herein refers to a group —SR where R is haloalkyl as defined herein.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "aryl" as used herein denotes a monovalent aromatic carbocyclic radical containing 5 to 15 carbon atoms consisting of one individual ring, or one or more fused rings in which at least one ring is aromatic in nature, which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, indanyl, tetrahydronaphthyl, 3,4-methylenedioxyphenyl, 1,2,3,4-tetrahydroquinolin- 7-yl, and the like. The point of attachment of bicyclic aryl substituents with a heteroatom in one of the rings is on the carbocyclic aromatic ring.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazole, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, 3 benzothiazole and benzisothiazole. Bicyclic moieties can be optionally substituted on either ring; however the point of attachment is on a ring containing a heteroatom. The term "(hetero)aryl" or "(het)aryl" is used to indicate that a particular moiety can be either an aryl or a heteroaryl group.

The term "heteroarylalkyl" or "heteroaralkyl" means the radical of the formula R'R", wherein R' is an optionally substituted heteroaryl radical as defined herein, and R" is an alkylene radical as defined herein with the understanding that the attachment point of the heteroaryl radical will be on the alkylene radical. Examples of heteroarylalky radicals include, but are not limited to, 2-imidazolylmethyl, and 3-pyrrolylethyl.

The terms "alkoxycarbonyl" and "aryloxycarbonyl" as used herein denotes a group of formula —C(=O)OR wherein R is alkyl or aryl respectively and alkyl and aryl are as defined herein.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)$_n$—, RHN(CH$_2$)$_n$—, and R$_2$N(CH$_2$)$_n$— respectively wherein n is 1 to 6 and R is alkyl as defined above. "C$_{1-10}$ alkylamino" as used herein refers to an-aminoalkyl wherein alkyl is C$_{1-10}$. The term "phenylamino" as used herein refers to —NHPh wherein Ph represents an optionally substituted phenyl group.

The term "acylamino" as used herein denotes a group of formula —NHC(=O)R wherein R is hydrogen or lower alkyl as defined herein. C$_{1-6}$ acyl-amino refers to an acylamino group wherein the C(=O)R moiety contains a total of 6 carbon atoms.

The term "halogen" or "halo" as used herein means fluorine, chlorine, bromine, or iodine.

The term "cyanoalkyl" refers to a group RR$^1$ wherein R is cyano and R$^1$ is an alkylene group as defined herein. The term "heteroalkyl" as used herein means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, or alkylamino. Representative examples include, but are not limited to, 2-hydroxy-ethyl, 3-hydroxy-propyl, 2-hydroxy-1-hydroxy-methylethyl, 2,3-dihydroxy-propyl, 1-hydroxy-methylethyl, 3-hydroxy-butyl, 2,3-dihydroxy-butyl, 2-hydroxy-1-methylpropyl, 2-aminoethyl, 3-amino-propyl, 2-methylsulfonyl-ethyl, aminosulfonyl-methyl, aminosulfonyl-ethyl, aminosulfonyl-propyl, methylaminosulfonyl-methyl, methylaminosulfonyl-ethyl, methylaminosulfonyl-propyl, and the like.

The terms "azetidine", "pyrrolidine", "piperidine" and "azepine" refer to a 4-, 5-, 6- or 7-membered cycloalkane respectively wherein a nitrogen atom replaces one carbon atom.

The nitrogen atom of the pyridine ring is optionally substituted with an oxygen atom to form a nitrogen N-oxide. Preparation of N-oxides is well known and may be carried out, for example, in suitable organic solvent (dichloromethane, chloroform, benzene, hexane or t-butanol, etc.) in the presence of an excess of oxidizing agent (e.g., sodium peroxide, hydrogen peroxide, sodium periodate, sodium perborate, meta-chloroperbenzoic acid or other peracid, OXONE® (potassium peroxymonosulfate), potassium permanganate or chromic acid) typically at temperatures from 20-60° C.

The heteroaryl R$^1$ groups designated as pyridinyl, pyrimidinyl, thiophenyl, pyrrolyl, thiazolinyl, imidazolinyl or quinolyl can be linked to the pyrimidine at any carbon at on the heteroaryl ring.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system The term "nucleoside and nucleotide reverse transcriptase inhibitors" ("NRTI"'s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA. Recent progress in development of RTI and PI inhibitors has been reviewed: F. M. Uckun and O. J. D'Cruz, *Exp. Opin. Ther. Pat.* 2006 16:265-293; L. Menendez-Arias, *Eur. Pharmacother.* 2006 94-96 and S. Rusconi and O. Vigano, *Future Drugs* 2006 3(1):79-88.

Typical suitable NRTIs include zidovudine (AZT; RETROVIR®) from GSK; didanosine (ddI; VIDEX®) from Bristol-Myers Squibb Co. (BMS); zalcitabine (ddC; HIVID®) from Roche; stavudine (d4T; ZERIT®) from BMS; lamivudine (3TC; EPIVIR®) from GSK; abacavir (1592U89; ZIAGEN®) disclosed in WO96/30025 and available from GSK; adefovir dipivoxil (bis(POM)-PMEA; PREVON®) Gilead Sciences; lobucavir (BMS-180194), a nucleoside reverse transcriptase inhibitor disclosed in EP-0358154 and EP-0736533 and under development by BMS; BCH-10652, a reverse transcriptase inhibitor (in the form of a racemic mixture of BCH-10618 and BCH-10619) under development by Biochem Pharma; emitricitabine [(−)-FTC] licensed from Emory University under Emory Univ. U.S. Pat. No. 5,814,639 and under development by Gilead Sciences, Inc; Evucitabine (β-L-D4FC; β-L-2',3'-dideoxy-5-fluoro-cytidene) licensed by Yale University to Vion Pharmaceuticals; DAPD, the purine nucleoside, (−)-β-D-2,6-diamino-purine dioxolane disclosed in EP-0656778 and licensed by Emory University and the University of Georgia to Triangle Pharmaceuticals; and lodenosine (FddA), 9-(2,3-dideoxy-2-fluoro-β-D-threo-pentofuranosyl)adenine, an acid stable purine-based reverse transcriptase inhibitor discovered by the NIH and under development by U.S. Bioscience Inc.

Three NNRTIs have been approved in the USA: nevirapine (BI-RG-587; VIRAMUNE®) available from Boehringer Ingelheim (BI); delaviradine (BHAP, U-90152; RESCRIPTOR®) available from Pfizer; efavirenz (DMP-266, SUSTIVA®) a benzoxazin-2-one from BMS. Other NNRTIs currently under investigation include PNU-142721, a furopyridine-thio-pyrimide under development by Pfizer; capravirine (S-1153 or AG-1549; 5-(3,5-dichlorophenyl)-thio-4-isopropyl-1-(4-pyridyl)methyl-1H-imidazol-2-ylmethyl carbonate) by Shionogi and Pfizer; emivirine [MKC-442; (1-(ethoxy-methyl)-5-(1-methylethyl)-6-(phenylmethyl)-(2,4(1H,3H)-pyrimidinedione)] by Mitsubishi Chemical Co. and Triangle Pharmaceuticals; (+)-calanolide A (NSC-675451) and B, coumarin derivatives disclosed in NIH U.S. Pat. No. 5,489,697, licensed to Sarawak/Advanced Life Sciences; etravirine (TMC-125; 4-[6-amino-5-bromo-2-(4-cyano-phenylamino)-pyrimidin-4-yloxy]-3,5-dimethyl-benzonitrile) and DAPY (TMC120; 4-{4-[4-((E)-2-cyano-vinyl)-2,6-dimethyl-phenylamino]-pyrimidin-2-ylamino}-benzonitrile) by Tibotec-Virco and Johnson & Johnson; BILR-355 BS (12-ethyl-8-[2-(1-hydroxy-quinolin-4-yloxy)-ethyl]-5-methyl-1,12-dihydro-5H-1,5,10,12-tetraaza-dibenzo[a,e]cycloocten-6-one by Boehringer-Ingleheim; PHI-236 (7-bromo-3-[2-(2,5-dimethoxy-phenyl)-ethyl]-3,4-dihydro-1H-pyrido[1,2-a][1,3,5]triazine-2-thione) and PHI-443 (TMC-278, 1-(5-bromo-pyridin-2-yl)-3-(2-thiophen-2-yl-ethyl)-thiourea) by Paradigm Pharmaceuticals.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN® as well as nonpeptide protease inhibitors e.g., VIRACEPT®.

Typical suitable PIs include saquinavir available in hard gel capsules as INVIRASE® and in soft gel capsules as FORTOVASE® from Roche; ritonavir (ABT-538) available as NORVIR from Abbott Laboratories; Lopinavir (ABT-378) also available from Abbot; KALETRA®, is co-formulation lopinavir and a sub-therapeutic dose of ritonavir available from Abbott Laboratories; indinavir (MK-639) available as CRIXIVAN® from Merck & Co.; nelfnavir (AG-1343) available as VIRACEPT® from Agouron Pharmaceuticals, Inc.; amprenavir (141W94) available as AGENERASE® from Vertex Pharmaceuticals, Inc. and GSK; tipranavir (PNU-140690) available as APTIVUS® from BI; lasinavir (BMS-234475/CGP-61755) by BMS; BMS-2322623, an azapeptide under development by BMS as a 2nd-generation HIV-1 PI; GW-640385X (VX-385) under development in a collaboration between GSK and Vertex; AG-001859 in preclinical development by Agouron/Pfizer; SM-309515 under development by Sumitomo Pharmaceuticals.

Additional PIs in preclinical development include N-cycloalkylglycines by BMS, α-hydroxyarylbutanamides by Enanta Pharmaceuticals; α-hydroxy-γ-[[(carbocyclic- or heterocyclic-substituted)amino)carbonyl]alkanamide derivatives; γ-hydroxy-2-(fluoroalkylaminocarbonyl)-1-piperazinepentanamides by Merck; dihydropyrone derivatives and α- and β-amino acid hydroxyethylamino sulfonamides by Pfizer; and N-aminoacid substituted L-lysine derivatives by Procyon. Entry of HIV into target cells requires CD-4 cell surface receptor and the CCR5 (M-tropic strains) and CXCR4 (T-tropic strains) chemokine co-receptors. Chemokine antagonize which block viral binding to the chemokines are useful inhibitors of viral infection. Takeda's identified TAK-779 as a potential CCR5 antagonist. (M. Shiraishi et al., *J. Med. Chem.* 2000 43(10):2049-2063; M. Babba et al. *Proc. Nat. Acad. Sci. USA* 1999 96:5698-5703) and TAK-220 (C. Tremblay et al. *Antimicrob. Agents Chemother.* 2005 49(8): 3483-3485). WO0039125 (D. R. Armour et al.) and WO0190106 (M. Perros et al.) disclose heterocyclic compounds that are potent and selective CCR5 antagonists. Miraviroc (UK-427,857; MVC) has advanced by Pfizer to phase III clinical trials and show activity against HIV-1 isolates and laboratory strains (P. Dorr et al., *Antimicrob. Agents Chemother.* 2005 49(11):4721-4732; A. Wood and D. Armour, *Prog. Med. Chem.* 2005 43:239-271; C. Watson et al., *Mol. Pharm.* 2005 67(4):1268-1282; M. J. Macartney et al., 43$^{rd}$ *Intersci. Conf. Antimicrob. Agents Chemother*. Sep. 14-17, 2003, Abstract H-875). Schering has advanced Sch-351125 (SCH-C) into Phase I/II clinical studies and reported the advance of a more potent follow-up compound, Vicroviroc (Sch417690, SCH-D) into Phase I studies. (S. W. McCrombie et al., WO00066559; B. M. Baroudy et al. WO00066558; A. Palani et al., *J. Med. Chem.* 2001 44(21): 3339-3342; J. R. Tagat et al., *J. Med. Chem.* 2001 44(21): 3343-3346; J. A. Esté, *Cur. Opin. Invest. Drugs* 2002 3(3): 379-383; J. M. Struzki et al. *Proc. Nat. Acad. Sci. USA* 2001 98:12718-12723). Merck has disclosed the preparation of (2S)-2-(3-chlorophenyl)-1-N-(methyl)-N-(phenylsulfonyl) amino]-4-[spiro(2,3-dihydrobenzothiophene-3,4'-piperidin-1'-yl)butane S-oxide (1) and related derivatives with good affinity for the CCR5 receptor and potent-HIV activity. (P. E. Finke et al., *Bioorg. Med. Chem. Lett.*, 2001 11:265-270; P. E. Finke et al., *Bioorg. Med. Chem. Lett.*, 2001 11:2469-2475; P. E. Finke et al., *Bioorg. Med. Chem. Lett.*, 2001 11:2475-2479; J. J. Hale et al., *Bioorg. Med. Chem. Lett.*, 2001 11:2741-22745; D. Kim et al., *Bioorg. Med. Chem. Lett.*, 2001 11:3099-3102) C. L. Lynch et al. *Org. Lett.* 2003 5:2473-2475; R. S. Veazey et al. *J. Exp. Med.* 2003 198:1551-1562. GSK-873140 (ONO-4128, E-913, AK-602) was identified in a program initiated at Kumamoto University (K. Maeda et al. *J. Biol. Chem.* 2001 276:35194-35200; H. Nakata et al. *J. Virol.* 2005 79(4):2087-2096) and has been advanced to clinical trials. In WO00/166525; WO00/187839; WO02/076948; WO02/076948; WO02/079156, WO2002070749, WO2003080574, WO2003042178, WO2004056773, WO2004018425 Astra Zeneca disclose 4-amino piperidine compounds which are CCR5 antagonists. In U.S. Publication No. 20050176703 published Aug. 11, 2005, S. D. Gabriel and D. M. Rotstein disclosed heterocyclic CCR5 antagonist capable of preventing HIV cell entry. In U.S. Publication No. 20060014767 published Jan. 19, 2006, E. K. Lee et al. disclosed heterocyclic CCR5 antagonist capable of preventing HIV cell entry.

Attachment Inhibitors effectively block interaction between viral envelope proteins and chemokine receptors or CD40 protein. TNX-355 is a humanized IgG4 monoclonal antibody that binds to a conformational epitope on domain 2 of CD4. (L. C. Burkly et al., *J. Immunol.* 1992 149:1779-87) TNX-355 can inhibit viral attachment of CCR5-, CXCR4- and dual/mixed tropic HIV-1 strains. (E. Godofsky et al., In Vitro Activity of the Humanized Anti-CD4 Monoclonal Antibody, TNX-355, against CCR5, CXCR4, and Dual-Tropic Isolates and Synergy with Enfuvirtide, 45*th Annual Interscience Conference on Antimicrobial Agents and Chemotherapy (ICAAC)*. Dec. 16-19, 2005, Washington D.C. Abstract # 3844; D. Norris et al. TNX-355 in Combination with Optimized Background Regime (OBR) Exhibits Greater Antiviral Activity than OBR Alone in HIV-Treatment Experienced Patients, 45*th Annual Interscience Conference on Antimicrobial Agents and Chemotherapy (ICAAC)*. Dec. 16-19, 2005, Washington D.C. Abstract # 4020.)

Macromolecular therapeutics including antibodies, soluble receptors and biologically active fragments thereof have become an increasingly important adjunct to conventional low molecular weight drugs. (O. H. Brekke and I. Sandlie *Nature Review Drug Discov.* 2003 2:52-62; A. M. Reichert *Nature Biotech.* 2001 19:819-821) Antibodies with high specificity and affinity can be targeted at extra-cellular proteins essential for viral cell fusion. CD4, CCR5 and CXCR4 have been targets for antibodies which inhibit viral fusion.

V. Roschke et al. (Characterization of a Panel of Novel Human Monoclonal Antibodies that Specifically Antagonize CCR5 and Block HIV-1 Entry, 44*th Annual Interscience Conference on Antimicrobial Agents and Chemotherapy (ICAAC)*. Oct. 29, 2004, Washington D.C. Abstract # 2871) have disclosed monoclonal antibodies which bind to the CCR5 receptor and inhibit HIV entry into cells expressing the CCR5 receptor. L. Wu and C. R MacKay disclose in U.S. Ser. No. 09/870,932 filed May 30, 2001 disclose monoclonal antibodies 5C7 and 2D7 which bind to the CCR5 receptor in a manner capable of inhibiting HIV infection of a cell. W. C. Olsen et al. (*J. Virol.* 1999 73(5):4145-4155) disclose monoclonal antibodies capable of inhibiting (i) HIV-1 cell entry, (ii) HIV-1 envelope-mediated membrane fusion, (iii) gp120 binding to CCR5 and (iv) CC-chemokine activity. Synergism between the anti-CCR5 antibody Pro140 and a low molecular weight CCR5 antagonists have been disclosed by Murga et al. (3rd IAS Conference on HIV Pathogenesis and Treatment, Abstract TuOa.02.06. Jul. 24-27, 2005, R10 de Janeiro, Brazil) Anti-CCR5 antibodies have been isolated which inhibit HIV-1 cell entry also have been disclosed by M. Brandt et al. in U.S. Ser. No. 11/394,439 filed Mar. 31, 2006.

FUZEON® (T-20, DP-178, pentafuside) is disclosed in U.S. Pat. No. 5,464,933. T-20 and an analog, T-1249, are analogs of HIV gp41 fragment which are effectively inhibit a conformational change required for HIV fusion. T-20 has been approved and is available from Roche and Trimeris. FUZEON is administered as a continuous sc infusion or injection in combination therapy with other classes of anti HIV drugs.

Other antiviral agents which may be useful in HIV therapy include hydroxyurea, ribavirin, IL-2, IL-12, pentafuside. Hydroyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN® (aldesleukin) from Chiron Corp. as a lyophilized powder for IV infusion or sc administration. IL-12 is disclosed in WO96/25171 and is available from Roche and Wyeth Pharmaceuticals. Ribavirin, 1-β-D-ribofuranosyl-1H-1,2,4-triazole-3-carboxamide, is described in U.S. Pat. No. 4,211,771 and is available from ICN Pharmaceuticals.

Abbreviations used in this application include: acetyl (Ac), acetic acid (HOAc), azo-bis-isobutyrylnitrile (AIBN), 1-N-hydroxybenzotriazole (HOBt), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), N-chlorosuccinimide (NCS), 1,8-diazabicyclo[5.4.0]undec-7-ene (DBU), N-methylmorpholine (NMM), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), di-iso-propylethylamine (DIPEA), pyridine (pyr), di-iso-butylaluminumhydride, DIBAL-H, room temperature, rt or RT, N,N-dimethyl acetamide (DMA), tert-butyldimethylsilyl or t-BuMe$_2$Si, (TBDMS), 4-N,N-dimethylaminopyridine (DMAP), triethylamine (Et$_3$N or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether (Et$_2$O), trimethylsilyl or Me$_3$Si (TMS), ethyl (Et), p-toluenesulfonic acid monohydrate (TsOH or pTsOH), lithium hexamethyl disilazane (LiHMDS), 4-Me-C$_6$H$_4$OS$_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R.

Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature and number of the R groups can varied to afford the various compounds contemplated in this invention. The general formulae in the schemes are intended to be illustrative and are not intended to imply a limitation to the scope of the invention which is defined by the appended claims. Moreover, the reaction conditions are exemplary and alternative conditions are well known. The reaction sequences in the following examples are not meant to limit the scope of the invention as set forth in the claims.

There are a multitude of references known in the art that teach methods for the preparation of substituted pyrimidines. The reader is referred to (a) D. J. Brown; Pyrimidines and their Benzo Derivatives. In *Comprehensive Heterocyclic Chemistry*, 1st Edition; A. R. Katritzky and C. W. Rees, Eds.; Pergamon Press: Oxford, 1984, vol. 3, pp. 106-141 and references cited therein, (b) K. Undheim and T. Benneche: Pyrimidines and their Benzo Derivatives. In *Comprehensive Heterocyclic Chemistry*, 2nd Edition; A. R. Katritzky, C. W. Rees and E. F. V. Scriver, Eds.; Pergamon Press: Oxford, 1996, vol. 6, pp. 195-221 and references cited therein, (c) D. J. Brown; The Pyrimidines. In *The Chemistry of Heterocyclic Compounds*; A. Weissberger, Ed.; Wiley Interscience, New York, 1962, vol 52, pp. 49-238 and references cited therein (1-Benzyl-piperidin-4-yl)-(4-phenoxy-pyrimidin-2-yl)-amines derivatives exemplified in TABLE 1 were prepared (SCHEME A) from either 2,4-dichloropyrimidine or 5-bromo-2,4-dichloro-pyrimidine (Route A1). Nucleophilic displacement of 2- and 4- and/or 6-halo-substituted pyrimidines by alkoxy and aryloxy nucleophiles occurs readily except in the presence of strong electron-releasing substituents on other positions of the pyrimidine ring. Metal aryloxides more readily react with a 4- or 6-halo substituent than a 2-halo substituent (T. J. Delia and A. Nagarajan, *J. Heterocyclic Chem.* 1998 35:269-273). Thus reaction of a phenol with 10a affords the ether 10b. Subsequent displacement of the 2-chloro substituent with 12 affords 14a. Deprotection by mild acid treatment afforded 14b which was alkylated on the piperidine nitrogen with an optionally substituted benzyl halide to afford the compounds of TABLE 1. Alternatively, the compounds can be prepared from 2-methylthio-4-chloro-pyrimidine (26a, Route A2)

SCHEME A

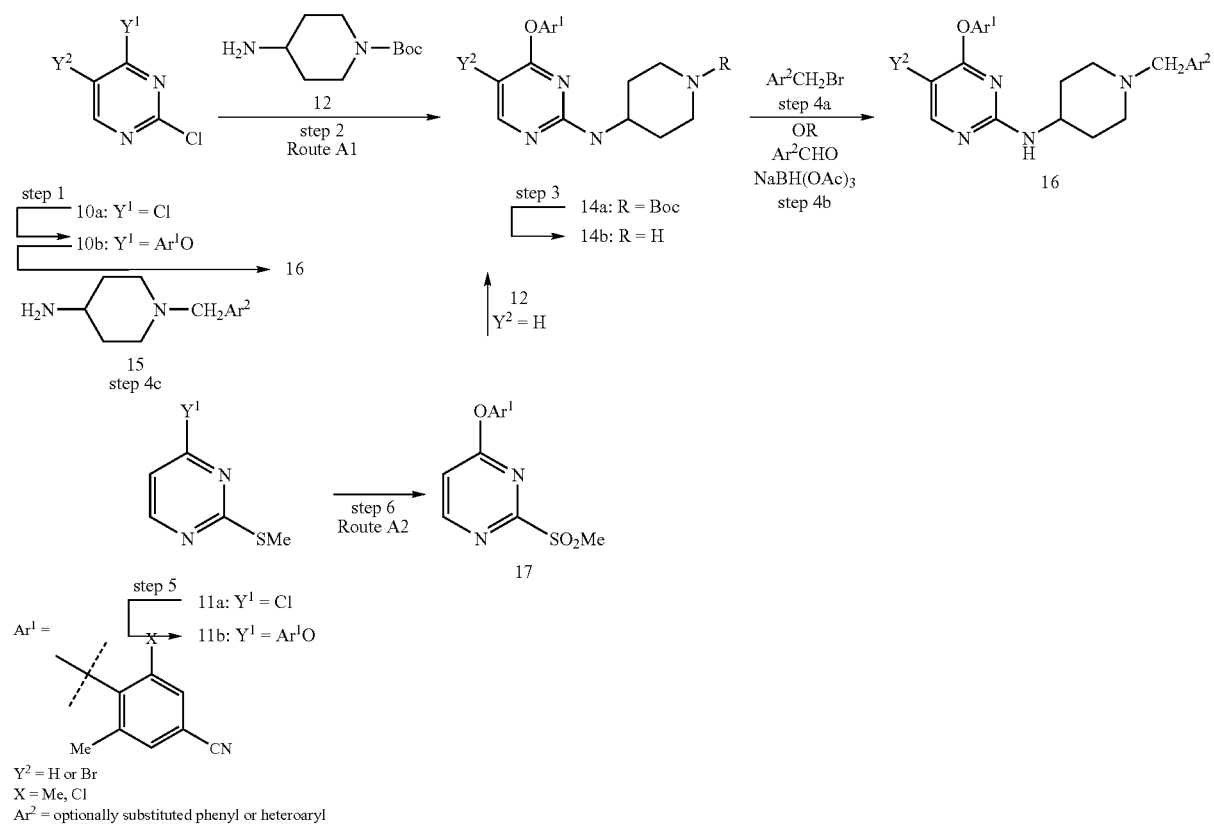

$Y^2$ = H or Br
X = Me, Cl
$Ar^2$ = optionally substituted phenyl or heteroaryl

Displacement of a chloro substituent on a pyrimidine by a phenol is conveniently carried out in the presence of a base. Such a base is, for example, an alkali metal or alkaline metal carbonate or hydroxide, such as $Na_2CO_3$, $K_2CO_3$, $CaCO_3$, $Cs_2CO_3$, NaOH or KOH or an organic amine base such as, pyridine, 2,6-lutidine, collidine, TEA, NMM, DBU or DBN. Alternately an alkali metal hydride such as NaH or KH, or an alkali metal amide such as $NaNH_2$, $KNH_2$, $LiN(SiMe_3)_2$ can be used to produce an alkali metal alkoxide. The reaction is conveniently carried out in an inert solvent such as an ether solvent, e.g., THF, DME or dioxane, an aromatic hydrocarbon solvent, e.g., toluene, or a polar aprotic solvent such as DMF, NMP or DMSO. The reaction is conveniently effected at a temperature in the range of 10-120° C. Subsequent displacement of the 2-chloro substituent was conveniently carried out in the presence of neat amine 12 at elevated temperatures.

The Boc protecting group is labile under acidic conditions and it can be removed by treatment with TFA or HCl in a solvent like DCM, dioxane or THF preferable at RT (see *Protective Groups in Organic Synthesis*, T. W. Greene and P. G. M. Wuts, $3^{rd}$ Edition, 1999, Wiley-Interscience).

Alkylation of piperidine nitrogen is accomplished by treating the amine or a metal salt of the amine (i.e. a deprotonated form) with an alkylating agent $Ar^2CH_2Z^1$ wherein $Ar^2$ is optionally substituted phenyl or optionally substituted heteroaryl moiety, $Z^1$ is a leaving group such as halo, mesylate, benzenesulphonyloxy or tosylate, optionally in the presence of a base and/or a phase transfer catalyst such as 18-crown-6 (SCHEME A, step 4a). The reaction may typically be carried out in the presence of a base such as TEA, DIPEA, DBU, or an inorganic base such as $Na_2CO_3$, $NaHCO_3$, $K_2CO_3$ or $Cs_2CO_3$, and in a solvent such as MeCN, DMF, DMSO, 1,4-dioxane, THF or toluene. Alternatively, a metal salt of the amine (i.e. a deprotonated form) may be employed in a suitable solvent such as THF, DMF or 1,4-dioxane. Compounds of formula 16 also are accessible by Mitsunobu reaction (D. L. Hughes, The Mitsunobu Reaction, in *Organic Reactions*, Volume 42, 1992, John Wiley & Sons, New York; pp. 335-656) applying optionally substituted benzyl alcohols activated by a mixture of a phosphine such as tributylphosphine (($n$-Bu)$_3$P), triphenylphosphine (Ph$_3$P) and the like and a diazo-compound like diethyl-azodicarboxylate (DEAD), diisopropyl-azodicarboxylate (DIAD) or di-tert-butyl-azodicarboxylate in a non-protic solvent such as THF, toluene, DCM and the like. There is no particular restriction on the nature of the solvent to be employed, provided that it has no adverse effect on the reaction or the reagents involved and that it can at least partially dissolve the reagents. The reaction can take place over a wide range of temperatures ranging from ambient temperatures to the reflux temperature of the solvent employed.

Introduction of the benzyl substituent can also be accomplished by reductive amination of an (hetero)aryl aldehyde with 14b (SCHEME A, step 4b). Reductive amination is preferably carried out carried out by combining an amine and carbonyl compound in the presence of a complex metal hydride reducing agent such as $NaBH_4$, $LiBH_4$, $NaB(CN)H_3$, $Zn(BH_4)_2$, $NaB(OAc)_3H$ or borane/pyridine complex conveniently at a pH of 1-7, or with hydrogen in the presence of a hydrogenation catalyst, e.g. in the presence of Pd/C, at a hydrogen pressure of 1 to 5 bar, preferably at temperatures between 20° C. and the boiling temperature of the solvent used. Optionally a dehydrating agent, such as molecular sieves or $Ti(IV)(O-i-Pr)_4$, is added to facilitate formation of the intermediate imine at ambient temperature. It may also be advantageous to protect potentially reactive groups during the reaction by conventional protecting groups which are cleaved again by conventional methods after the reaction. Reductive amination procedures have been reviewed: R. M. Hutchings and M. K. Hutchings *Reduction of C=N to CHNH by Metal Hydrides* in *Comprehensive Organic Synthesis* col. 8, I. Fleming (Ed) Pergamon, Oxford 1991 pp. 47-54.

If an N-aralkyl-4-amino-piperidine (e.g., 4-amino-N-benzylpiperidine, CASRN 50541-93-0) or N-heteroaralkyl-4-amino-piperidine is available or is prepared from a selectively protected precursor such as 4-(tert-butoxycarbonylamino)piperidine (CASRN 73874-95-0), the fully elaborated piperidinyl side chain can be introduced in a single step (SCHEME A, step 4c).

TABLE I

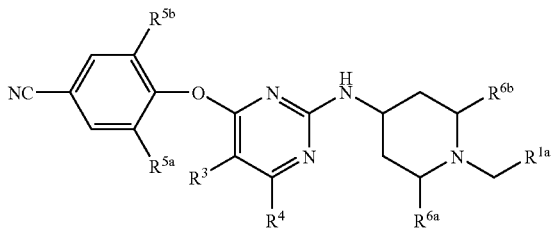

| Cpd. No. | $R^{1a}$ | $R^3$ | $R^4$ | $R^{5a}$ | $R^{5b}$ | $R^{6a}, R^{6b}$ | ms | mp |
|---|---|---|---|---|---|---|---|---|
| I-1 | Ph | H | H | Me | Me | H, H | [M + 1] 414 | 162.0-163.3 |
| I-2 | Ph | Br | H | Me | Me | H, H | (ESI) 492, 494 | 158.0-159.8 |
| I-3 | 4-MeS(O)$_2$—C$_6$H$_4$ | H | H | Me | Me | H, H | 491 | |
| I-4 | 4-HO$_2$C—C$_6$H$_4$ | Br | H | Me | Me | H, H | [M + 1] 536, 538 | |
| I-5 | pyridin-4-yl | Br | H | Me | Me | H, H | [M + 1] 493, 495 | |
| I-6 | 2-thienyl | Br | H | Me | Me | H, H | [M + 1] 498, 500 | |
| I-7 | 3-thienyl | Br | H | Me | Me | H, H | [M + 1] 498, 500 | |

TABLE I-continued

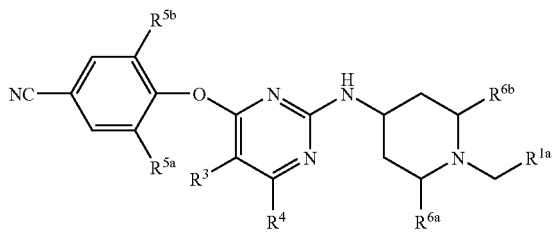

| Cpd. No. | R$^{1a}$ | R$^3$ | R$^4$ | R$^{5a}$ | R$^{5b}$ | R$^{6a}$, R$^{6b}$ | ms | mp |
|---|---|---|---|---|---|---|---|---|
| I-8 | 2-thiazolyl | Br | H | Me | Me | H, H | [M + 1] 499, 501 | |
| I-9 | 4-cyanophenyl | Br | H | Me | Me | H, H | [M +1] 517, 519 | |
| I-10 | 4-acetamido-phenyl | Br | H | Me | Me | H, H | [M + 1] 549, 551 | |
| I-11 | 2-pyrrolyl | Br | H | Me | Me | H, H | [M + 1] 481, 483 | |
| I-12 | 4-imidazolinyl | Br | H | Me | Me | H, H | [M + 1] 482, 484 | |
| I-13 | 3-acetamido-phenyl | Br | H | Me | Me | H, H | [M + 1] 549, 551 | |
| I-14 | 3-fluoro-phenyl | Br | H | Me | Me | H, H | [M + 1] 510, 512 | |
| I-15 | 3-nitro-phenyl | Br | H | Me | Me | H, H | [M + 1] 537, 539 | |
| I-16 | 4-methanesulfonyl-phenyl | Br | H | Me | Me | H, H | [M + 1] 570, 572 | |
| I-17 | 2-chloro-4-methanesulfonyl-phenyl | Br | H | Me | Me | H, H | | 192.5-194.9 |
| I-18 | 4-nitro-phenyl | Br | H | Me | Me | H, H | [M + 1] 537, 539 | |
| I-19 | 2-cyano-phenyl | Br | H | Me | Me | H, H | [M + 1] 517, 519 | |
| I-20 | 3-cyano-phenyl | Br | H | Me | Me | H, H | [M + 1] 517, 519 | |
| I-21 | 2-chloro-4-sulfonamido-phenyl | Br | H | Me | Me | H, H | (ESI) 605, 607 | 223.1-224.0 |
| I-22 | 2-chloro-4-carboxy-phenyl | Br | H | Me | Me | H, H | APCI 570, 572 | 247.2-249.9 |
| I-23 | 2-chloro-sulfonamido-phenyl | H | H | Me | Me | H, H | 528.1 | |
| I-24 | 2-chloro-sulfonamido-phenyl | H | H | Cl | Me | H, H | 547.4 | |
| I-25 | 2-chloro-4-sulfonamido-phenyl | H | H | Cl | H | H, H | 533.2 | |
| I-26 | 4-carboxamido-2-chloro-phenyl | H | H | Me | Me | H, H | 491.3 | |
| I-27 | 2-chloro-4-methanesulfonyl-phenyl | H | H | Me | Me | H, H | 526.3 | |
| I-28 | 4-carboxamido-2-chloro-phenyl | Br | H | Me | Me | H, H | 569.4 | |
| I-29 | 2-chloro-4-cyano-phenyl | H | H | Me | Me | H, H | 473.2 | |
| I-30 | 2-chloro-4-cyano-phenyl | Br | H | Me | Me | H, H | 551.3 | |
| I-31 | 2,3-difluoro-phenyl | Br | H | Me | Me | H, H | 529.2 | |
| I-32 | 3-chloro-pyridin-4-yl | Br | H | Me | Me | H, H | 527.1 | |
| I-33 | 3-chloro-pyridin-4-yl | H | H | Me | Me | H, H | 449.2 | |
| I-34 | 4-tert-Bu-phenyl | Br | H | Me | Me | H, H | 548.3 | |
| I-35 | 3-trifluoromethyl-phenyl | Br | H | Me | Me | H, H | 560.2 | |
| I-36 | 4-(2-cyano-phenyl)-phenyl | Br | H | Me | Me | H, H | 593.3 | |
| I-37 | 4-trifluoromethoxy-phenyl | Br | H | Me | Me | H, H | 576.2 | |
| I-38 | 3-trifluoromethoxy-phenyl | Br | H | Me | Me | H, H | 576.3 | |
| I-39 | 3-chloro-phenyl | Br | H | Me | Me | H, H | 526.2 | |
| I-40 | 4-chloro-phenyl | Br | H | Me | Me | H, H | 526.2 | |
| I-41 | 2,4-di-trifluoromethyl-phenyl | Br | H | Me | Me | H, H | 628.3 | |
| I-42 | 3,5-dimethoxy-phenyl | Br | H | Me | Me | H, H | 552.3 | |
| I-43 | quinolin-8-yl | Br | H | Me | Me | H, H | 543.3 | |

TABLE I-continued

| Cpd. No. | R$^{1a}$ | R$^3$ | R$^4$ | R$^{5a}$ | R$^{5b}$ | R$^{6a}$, R$^{6b}$ | ms | mp |
| --- | --- | --- | --- | --- | --- | --- | --- | --- |
| I-44 | 3-chloro-4-fluoro-phenyl | Br | H | Me | Me | H, H | 544.2 | |
| I-45 | 3-chloro-pyridin-4-yl | Br | H | Me | Me | H, H | 448.3 | |
| I-46 | 4-carboxamido-2-chloro-phenyl | H | H | Me | Me | (CH$_2$)$_2$ | 517.4 | |
| I-47 | 2-chloro-4-methanesulfonyl-phenyl | H | H | Me | Me | (CH$_2$)$_2$ | 551.4 | |
| I-48 | 2-chloro-4-methanesulfonyl-phenyl | H | H | Cl | Me | H, H | 546.2 | |
| I-49 | 2-chloro-4-methanesulfonyl-phenyl | Br | H | Me | Me | (CH$_2$)$_2$ | 630.4 | |
| I-50 | 4-carboxamido-2-chloro-phenyl | Br | H | Me | Me | (CH$_2$)$_2$ | 595.4 | |
| I-51 | 2-chloro-4-methanesulfonyl-phenyl | Br | H | Cl | Me | H, H | 625.2 | |
| I-52 | 2-chloro-4-iso-propoxycarbonyl-phenyl | Br | H | Me | Me | H, H | 611.3 | |
| I-53 | 4-carboxamido-2-chloro-phenyl | H | H | Cl | Me | H, H | 511.2 | |
| I-54 | 4-pyrimidin-4-yl | Br | H | Me | Me | H, H | 494.3 | |
| I-55 | 2-chloro-4-methanesulfonyl-phenyl | CF$_3$ | H | Me | Me | H, H | 594.3 | |
| I-56 | phenyl | Br | H | Me | Me | (CH$_2$)$_2$ | 518.2 | |
| I-57 | 2-chloro-4-methanesulfonyl-phenyl | F | H | Me | Me | H, H | 544.3 | |
| I-58 | 2-chloro-4-methanesulfonyl-phenyl | Cl | H | Me | Me | H, H | 560.3 | |
| I-59 | 4-carboxamido-2-chloro-phenyl | Br | H | Cl | Me | H, H | 589.4 | |
| I-60 | 2-chloro-4-sulfonamido-phenyl | Br | H | Cl | Me | H, H | 625.4 | |
| I-62 | 4-Pyridine-N-oxide | Br | H | Cl | Me | H, H | [M + H] 529.0 531.0 | |
| I-61 | | | | | | | 506.2 | |

Compounds of the present invention can be substituted with both a bromine at the 5-position and an amino substituent at the 6 position of the pyrimidine ring (TABLE II). 4-Amino-6-chloro-2-(methylthio)-pyrimidine (18a, CAS Reg No. 1005-38-5, D. L. Anderson et al., U.S. Pub. No. 2005/0288502) is a convenient precursor for the amino substituted compounds. The electron-donating amino substituent attenuates the reactivity of a 2-chloro group. The thiomethyl substituent is a poorer leaving group than the 2-chloro substituent which results in selective introduction of the aryloxy moiety at the 4-position. After introduction of the 4-aryloxy substitutent, oxidation of the thiomethyl affords the highly labile methanesulfonyl group which is displaced selectively by the 4-amino-piperidine moiety as depicted in SCHEME B.

SCHEME B

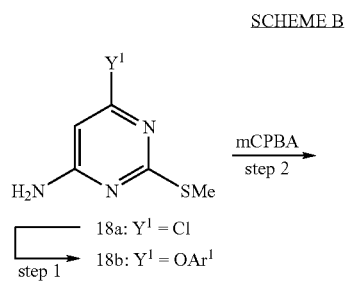

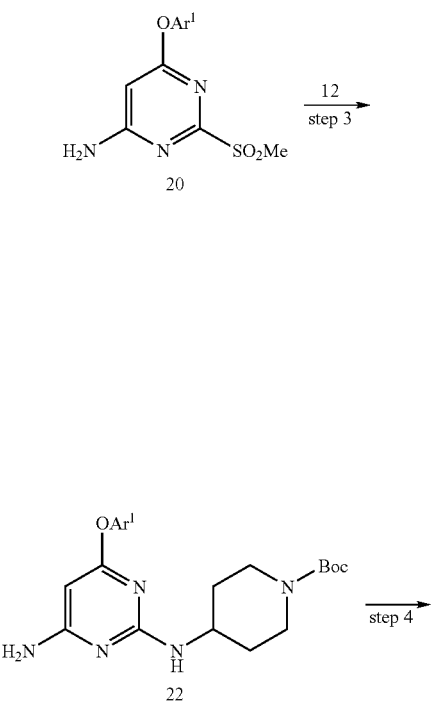

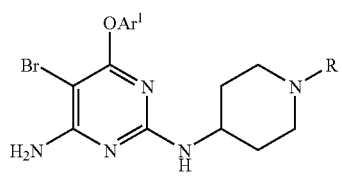

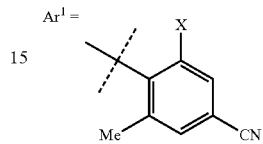

$Ar^1 =$

X = Me, Cl
$Ar^2 =$ optionally substituted phenyl or heteroaryl

Oxidation to the sulfone is readily accomplished with peroxy acids or with $MoO_5 \cdot HMPA \cdot H_2O$ (E. Vedejs et al., *J. Org, Chem.* 1978 43:188-196). Introduction of the 1-tert-butoxycarbonyl-4-aminopiperidine (step 3) and subsequent bromination (step 4) of the pyrimidine ring with NBS affords 24a. Deprotection (step 5) and alkylation of the piperidine nitrogen (step 6) is carried out as described above.

TABLE II

| Cpd. No. | Ar | ms | mp |
|---|---|---|---|
| II-1 | 2-chloro-4-sulfonamido-phenyl | 620.3 | |
| II-2 | 4-carboxamido-2-chloro-phenyl | 584.3 | |
| II-3 | 2-chloro-4-methanesulfonyl-phenyl | 619.3 | |

$N^2$-(1-Benzyl-piperidin-4-yl)-$N^4$-phenyl-pyrimidine-2,4-diamines are prepared from 4-chloro-2-methylthio-pyrimidine (CAS Reg No. 49844-90-8, J.-P. Roduit WO2000/063184) as depicted in SCHEME C. The reaction sequence parallels that described in SCHEME A except methylthio moiety is used initially to suppress reactivity at the 2 position during the first amination (step 1) then to activate the 2-position after the electron donating aryl amine is introduced at the 4 position. Oxidation of the sulfide (step 2), displacement of the 2 methylsulfonyl (step 3) with 1-tert-butoxycarbonyl-4-aminopiperidine, removal of the Boc group (step 4) and introduction of the optionally substituted benzyl moiety (step 5) is carried out as

SCHEME C

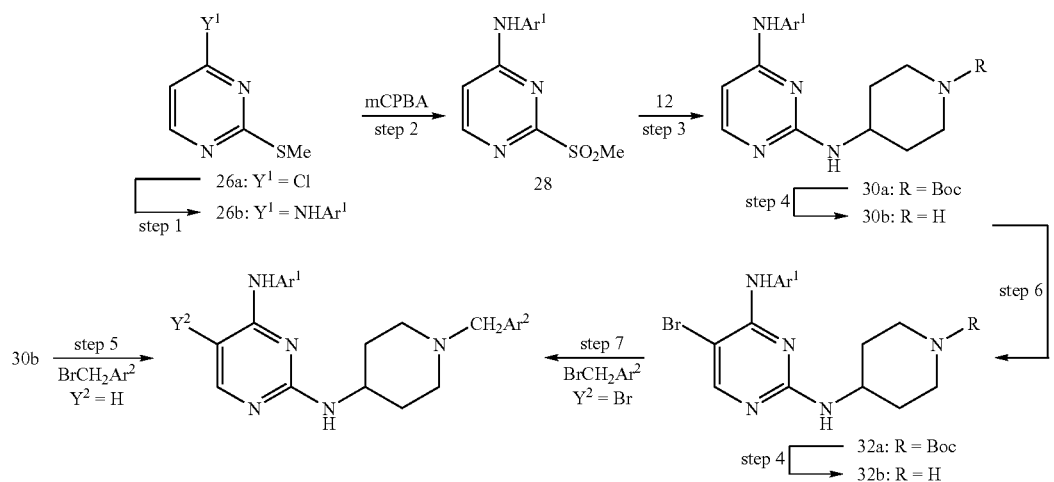

Ar¹, Ar² and X are as defined in SCHEME B described previously to afford 34 (Y²=H). In cases when it is advantageous to introduce a bromine at the 5-position of the pyrimidine ring, 30a is brominated with NBS (step 6) to afford 32a prior to deprotection and introduction of the optionally substituted benzyl group (steps 7 & 8).

TABLE III

| Cpd. No. | $R^{1a}$ | $R^2$ | $R^3$ | $R^{5a}$ | $R^{5b}$ | $R^{6a}, R^{6b}$ | ms |
|---|---|---|---|---|---|---|---|
| III-1 | 2-chloro-4-methanesulfonyl-phenyl | CN | H | Me | Me | H, H | 525.3 |
| III-2 | 2-chloro-4-sulfonamido-phenyl | CN | H | Me | Me | H, H | 526.3 |
| III-3 | 2-chloro-4-methanesulfonyl-phenyl | Br | Br | Me | Me | H, H | 656.3 |
| III-4 | 2-chloro-4-sulfonamido-phenyl | Br | H | Me | Me | H, H | 579.3 |
| III-5 | 2-chloro-4-methanesulfonyl-phenyl | CN | Br | Me | Me | H, H | 603.3 |
| III-6 | 4-carboxamido-2-chloro-phenyl | CN | H | Me | Me | H, H | 490.3 |
| III-7 | 4-carboxamido-2-chloro-phenyl | CN | Br | Me | Me | H, H | 568.2 |
| III-8 | 2-chloro-4-methanesulfonyl-phenyl | Br | H | Me | Me | H, H | 578.2 |
| III-9 | 2-chloro-4-methanesulfonyl-phenyl | CH=CHCN | H | Me | Me | H, H | 551.3 |
| III-10 | 4-carboxamido-2-chloro-phenyl | CH=CHCN | H | Me | Me | H, H | 516.5 |
| III-11 | 3-chloro-pyridin-4-yl | CN | Br | Me | Me | H, H | 526.3 |
| III-12 | 2-chloro-4-methanesulfonyl-phenyl | CN | H | Me | Me | $(CH_2)_2$ | 552.4 |
| III-13 | 2-chloro-4-iso-propoxycarbonyl-phenyl | CN | H | Me | Me | H, H | 533.4 |
| III-14 | 4-carboxyl-2-chloro-phenyl | CN | H | Me | Me | H, H | 491.3 |
| III-15 | 2-chloro-4-methanesulfonyl-phenyl | CN | Br | Cl | Me | H, H | 623.2 |
| III-16 | 2-chloro-4-methanesulfonyl-phenyl | CH=CHCN | Br | Me | Me | H, H | 629.4 |
| III-17 | 4-carboxy-2-chloro-phenyl | CN | Br | Me | Me | H, H | 569.3 |
| III-18 | 2-chloro-4-sulfonamido-phenyl | CN | H | Me | H | H, H | 513.2 |

TABLE III-continued

[Structure: R5b, R2, R5a, R3 substituted phenyl-NH-pyrimidine-NH-piperidine with R6a, R6b, R1a substituents]

| Cpd. No. | R1a | R2 | R3 | R5a | R5b | R6a, R6b | ms |
|---|---|---|---|---|---|---|---|
| III-19 | [3-Cl-4-(CONH(CH2)2NMe2)-phenyl-CH2*] | CN | Br | Me | Me | H, H | 639.2<br>641.2 |

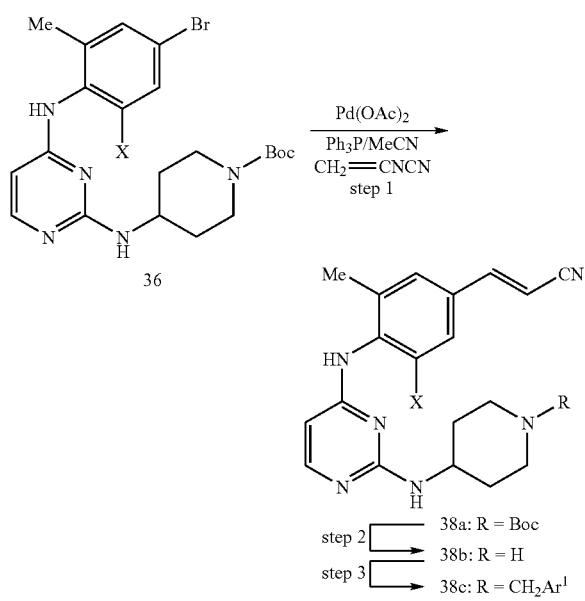

SCHEME D

38a: R = Boc
step 2 ↓
38b: R = H
step 3 ↓
38c: R = CH$_2$Ar$^1$

Ar$^1$ and X are as defined in SCHEME B

Compounds of the present invention containing an acrylonitrile substituent are prepared from 36 which is, in turn, prepared from 26a as described in SCHEME C except 4-bromo-2,6-dimethyl-phenylamine or 4-bromo-2-chloro-6-methyl phenyl-amine is used in place of 4-amino-3,5-dimethyl-benzonitrile to afford 38a. Coupling of acrylonitrile was accomplished using the Heck protocol (SCHEME D). The Heck reaction is a palladium-catalyzed cross-coupling or an alkenyl, aryl, alkynyl or benzyl halide or triflate and an olefin. (R. Heck, *Angew. Chem. Int. Ed.* 1995 33:2379; A. de Meijere and F. E. Meyer *Angew. Chem. Int. Ed.* 1994 33:2379-2411; W. Cabri and I. Candiani, *Acc. Chem. Res.* 1995 28:2-7). The olefin can be substituted with electron-donating or electron-withdrawing groups. A variety of palladium species can be utilized including, but not limited to Pd(OAc)$_2$ and Pd$_2$(dba)$_3$. Phosphine ligands are incorporated into the reaction mixture to solubilize Pd(0) and a range of bases are also added including, but not limited to NaHCO$_3$, K$_2$CO$_3$, Ag$_2$CO$_3$, Cs$_2$CO$_3$. The reaction is typically run in aprotic solvents, however, a wide range of solvent polarities are compatible with the reaction. The process is completed by removal of the Boc protecting group (step 2) and alkylation the piperidine nitrogen (step 3) as described previously.

TABLE IV

[Structure: NC-phenyl(R5a,R5b)-O-pyrimidine(R3,R4)-NH-piperidine-N-Ar]

| Cpd. No. | Ar | R3 | R4 | R5a | R5b | ms |
|---|---|---|---|---|---|---|
| IV-1 | phenyl | Br | H | Me | Me | [M + 1] = 478, 480 |

TABLE IV-continued

| ID | Substituent | | | | | MS |
|---|---|---|---|---|---|---|
| IV-2 | 4-sulfonamido-phenyl | H | H | Me | Me | 478.9 |
| IV-3 | 3-sulfonamido-phenyl | H | H | Me | Me | 478.9 |
| IV-4 | 3-cyano-phenyl | H | NH$_2$ | Me | Me | 440.3 |
| IV-5 | 3-cyano-phenyl | Br | H | Me | Me | 503.2 |
| IV-6 | 3-cyano-phenyl | H | H | Me | Me | 424.3 |
| IV-7 | 3-carboxamido-phenyl | H | H | Me | Me | 443.2 |
| IV-8 | 3-carboxamido-phenyl | Br | H | Me | Me | 521.3 |
| IV-9 | 3-methanesulfonyl-phenyl | Br | H | Me | Me | 556.2 |
| IV-10 | 3-methanesulfonyl-phenyl | H | H | Me | Me | 478.3 |
| IV-11 | 3-methanesulfonyl-phenyl | H | H | Cl | Me | 498.2 |
| IV-12 | 3-methanesulfonyl-phenyl | Br | H | Cl | Me | 576.3 |
| IV-13 | 3-carboxamido-phenyl | Br | H | Cl | Me | 541.2 |
| IV-14 | 3-carboxamido-phenyl | H | H | Cl | Me | 463.3 |
| IV-15 | 3-carboxamido-phenyl | F | H | Me | Me | 461.3 |
| IV-16 | 3-carboxamido-phenyl | Cl | H | Me | Me | 477.4 |
| IV-17 | 3-carboxamido-phenyl | CF$_3$ | H | Me | Me | 511.3 |
| IV-18 | 3-nitro-phenyl | H | H | Me | Me | 445.3 |
| IV-19 | 3-methanesulfonyl-phenyl | F | H | Me | Me | 496.3 |
| IV-20 | 3-methanesulfonyl-phenyl | Cl | H | Me | Me | 512.3 |
| IV-21 | 3-methanesulfonyl-phenyl | CF$_3$ | H | Me | Me | 546.3 |
| IV-22 | 3-chloro-5-cyano-phenyl | Br | H | Me | Me | 537.2 |
| IV-23 | 3-chloro-5-cyano-phenyl | H | H | Me | Me | 459.3 |
| IV-24 | 3-chloro-5-carboxamido-phenyl | Br | H | Me | Me | 555.2 |
| IV-25 | 3-chloro-5-carboxamido-phenyl | H | H | Me | Me | 477.3 |
| IV-26 | 2-carboxamido-phenyl | Br | H | Me | Me | 521.2 |
| IV-27 | 4-carboxamido-phenyl | Br | H | Me | Me | 521.2 |
| IV-28 | pyridin-3-yl | H | H | Cl | Me | 421.4 |
| IV-29 | pyrimidin-2-yl | H | H | Cl | Me | 422.4 |
| IV-30 | 3-(cyanomethyl)phenyl | H | H | Cl | Me | 459.4 |
| IV-31 | 3-amino-phenyl | Br | H | Cl | Me | 513.2 |
| IV-32 | 3-(N-methyl-carboxamido)phenyl | Br | H | Me | Me | 535.2 / 537.2 |
| IV-33 | 3-(N-cyclopropyl-carboxamido)phenyl | Br | H | Me | Me | 561.2 / 563.2 |
| IV-34 | 3-(N-2-hydroxy-ethyl-carboxamido)phenyl | Br | H | Me | Me | 565.2 / 567.2 |
| IV-35 | 3-(N-2-dimethylamino-ethyl-carboxamido)phenyl | Br | H | Me | Me | 592.3 / 594.3 |
| IV-36 | 3-(carboxamidomethyl)phenyl | Br | H | Me | Me | 535.3 / 573.4 |
| IV-37 | 3-(hydroxymethyl)phenyl | Br | H | Me | Me | 508.3 / 510.4 |
| IV-38 | 3-(NHSO$_2$Me)phenyl | Br | H | Me | Me | 571.2 / 573.1 |
| IV-39 | 3-(NHCOMe)phenyl | Br | H | Me | Me | 535.2 / 537.2 |
| IV-40 | 3-carboxamido-phenyl | Br | H | OMe | Me | [M + H] 537.3 / 539.3 |
| IV-41 | 3-(CONH(CH$_2$)$_2$NMe$_2$ methyl)phenyl | Br | H | Me | Me | 606.1 / 608.2 |

TABLE IV-continued

| | | | | | | |
|---|---|---|---|---|---|---|
| IV-42 | 3-(CO₂H-methyl)phenyl | Br | H | Cl | Me | 556.3 558.3 |
| IV-43 | 3-(CONHCHMeCH₂OH-methyl)phenyl | Br | H | Cl | Me | 612.2 614.2 |
| IV-44 | 3-(1,2-dihydroxyethyl)phenyl | Br | H | Me | Me | [M + H] 538.0 540.0 |
| IV-45 | 3-carboxamido-phenyl | Me | H | Me | Me | 457.2 |
| IV-46 | 3-(CONH₂-methyl)phenyl | Me | H | Cl | Me | [M + H] 491.2 |
| IV-48 | 3-(CONH₂-methyl)phenyl | Br | H | F | Me | [M + H] 525.3 527.3 |
| IV-49 | 3-(CONHSO₂Me-methyl)phenyl | Br | H | Me | Me | 612.9 614.9 |
| IV-50 | 3-aminosulfonyl-phenyl | Br | H | Me | Me | 557.1 559.1 |
| IV-58 | 4-carboxamido-pyridin-2-yl | CN | Br | H | Me | [M + H] 522.4 524.3 |
| IV-59 | 2-carboxamido-pyridin-6-yl | CN | Br | H | Me | [M + H] 522.3 524.3 |

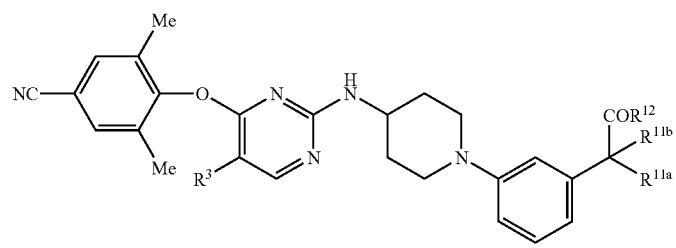

| | $R^3$ | $R^{11a}$ | $R^{11b}$ | $R^{12}$ | |
|---|---|---|---|---|---|
| IV-51 | Br | CH₂OH | H | OH | [M + H] 566.3 568.3 |
| IV-52 | Br | Me | H | OH | [M + H] 550.3 552.4 |
| IV-53 | Br | OMe | H | OH | [M + H] 566.7 568.7 |
| IV-54 | Br | OH | H | OH | [M + H] 551.9 553.9 |
| IV-55 | Br | F | F | OH | [M + H] 571.9 573.9 |

TABLE IV-continued

| IV-56 | Cl | OMe | H | OH | [M + H] 522.03 |
| IV-57 | Me | OMe | H | OH | [M + H] 502.1 |

Compounds of the present invention also can contain an optionally substituted 1-phenyl- or 1-heteroaryl-piperidin-4-ylamine substituent in place of the 1-benzyl-piperidin-4-ylamine (TABLES IV and V). The aryl or heteroaryl substituent typically is introduced onto the piperidine ring prior to incorporation onto the pyrimidine core. 1-Phenyl-piperidin-4-ylamines can be prepared by two methods. Fluoroaromatic compounds with electronegative substituents (40, R=electron-withdrawing group) undergo a direct $S_NAR$ displacement of the fluorine atom by piperidin-4-yl-carbamic acid tert-butyl ester (Method A, SCHEME E). Fluorine substituents are generally significantly more labile than other halogen substituents. While hard nucleophiles like water and hydroxide fail to displace fluoride, soft nucleophiles like phenols, imidazoles, amines, thiols and some amides undergo facile displacement reactions even at room temperature (D. Boger et al., Biorg. Med. Chem. Lett. 2000 10:1471-75; F. Terrier Nucleophilic Aromatic Displacement: The Influence of the Nitro Group VCH Publishers, New York, N.Y. 1991). Removal of the protecting group (step 3) affords the requisite 1-phenyl-piperidin-4-ylamine 44b. Alternatively, the displacement of iodo- or chlorobenzene compounds substituted with non-activating substituents is catalyzed by Cu(I) salts (Method B, SCHEME E) (J. Lindley, Tetrahedron 1984 40:1433-1456; J. Hassan et al., Chem. Rev. 2002 102:1359; D. Ma et al., J. Org. Chem. 2005 70:5164-5173).

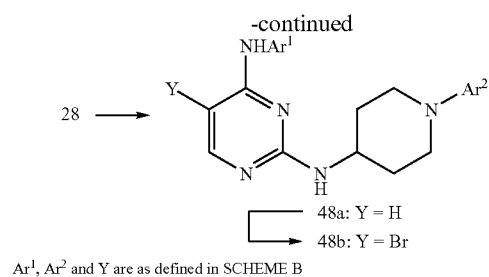

$Ar^1$, $Ar^2$ and Y are as defined in SCHEME B

The 1-(hetero)aryl-piperidin-4-yl amine was introduced into the pyrimidine using reaction sequences analogous to those exemplified in SCHEMES A and C for the corresponding benzyl derivatives in TABLES IV and V. Thus the 4-aryloxy compounds were prepared from 10b or 4-arylamines were prepared from 28. Incorporation of the acrylonitrile side chain was accomplished by treating 50a with acrylonitrile under Heck coupling conditions.

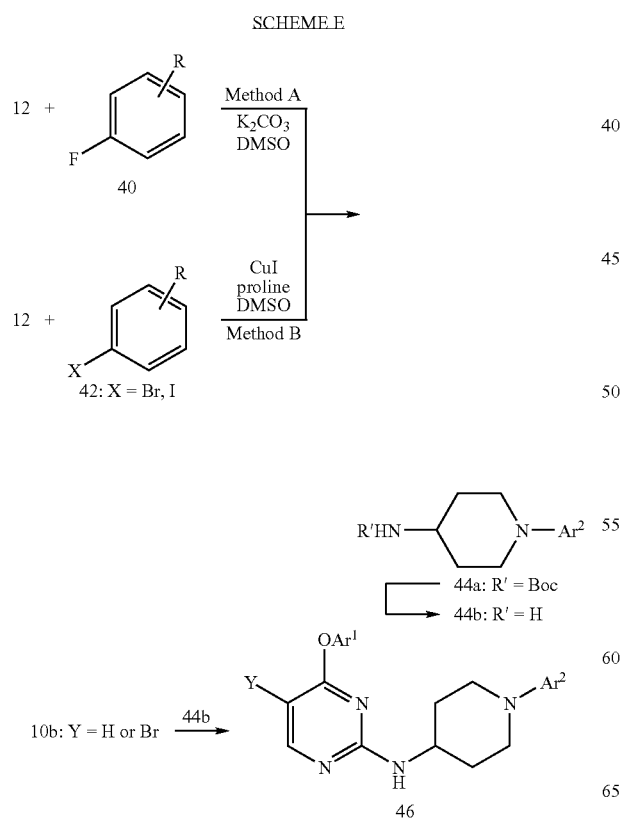

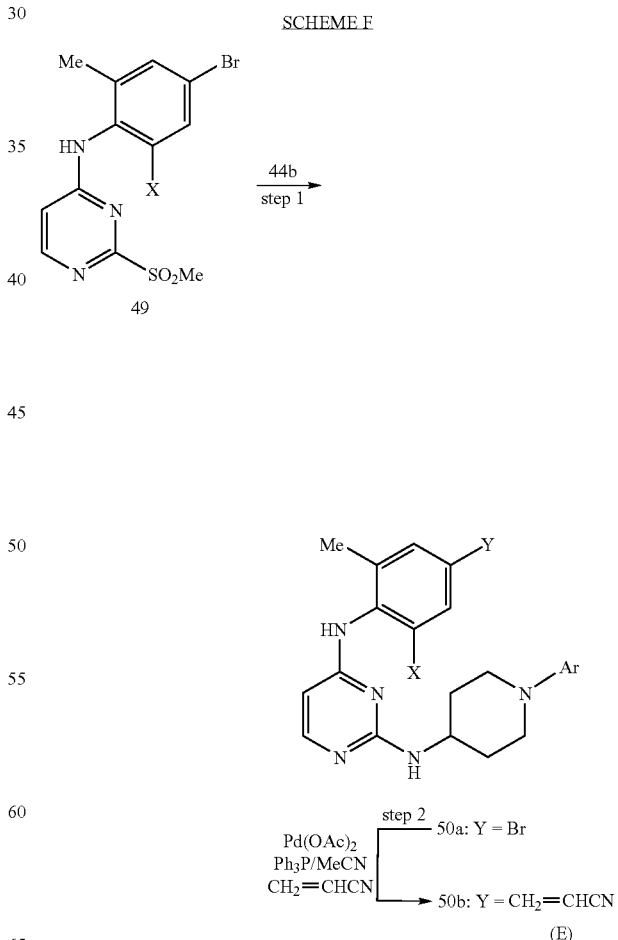

Ar = optionally substituted phenyl
X = Me or Cl

TABLE V

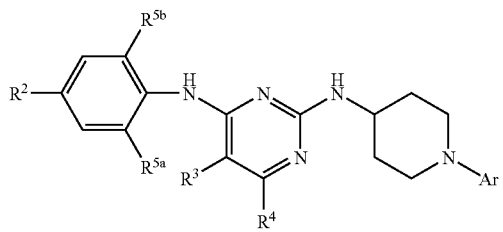

| Cpd. No. | Ar | $R^2$ | $R^3$ | $R^4$ | $R^{5a}$ | $R^{5b}$ | ms |
|---|---|---|---|---|---|---|---|
| V-1 | 3-cyano-phenyl | CN | H | H | Me | Me | 424.3 |
| V-2 | 2-bromo-5-cyano-phenyl | CN | Br | H | Me | Me | 581.3 |
| V-3 | 3-cyano-phenyl | CN | Br | H | Me | Me | 503.3 |
| V-4 | 3-carboxamido-phenyl | CN | H | H | Me | Me | 442.3 |
| V-5 | 3-carboxamido-phenyl | CN | Br | H | Me | Me | 520.3 |
| V-6 | 3-methanesulfonyl-phenyl | Br | H | H | Me | Me | 530.2 |
| V-7 | 3-carboxamido-phenyl | CH=CHCN | H | H | Me | Me | 468.5 |
| V-8 | 3-carboxamido-phenyl | CH=CHCN | H | H | Cl | Me | 488.5 |
| V-9 | 3-carboxamido-phenyl | CN | H | H | Cl | Me | 462.2 |
| V-10 | 5-(methoxy-carbonyl)-pyridin-3-yl | CN | H | H | Me | Me | 458.4 |
| V-11 | 5-carboxy-pyridin-3-yl | CN | H | H | Me | Me | 444.4 |
| V-12 | pyridin-3-yl | CN | H | H | Me | Me | 400.5 |
| V-13 | pyrimidin-2-yl | CN | H | H | Me | Me | 401.4 |
| V-14 | pyrimidin-2-yl | CN | Br | H | Me | Me | 479.4 |
| V-15 | pyrimidin-5-yl | CN | Br | H | Me | Me | 479.4 |
| V-16 | 3-amino-phenyl | CN | $NH_2$ | H | Me | Me | [M + H] 429.4 |
| V-17 | 3-(cyanomethyl)-phenyl | CN | H | H | Me | Me | [M + H] 438.3 |
| V-18 | 3-carboxamido-phenyl | CN | Br | H | F | Cl | [M + H] 544.0 546.0 |
| V-19 | 3-(N,N-dimethylcarboxamido-methyl)-phenyl | CN | Br | H | Me | Me | 562.2 534.2 |

Dosage and Administration

The compounds of the present invention may be formulated in a wide variety of oral administration dosage forms and carriers. Oral administration can be in the form of tablets, coated tablets, dragees, hard and soft gelatine capsules, solutions, emulsions, syrups, or suspensions. Compounds of the present invention are efficacious when administered by other routes of administration including continuous (intravenous drip) parenteral, intramuscular, intravenous, and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. N-acylsulfonamides have an acidic proton which can be abstracted to form a salt with an organic or inorganic cation.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia.

Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The status of an HIV infection can be monitored by measuring viral load (RNA) or monitoring T-cell levels. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

These examples and preparations that follow are provided to enable those skilled in the art to more clearly understand and to practice the present invention. They should not be

Example 1

4-[2-(1-Benzyl-piperidin-4-ylamino)-5-bromo-pyrimidin-4-yloxy]-3,5-dimethyl-benzonitrile (I-2)

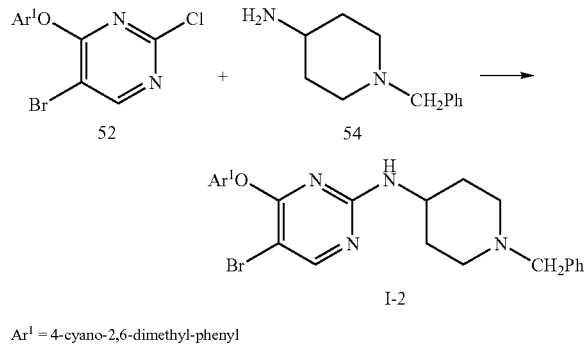

Ar¹ = 4-cyano-2,6-dimethyl-phenyl

1-Benzyl-piperidin-4-ylamine (0.5 mL, 2.5 mmole, CASRN 50541-93-0), DIPEA (2.8 mL, 16 mmol) and 4-(5-bromo-2-chloro-pyrimidin-4-yloxy)-3,5-dimethylbenzonitrile (52, 0.54 g, 1.6 mmol) were combined in NMP (30 mL) and warmed at 100° C. for 3 h. The crude reaction mixture was cooled, poured into water and brine. The resulting white solid was filtered, washed with water and dried under vacuum. Recrystallization from EtOAc/hexanes afforded 620 mg of I-2 as a white solid: H-NMR (DMSO): δ 8.29 (s, 1H), 7.58 (s, 2H), 7.26 (m, 5H, phenyl), 6.98 (br.d, 1H, NH), 3.40 (s, 2H), 2.68 (m, 2H), 2.13 (s, 6H), 2.03 (m 2H), 1.81 (m 2H), 1.38 (m, 2H); mp 158.0-159.8° C.; ms (ESI) M=492, 494.

4-[2-(1-Benzyl-piperidin-4-ylamino)-pyrimidin-4-yloxy]-3,5-dimethyl-benzonitrile (I-1) was prepared analogously except 52 was replaced with 4-(2-chloro-pyrimidin-4-yloxy)-3,5-dimethyl-benzonitrile (68a).

4-[5-Bromo-2-(1-phenyl-piperidin-4-ylamino)-pyrimidin-4-yloxy]-3,5-dimethyl-benzonitrile (IV-1) was prepared analogously except 54 was replaced with 1-phenyl-piperidin-4-ylamine (CASRN 63921-23-3).

Example 2

N-(3-{4-[5-Bromo-4-(4-cyano-2,6-dimethylphenoxy)-pyrimidin-2-ylamino]-piperidin-1-ylmethyl}-phenyl)-acetamide (I-13)

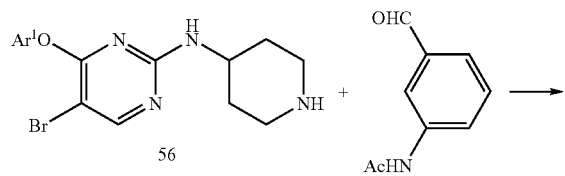

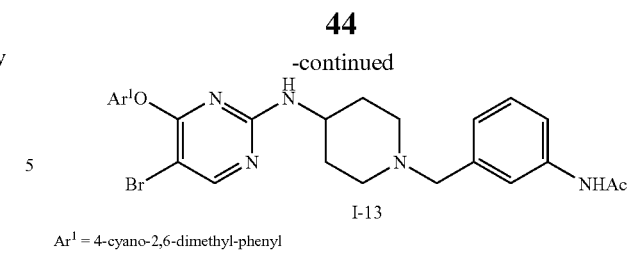

Ar¹ = 4-cyano-2,6-dimethyl-phenyl

4-[5-Bromo-2-(piperidin-4-ylamino)pyrimidin-4-yloxy]-3,5-dimethyl-benzonitrile (56, 17 mg, 0.042 mmol) and N-(3-formyl-phenyl)-acetamide (8.2 mg, 0.05 mmol) were combined in MeOH (0.3 mL) with 1 drop of HOAc. To the resultant solution was added a slurry of PL-cyanoborohydride resin (42 mg, 0.8 mmol) in 0.2 mL of DCM. After stirring at RT for 24 h, the resin was filtered off and washed 3 times with DCM. The combine filtrate and washes were concentrated in vacuo and the resultant residue purified by reverse phase HPLC (10 to 90% MeCN: 0.1% aqueous TFA buffered gradient) to afford 18.6 mg of I-13 as the TFA salt: M+H=549, 551.

The following were prepared analogously except N-(3-formyl-phenyl)-acetamide was replaced by the aldehyde in parenthesis: I-4 (4-formyl-benzoic acid), I-5 (pyridine-4-carbaldehyde), I-6 (thiophene-2-carbaldehyde), I-7 (thiophene-3-carbaldehyde), I-8 (thiazole-2-carbaldehyde), I-9 (4-formyl-benzonitrile), I-10 (N-(4-formyl-phenyl)-acetamide), I-11 (pyrrole-2-carbaldehyde), I-12 (3H-imidazole-4-carbaldehyde), I-14 (3-fluoro-benzaldehyde) and I-15 (3-nitrobenzaldehyde).

Example 3

4-{2-[1-(4-Methanesulfonyl-benzyl)-piperidin-4-ylamino]-pyrimidin-4-yloxy}-3,5-dimethyl-benzonitrile (I-3)

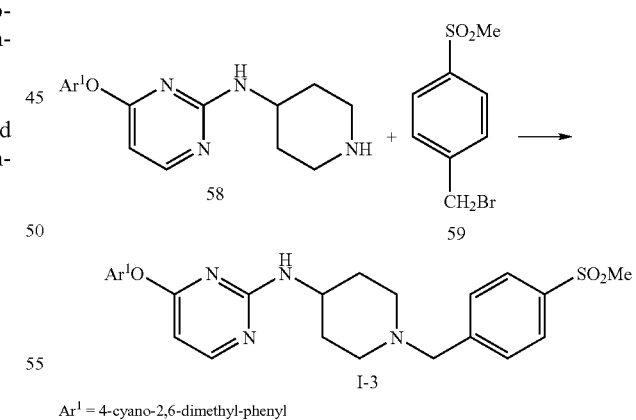

Ar¹ = 4-cyano-2,6-dimethyl-phenyl

A mixture of 58 (100 mg, 0.31 mmole), DIPEA (0.55 mL, 3.1 mmol) and 1-bromomethyl-4-methanesulfonyl-benzene (120 mg, 0.48 mmol) in NMP (8 mL) was warmed at 100° C. for 3 h. The reaction mixture was partitioned into 3:2 EtOAc/hexanes, concentrated in vacuo and purified by SiO₂ chromatography eluting with 1:50:50 TEA/acetone/hexanes to afford 98 mg of I-3 as a tan solid: H-NMR (DMSO): 8.13 (d, 1H), 7.87 (d, 2H), 7.51 (d, 2H), 7.37 (s, 2H), 6.12 (d, 1H), 4.85

(br.d, 1H, NH), 3.54 (s, 2H), 3.03 (s, 3H), 2.71 (m, 2H), 2.13 (s, 6H), 2.03 (m 2H), 1.83 (m, 2H), 1.49 (m, 2H); ms (ESI) M=491.

Example 4

4-{5-Bromo-2-[1-(4-methanesulfonylbenzyl)-piperidin-4-ylamino]-pyrimidin-4-yloxy}-3,5-dimethyl-benzonitrile (I-16)

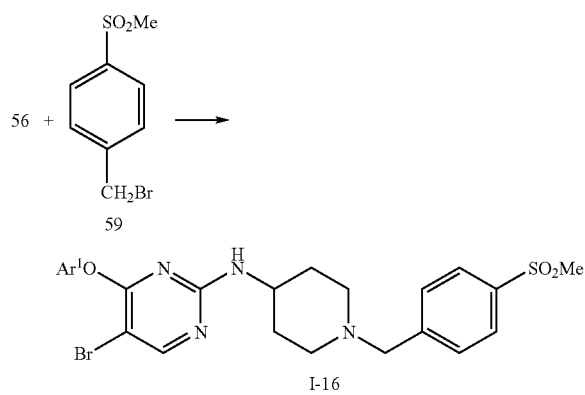

Ar¹ = 4-cyano-2,6-dimethyl-phenyl

4-[5-Bromo-2-(piperidin-4-ylamino)pyrimidin-4-yloxy]-3,5-dimethyl-benzonitrile (20 mg, 0.050 mmol), DIPEA (0.025 mL) and 59 (14 mg, 0.055 mmol) were combined in 0.5 mL of DMF and stirred at 25° C. for 24 h. Purification by reverse phase HPLC (10 to 90% MeCN/0.1% aqueous TFA buffer gradient) afforded 24.4 mg of I-16 as the TFA salt: M+H=570, 572.

The following were prepared analogously except 59 was replaced by the benzyl bromide in parenthesis: I-17 (4-bromomethyl-2-chloro-1-methanesulfonyl-benzene), I-18 (4-bromomethyl-1-nitro-benzene), I-19 (2-bromomethyl-benzonitrile), I-20 (3-bromomethyl-benzonitrile), I-21 (4-bromomethyl-3-chloro-benzenesulfonamide) and I-22 (4-bromomethyl-3-chloro-benzoic acid methyl ester was condensed with 56 and the ester was hydrolyzed with LiOH in aqueous THF), I-54 (4-bromomethyl-pyrimidine).

I-53 was prepared analogously except 56 was replaced with 3-chloro-5-methyl-4-[2-(piperidin-4-ylamino)-pyrimidin-4-yloxy]-benzonitrile and 59 was replaced 4-bromomethyl-3-chloro-benzamide.

I-51, I-59 and I-60 were prepared analogously except 56 was replaced with 4-[5-bromo-2-(piperidin-4-ylamino)-pyrimidin-4-yloxy]-3-chloro-5-methyl-benzonitrile and 59 was replaced with 1-bromomethyl-2-chloro-4-methanesulfonyl-benzene, 4-bromomethyl-3-chloro-benzamide and 4-bromomethyl-3-chloro-benzenesulfonamide respectively.

Example 5

3-Chloro-4-{2-[1-(2-chloro-4-methanesulfonyl-benzyl)-piperidin-4-ylamino]-pyrimidin-4-yloxy}-5-methyl-benzonitrile (I-48)

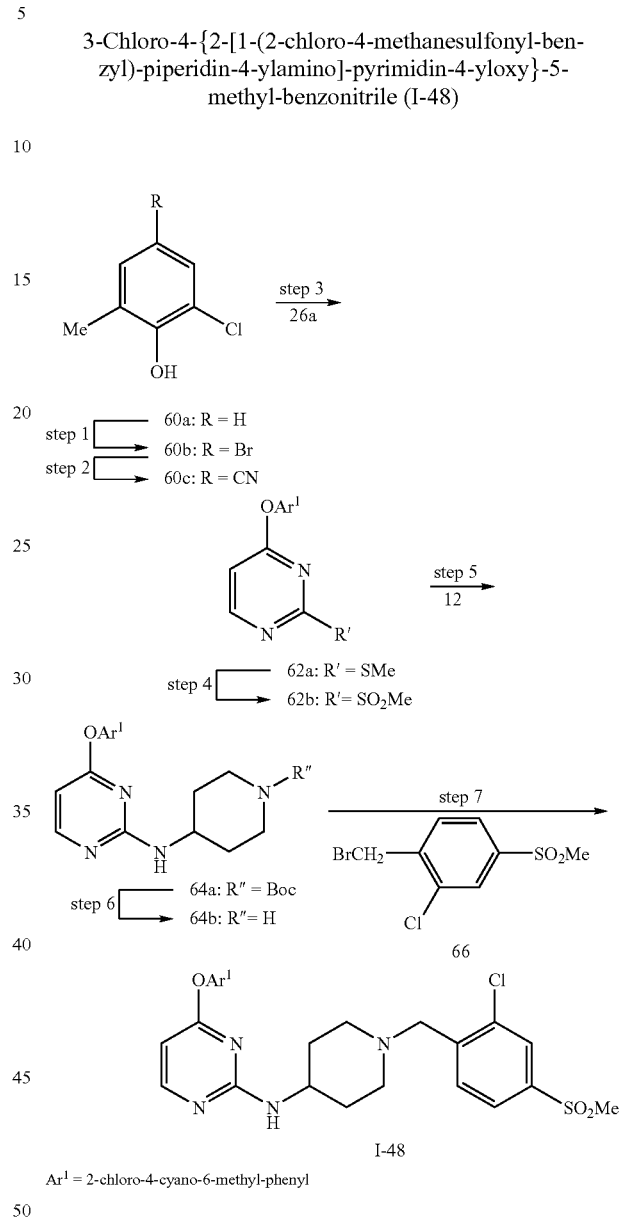

Ar¹ = 2-chloro-4-cyano-6-methyl-phenyl step 1—NBS (100 mmol) was added to a mixture of 60a (100 mmol) in HOAc (200 mL) and the mixture was stirred at RT overnight. The HOAc was removed and the residue was diluted with EtOAc and washed with saturated $Na_2CO_3$. The combined organic phase was dried ($Na_2SO_4$), filtered and evaporated to afford 60b as white solid that was used without further purification.

step 2—3-chloro-4-hydroxy-5-methyl-benzonitrile (60c) can be prepared from 60b as described by G. D. Diana and T. J. Nitz in U.S. Pat. No. 5,464,848.

step 3—To a solution of 60c (6.9 mmol) in NMP (10 mL) was added portion wise NaH (7.3 mmol) and the mixture was stirred at RT for 30 min. To the resulting solution was added 26a (7.3 mmol) and the reaction mixture was stirred at 140° C. in microwave for 3 h. The reaction mixture was cooled and partitioned between water and EtOAc. The aqueous layer was extracted with EtOAc. The combined extracts were washed with brine, dried (Na₂SO₄), filtered and evaporated to afford 62a that was used in the next step without purification.

step 4—MCPBA (6 mmol) was added portion wise to a solution of 62a (6.9 mmol) in DCM (30 mL) cooled to 0° C. After the reaction mixture was warmed to RT and stirred for 3 h. The reaction mixture was quenched with NaHSO₃, diluted with DCM and washed with saturated Na₂CO₃, water and brine. The organic phase was dried (Na₂SO₄) and the solvent was evaporated. The residue was purified by SiO₂ column chromatography eluting with EtOAc/hexane (2:1) to afford intermediate 1.8 g (83% for 2 steps) of 62b.

step 5—A mixture of 62b (3.8 mmol) and 12 (4.2 mmol) in NMP (10 mL) was stirred at 120° C. for 2 h. The reaction mixture was concentrated and purified by preparative HPLC eluting with MeCN/H₂O to afford 0.600 g (36%) of 64a as white solid.

step 6—Trifluoroacetic acid (0.5 mL) was added to a solution of 64a (0.47 mmol) in DCM (10 mL) at RT. The mixture was stirred at RT overnight. The solvent was removed to afford 0.400 g (100%) of 64b that was used without further purification.

step 7—A mixture of 64b (0.175 mmol), 66 (0.175 mmol, CASRN 180200-86-6) and TEA (0.2 mL) in NMP (1 mL) was stirred at RT for 2 h. The reaction mixture was purified by preparative HPLC eluting with MeCN/H₂O to afford 0.078 g (82%) of I-48 as white solid.

I-26 was prepared analogously except in step 3, 60c was replaced by 3,5-dimethyl-4-hydroxy-benzonitrile (CASRN 4198-90-7) and in step 7, 1-bromomethyl-2-chloro-4-methanesulfonyl-benzene was replaced with 4-bromomethyl-3-chlorobenzamide (prepared by NBS bromination of 3-chloro-4-methyl-benzamide, CASRN 24377-95-5).

I-27 was prepared analogously except in step 3, 60c was replaced with 3,5-dimethyl-4-hydroxy-benzonitrile (70, CASRN 4198-90-7).

I-29 was prepared analogously except in step 3, 60c was replaced by 70 and in step 7, 1-bromomethyl-2-chloro-4-methanesulfonyl-benzene was replaced with 4-bromomethyl-3-chloro-benzonitrile.

Example 6

3-Chloro-4-{4-[4-(4-cyano-2,6-dimethyl-phenoxy)-pyrimidin-2-ylamino]-piperidin-1-ylmethyl}-benzenesulfonamide (I-23)

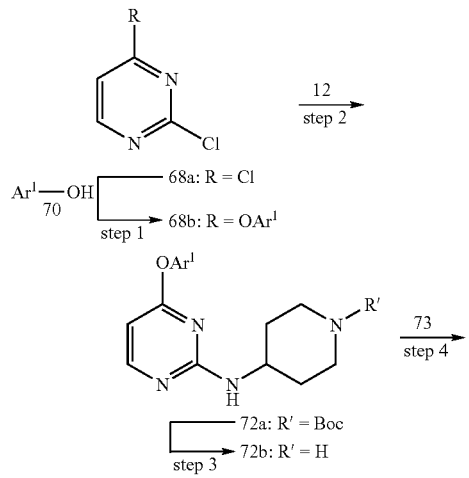

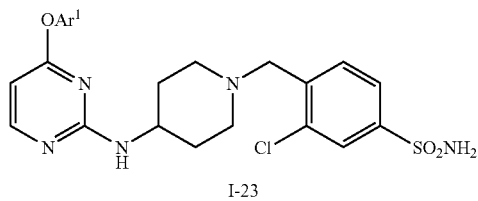

I-23

Ar¹ = 4-cyano-2,6-dimethyl-phenyl step 1—Sodium hydride (1 mmol, 60% in oil) was added in portion to a solution of 70 in THF at RT. The resulting solution was stirred for 10 min, then 2,4-dichloropyrimidine (1 mmol, CAS Reg No. 3934-20-1) was added. The reaction mixture was stirred for 6 h at RT. After the reaction was complete the solvent was removed in vacuo to afford 0.230 g (88.8%) of 68b which was used directly in next step.

step 2—A mixture of 68b (1 mmol) and 12 (1 mmol) was fused at 150° C. for 2 h. The reaction mixture was cooled and purified by SiO₂ chromatography eluting with EtOAc/hexane (1:2) to afford 0.210 g (49.6%) of 72a.

step 3—To a solution of 72a (1 mmol) in DCM was added TFA (1 mL), the resulting solution was stirred at RT for 5 h. After the reaction was complete the solvents were removed in vacuo to afford 0.460 g (100%) of the TFA salt of 72b as a yellow oil which was used in the next step without purification.

step 4—To a solution of 72b (0.2 mmol) in MeCN was added TEA (0.3 mmol) and 73 (0.2 mmol) and the resulting mixture was stirred at RT for 6 h. After the reaction was complete, the solvent was evaporated and the residue purified by preparative HPLC on a 30×100 mm C18 ORB column eluting with MeCN/H₂O to afford 0.023 g (22%) of I-23.

Preparation of 4-bromomethyl-3-chloro-benzenesulfonamide (73)

The title compound was prepared by NBS/AIBN mediated bromination of 3-chloro-4-methyl-benzenesulfonamide (CASRN 51893-27-6, R. Wigwag et al., U.S. Publication No. 20050282793).

Example 7

3-Chloro-4-{4-[4-(2-chloro-4-cyano-phenoxy)-pyrimidin-2-ylamino]-piperidin-1-ylmethyl}-benzenesulfonamide (I-25)

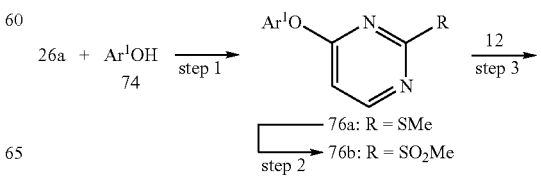

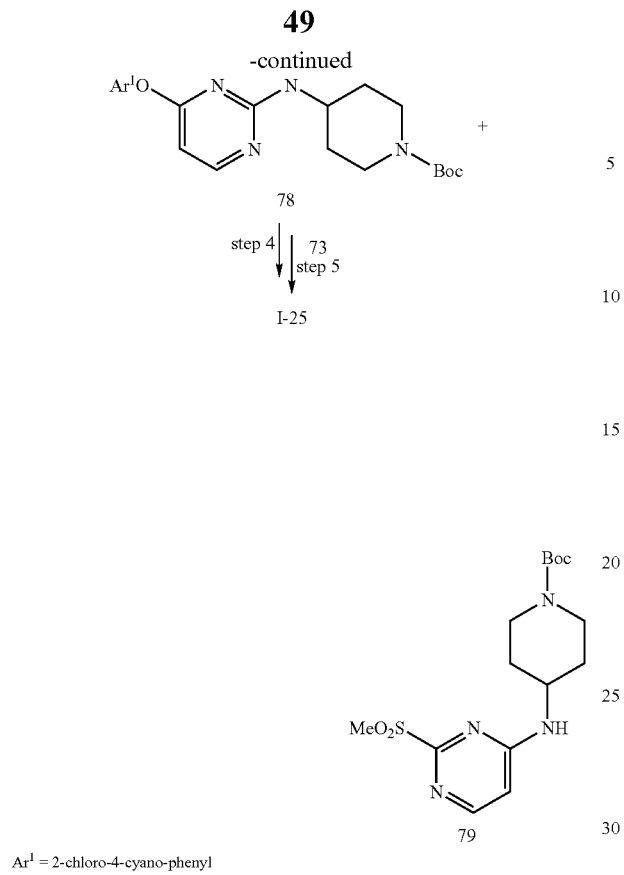

Ar¹ = 2-chloro-4-cyano-phenyl step 1—Sodium hydride (1 mmol, 60% in oil) was added in portion to a solution of 74 (1 mmol) in NMP at RT. The resulting solution was stirred for 5 min, and then 26a (1 mmol) was added. The reaction mixture was stirred for 30 min at 150° C. in a microwave. After the reaction was complete, EtOAc and H₂O were added and the aqueous phase was extracted with EtOAc. The organic extracts were dried (Na₂SO₄), filtered and the solvent was evaporated to afford 0.234 g (84.4%) of 76a which was used in the next step without purification.

step 2—To a solution of 76a (1 mmol) in DCM was added MCPBA (4 mmol) and the resulting mixture was stirred at RT for 4 h. After the reaction was complete, the reaction mixture was washed sequentially with saturated NaHSO₃ and saturated NaHCO₃ solution. The organic phase was dried (Na₂SO₄) and concentrated in vacuo to afford 0.304 g (98%) of 76b.

step 3—To a solution of 76b (1 mmol) in NMP was added 12 (1 mmol) and the resulting mixture was stirred at 150° C. for 30 min. After the reaction was complete, the resulting mixture of 78 and the by-produce from displacement at the 4-position 79 was purified by SiO₂ column chromatography eluting with EtOAc/hexane (1:2) to afford 0.107 g (24.5%) of 78.

step 4—To a solution of 78 (0.2 mmol) in DCM was added TFA (1 mL) and the resulting solution was stirred at RT for 5 h. After the reaction was completed, the solvents were concentrated in vacuo to afford 0.098 g (100%) of a yellow oil which was directly used the next step without purification.

step 5—To a solution of secondary amine from step 4 (0.1 mmol) in MeCN was added Et₃N (0.3 mmol) and 73 and the reaction was stirred at RT for 3 h. The solvent was evaporated and the residue was purified by preparative HPLC by preparative HPLC on a 30×100 mm C18 ODB column eluting with MeCN/H₂O to afford 0.006 g (11%) of I-25.

Example 8

3-Chloro-4-{(1R,5S)-3-[4-(4-cyano-2,6-dimethyl-phenoxy)-pyrimidin-2-ylamino]-8-aza-bicyclo[3.2.1]oct-8-ylmethyl}-benzamide (I-46)

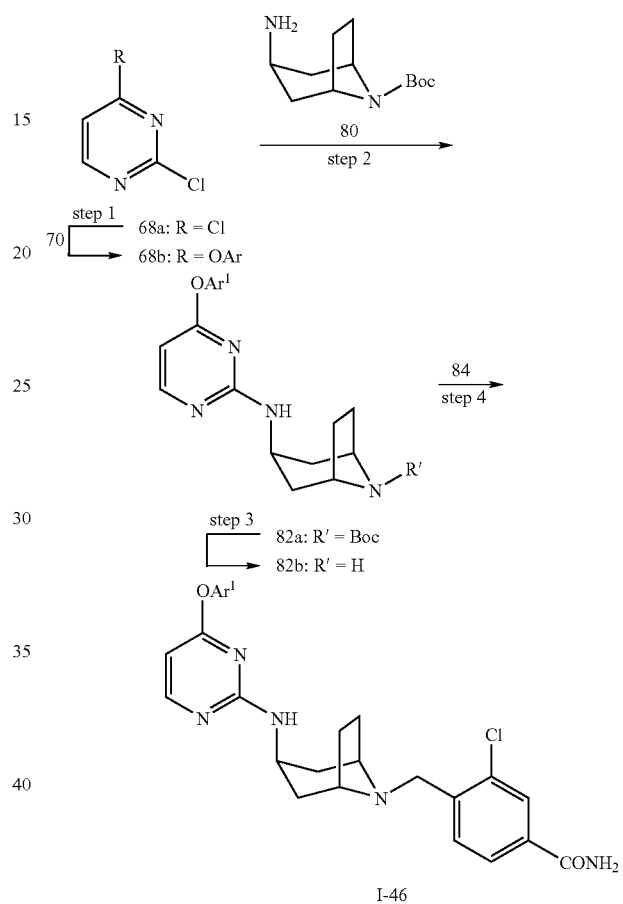

Ar¹ = 4-cyano-2,6-dimethyl-phenyl

3-Amino-8-aza-bicyclo[3.2.1]octane-8-carboxylic acid tert-butyl ester 80 was prepared by the procedure of D. Marquess et al. disclosed in WO2005/080389.

Preparation of 4-bromomethyl-3-chloro-benzamide (84)

A mixture of 3-chloro-4-methyl-benzamide (388 mg, 2.288 mmol, CASRN 24377-95-5)), NBS (456 mg, 2.564 mmol) and AIBN (100 mg) in CCl₄ (20 mL) was heated at reflux for 4 h at which time TLC analysis indicated the reaction complete. The reaction mixture was concentrated in vacuo to afford 0.426 g (75%) of without purification for the next step.

step 1—A mixture of 70 (10 mmol), 68a (10 mmol) and K₂CO₃ (15 mmol) in DMF (20 mL) was stirred at RT for 6 h. The mixture was poured into water (50 mL) and extracted with EtOAc. The organic phase was washed with brine, dried (Na₂SO₄), filtered and evaporated. The residue containing 68b was used in the next step without purification.

step 2—A mixture of 68b (2 mmol) and 80 (2 mmol) in n-BuOH was heated in a sealed tube at 160° C. for 6 h. When no starting material was detected by TLC, the reaction was cooled to RT and concentrated in vacuo. The crude product 82a was used in the next step without further purification.

step 3—TFA (2 mL) was added to a solution of 82a (1 mmol) in DCM (10 mL) at RT. The mixture was stirred at RT overnight and the solvent was evaporated to afford 0.349 g (100%) of 82b.

step 4—A mixture of 82b (1 mmol), 84 (1 mmol) and TEA (0.1 mL) in MeCN (2 mL) was stirred at RT overnight. The reaction mixture was purified by preparative HPLC on a 30×100 mm C18 ODB column eluting with MeCN/H$_2$O to afford 0.0424 g (82%) of I-46.

I-47 was prepared analogously except in step 4, 4-bromomethyl-3-chlorobenzamide was replaced with 4-bromomethyl-3-chloro-benzenesulfonamide.

I-49, I-50 and I-56 were prepared analogously except in step 1, 68a was replaced with 5-bromo-2,4-dichloro-pyrimidine and, in the preparation of I-49 and I-56, in step 4, 4-bromomethyl-3-chlorobenzamide was replaced with 1-bromomethyl-2-chloro-4-methanesulfonyl-benzene and benzyl bromide respectively.

Example 9

4-{2-[1-(2-Chloro-4-methanesulfonyl-benzyl)-piperidin-4-ylamino]-5-trifluoromethyl-pyrimidin-4-yloxy}-3,5-dimethyl-benzonitrile (I-55)

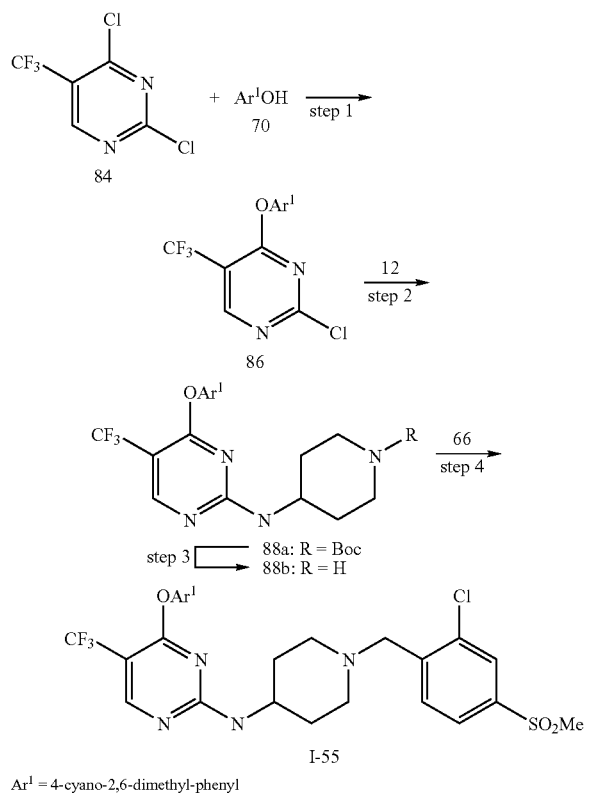

Ar$^1$ = 4-cyano-2,6-dimethyl-phenyl step 1—A mixture of 84 (20 mg, 0.922 mmol, CASRN 3932-97-6), 70 (176 mg, 1.2 mmol), K$_2$CO$_3$ (1.27 g, 9.22 mmol) in DMF (20 mL) was stirred at RT overnight. The reaction mixture was poured into H$_2$O (20 mL) and extracted with EtOAc (3×10 mL). The combined organic extracts were dried (Na$_2$SO$_4$), filtered and concentrated in vacuo to afford 0.2387 g (79%) of 86.

step 2—A mixture of the 86 (200 mg, 0.61 mmol) and 12 (147 mg, 0.73 mmol) was heated to 150° C. overnight. The reaction mixture was purified by preparative HPLC on a 30×100 mm C18 ODB column eluting with MeCN/H$_2$O to afford 0.182 g (61%) of 88a as white solid.

step 3—TFA (2 mL) was added to a solution of 88a (0.1 mmol) in DCM (10 mL) at RT and stirred overnight. The solvent was removed to afford 0.0392 g (100%) of 88b which was used without additional purification.

step 4—A mixture of 88b (0.1 mmol), 66 (0.1 mmol) and TEA (0.1 mL) in MeCN (2 mL) was stirred at RT overnight. The reaction mixture was purified by preparative HPLC on a 30×100 mm C18 ODB column eluting with MeCN/H$_2$O to afford 0.0487 g (82%) of I-55.

Example 10

4-{2-[1-(2-Chloro-4-methanesulfonyl-benzyl)-piperidin-4-ylamino]-5-fluoro-pyrimidin-4-yloxy}-3,5-dimethyl-benzonitrile (I-57)

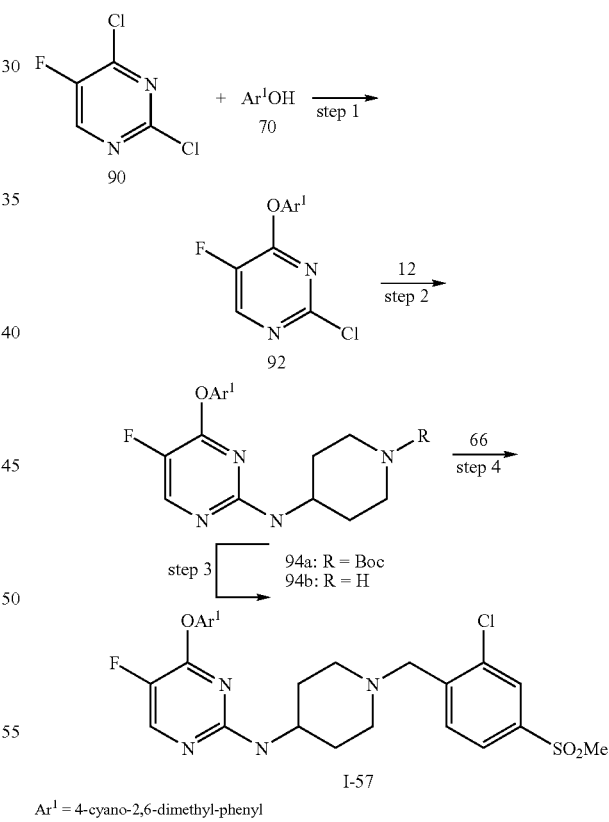

Ar$^1$ = 4-cyano-2,6-dimethyl-phenyl step 1—A mixture of 90 (500 mg, 2.99 mmol, CASRN 2927-71-1), 70 (485 mg, 3.3 mmol) and K$_2$CO$_3$ (1.24 g, 9 mmol) in DMF (20 mL) was stirred at RT overnight. The reaction mixture was poured into water (20 mL) and extracted with EtOAc (3×10 mL). The combined organic extracts were dried (Na$_2$SO$_4$), filtered and concentrated in vacuo to afford 0.633 g (76%) of 92.

step 2—A mixture of 92 (630 mg, 2.27 mmol) and 12 (460 mg, 2.3 mmol) was heated to 150° C. overnight at which time no starting material was detected by TLC. The reaction mixture was purified by preparative HPLC on a 30×100 mm C18 ODB column eluting with MeCN/H₂O to afford 0.610 g (61%) of 94a as white solid.

step 3—TFA (2 mL) was added to a solution of 94a (1 mmol) in DCM (10 mL) at RT. The mixture was stirred at RT overnight and the solvent was removed in vacuo to afford 0.341 g (100%) of 94b which was used without additional purification.

step 4—A mixture of 94b (0.1 mmol), 66 (0.1 mmol) and TEA (0.1 mL) in MeCN (2 mL) was stirred at RT overnight. The reaction mixture was purified by preparative HPLC on a 30×100 mm C18 ODB column eluting with MeCN/H₂O to afford 0.035 g (72%) of I-57.

4-{5-Chloro-2-[1-(2-chloro-4-methanesulfonyl-benzyl)-piperidin-4-ylamino]-pyrimidin-4-yloxy}-3,5-dimethyl-benzonitrile (I-58) was prepared analogously except in step 1, 90 was replaced with 2,4,5-trichloro-pyrimidine (CASRN 5750-76-5)

Example 11

4-{4-[4-Amino-5-bromo-6-(4-cyano-2,6-dimethyl-phenoxy)-pyrimidin-2-ylamino]-piperidin-1-ylmethyl}-3-chloro-benzamide (II-2)

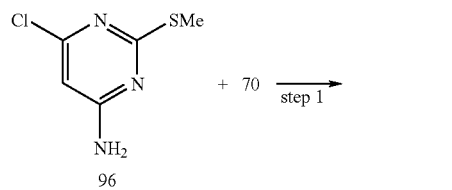

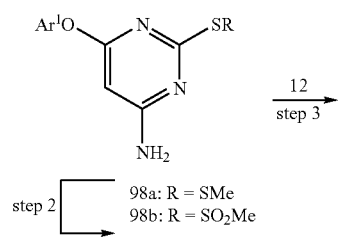

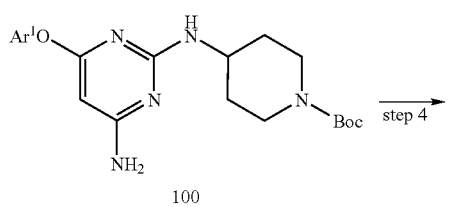

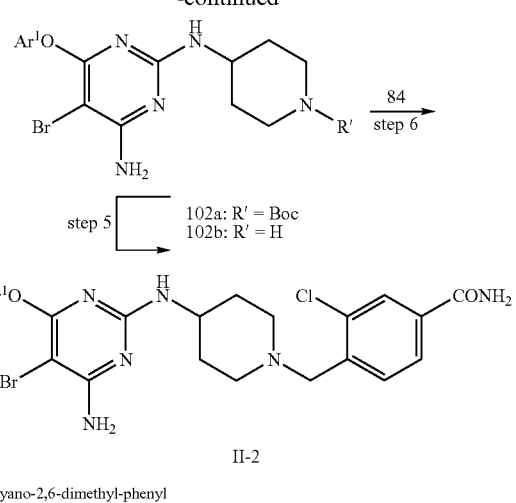

$Ar^1$ = 4-cyano-2,6-dimethyl-phenyl step 1—Sodium hydride (1 mmol, 60% in oil) was added portion wise to a solution of 70 in NMP at RT and the resulting solution was stirred for 10 min. To the sodium phenoxide solution was added 96 (1 mmol) and the resulting mixture was stirred for 30 h at 150° C. After the reaction was complete, the reaction was partitioned between EtOAc and H₂O and the water phase was extracted with EtOAc. The combined extracts were dried (Na₂SO₄), filtered and the solvent was evaporated to afford 98a as an oil which was used in the next step without further purification.

step 2—To a solution of 98a in DCM was added MCPBA (4 mmol) and the resulting mixture was stirred at RT for 4 h. After the reaction was complete, the reaction mixture was washed sequentially with saturated NaHSO₃ and saturated NaHCO₃. The organic phase was dried (Na₂SO₄), filtered and concentrated in vacuo to afford 0.123 g (38.6%) of 98b which was used without further purification.

step 3—A mixture of intermediate 98b (0.5 mmol) and 12 (0.5 mmol) was fused and heated at 150° C. for 2 h to afford 0.197 g (90%) of 100 which was used directly in the next step without purification.

step 4—To a solution of 100 (0.5 mmol) in DCM was added portion wise NBS (0.5 mmol). The resulting mixture was stirred for 10 min at RT. The reaction was quenched with water, the mixture was extracted with DCM, dried (Na₂SO₄), filtered and the solvent was removed in vacuo afford 0.273 g (100%) of 102a as a yellow oil which was directly used in the next step without purification.

step 5—To a solution of 102a (0.5 mmol) in DCM was added TFA (2.5 mL) and the resulting solution was stirred at RT for 5 h. After the reaction was complete, the solvents were concentrated in vacuo to afford 0.273 g (100%) of 102b as a yellow oil which was used the next step without purification.

step 6—To a solution of 102b (0.2 mmol) in MeCN was added TEA (0.4 mmol) and 84 (0.2 mmol), the resulting mixture was stirred at RT for 6 h. After the reaction was complete, the solvent was evaporated. The residue was purified by preparative HPLC on a 30×100 mm C18 ODB column eluting with MeCN/H₂O to afford 0.021 g (18.8%) of II-2.

The following were prepared analogously except 84 was replaced by the benzyl bromide in parenthesis: II-1 (4-bromomethyl-3-chloro-sulfonamide), II-3 (1-bromomethyl-2-chloro-4-methanesulfonyl-benzene).

Example 12

3-Chloro-4-{4-[4-(4-cyano-2-methyl-phenylamino)-pyrimidin-2-ylamino]-piperidin-1-ylmethyl}-benzenesulfonamide (III-18)

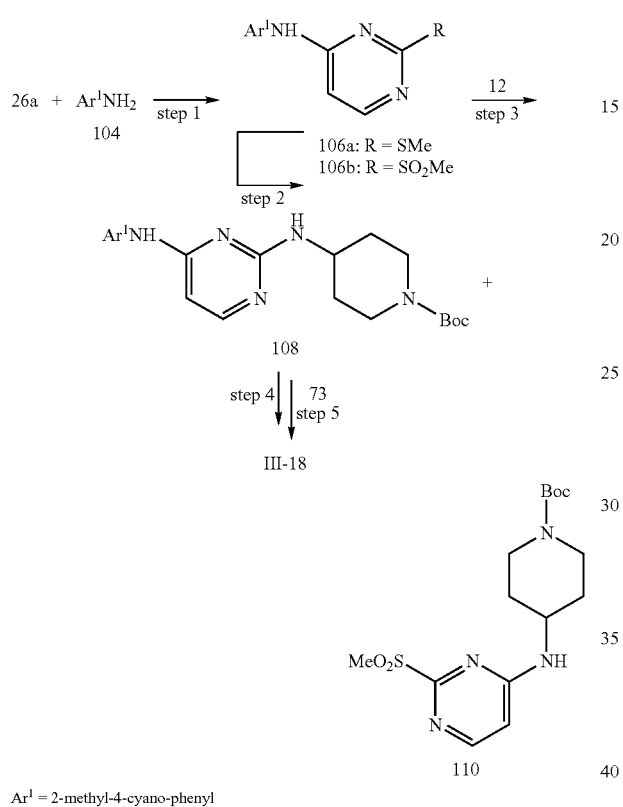

Ar¹ = 2-methyl-4-cyano-phenyl step 1—To a solution of 26a (1 mmol) in IPA was added 4-methyl-4-amino-benzonitrile (104, 1 mmol) then concentrated HCl (5 drops). The solution was stirred at 100° C. overnight. The reaction mixture was cooled and the resulting precipitate was filtered and washed thoroughly with IPA to afford 0.204 g (80%) of 106a.

step 2—To a solution of 106a (1 mmol) in DCM was added MCPBA (4 mmol) and the resulting mixture was stirred at RT for 4 h. After the reaction was complete, the reaction mixture was washed sequentially with saturated $NaHSO_3$ and saturated $NaHCO_3$ solution. The organic phase was dried ($Na_2SO_4$), filtered and evaporated to afford 0.296 g (100%) of 106b.

step 3—To a solution of 106b (1 mmol) in NMP was added 12 (1 mmol) and the resulting mixture was stirred at 150° C. for 30 min. After the reaction was complete, the resulting mixture was purified by $SiO_2$ chromatography eluting with EtOAc/hexane (1:2) to afford 0.080 g (20.8%) of 108.

steps 4 & 5—To a solution of 108 (0.2 mmol) in DCM was added TFA (1 μL) and the resulting solution was stirred at RT for 5 h. After the reaction was complete the reaction mixture was concentrated in vacuo to afford 0.0864 g (100%) of the TFA salt of the desired amine as a yellow oil which was dissolved in MeCN and to which was added TEA (0.5 mmol) and 73 (0.2 mmol) and the resulting mixture was stirred at RT for 6 h. After the reaction was completed, the solvent was evaporated and the residue was purified by preparative HPLC on a 30×100 mm C18 ODB column eluting with $MeCN/H_2O$ to afford 0.0078 g (8%) of III-18.

The following were prepared analogously using the aniline and benzyl bromide in parenthesis: III-2 (4-cyano-2,6-dimethyl-aniline, 73), III-4 (4-bromo-2,6-dimethyl-aniline, 73), III-6 (4-cyano-2,6-dimethyl-aniline, 84), III-8 (4-bromo-2,6-dimethyl-aniline, 66) and III-13 (4-cyano-2,6-dimethyl-aniline, iso-propyl 4-bromomethyl-3-chloro-benzoate). III-14 was prepared by hydrolysis of III-13 with LiOH in aqueous THF.

Example 13

4-{2-[1-(2-Chloro-4-methanesulfonyl-benzyl)-piperidin-4-ylamino]-pyrimidin-4-ylamino}-3,5-dimethyl-benzonitrile (III-1) and 4-{5-Bromo-2-[1-(2-chloro-4-methanesulfonyl-benzyl)-piperidin-4-ylamino]-pyrimidin-4-ylamino}-3,5-dimethyl-benzonitrile (III-5)

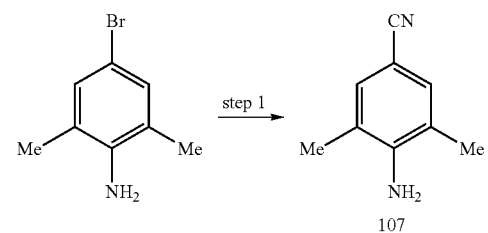

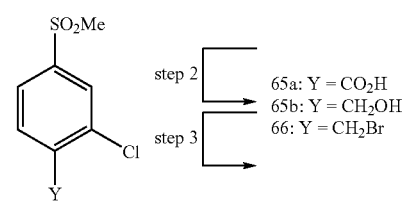

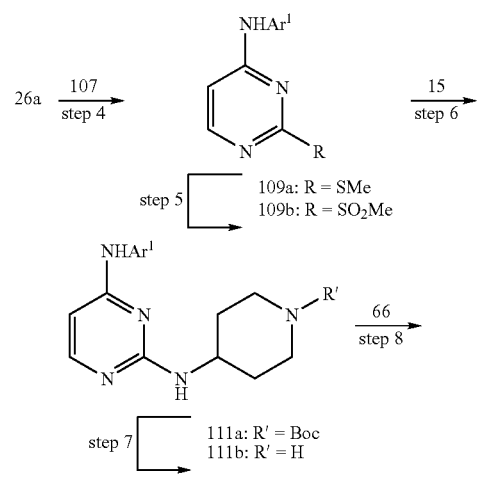

57

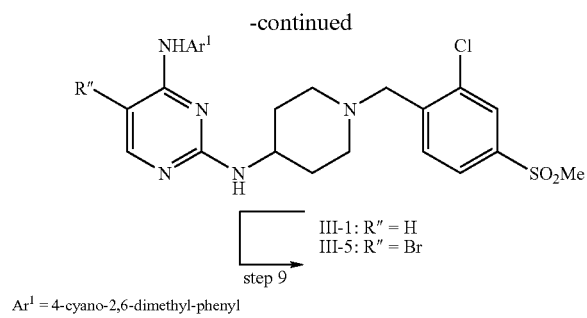

III-1: R″ = H
III-5: R″ = Br step 9

Ar¹ = 4-cyano-2,6-dimethyl-phenyl

Step 1—Preparation of 4-cyano-2,6-dimethylaniline

A mixture of 4-bromo-2,6-dimethylaniline (7.5 mmol, CASRN 24596-19-8) and CuCN (37.5 mmol) in NMP (10 mL) was stirred under microwave irradiation at 200° C. for 1 h. The mixture was poured into a mixture of water (50 mL) and EtOAc (50 mL). The precipitate was filtered and the filtrate was separated. The aqueous layer was extracted with EtOAc. The combined extracts were dried ($Na_2SO_4$). The solvent was removed in vacuo to afford 0.383 g (35%) of 107 as light pink solid which could be used without further purification.

step 2—2-Chloro-4-methylsulfonylbenzoic acid (65a, 21.3 mmol, CASRN 53250-83-2) was added under $N_2$ to a suspension of $LiAlH_4$ (25.5 mmol) in anhydrous THF (50 mL) at 0° C. The reaction mixture was allowed to warm to RT and stirred overnight. Water (1 mL), NaOH 15% (1 mL) and water (3 mL) were added sequentially to quench the reaction. The precipitate was filtered and the filtrate was extracted with EtOAc. The organic phase was dried ($Na_2SO_4$), filtered and evaporated to afford 2-chloro-4-methylsulfonylbenzyl alcohol (65b) as colorless oil which was used in next step without further purification.

step 3—$PBr_3$ (40 mmol) was added to a solution of 65b (21.3 mmol) in $Et_2O$ (50 mL) and the reaction mixture was stirred at RT for 4 h. Water (1 mL) was added to quench the reaction. The mixture was diluted with $Et_2O$ and washed with water and brine. The organic phase was dried ($Na_2SO_4$) and the solvent was evaporated. The residue was purified by $SiO_2$ chromatography eluting with EtOAc/hexane (1:4) to afford 5.25 g (87%) of 2-chloro-4-methylsulfonylbenzyl bromide (66) as white solid.

step 4—A mixture of 26a (2 mmol) and 107 (2 mmol) was heated in neat in a sealed tube at 160° C. The reaction mixture became a clear solution after 30 min and started to solidify as the product formed. After 6 h, TLC indicated that no starting material remained. The crude product containing 109a was used in next step without further purification.

step 5—MCPBA (6 mmol) was added portionwise to a solution of compound 109a (2 mmol) in DCM (15 mL) at 0° C. The reaction mixture was allowed to warm to RT and stirred for 3 h. The reaction mixture was quenched with $NaHSO_3$, diluted with DCM and washed sequentially with saturated $Na_2CO_3$, water, and brine. The organic phase was dried ($Na_2SO_4$) and the solvent was evaporated. The residue was purified by $SiO_2$ chromatography eluting with EtOAc/hexane (1:1) to afford 0.573 g (95%) of 109b.

step 6—A mixture of 109b (1.9 mmol) and 12 (2.1 mmol) in NMP (5 mL) was stirred at 150° C. overnight. Reaction mixture was purified by preparative HPLC on a 30×100 mm C18 ODB column eluting with $MeCN/H_2O$ to give 0.422 g (63%) of 111a as white solid.

58 step 7—TFA (1 mL) was added to a solution of 111a (1 mmol) in DCM (10 mL) at RT. The mixture was stirred at RT overnight and the solvent was removed to afford 0.700 g (100%) of 111b.

step 8—A mixture of 111b (1 mmol), 66 (1 mmol) and TEA (0.1 mL) in NMP (2 mL) was stirred at RT overnight. The reaction mixture was purified by preparative HPLC on a 30×100 mm C18 ODB column eluting with $MeCN/H_2O$ to afford 0.060 g (80%) of III-1 as white solid.

step 9—NBS (0.067 mmol) was added to a mixture of III-1 (0.067 mmol) in DCM (5 mL). The mixture was stirred at RT for 1 h and quenched with water (1 mL). The solvent was removed and the residue was purified by $SiO_2$ chromatography eluting with EtOAc/hexane (1:2) to afford 0.030 g (64%) of III-5 as white solid.

The following were prepared analogously using the aniline and benzyl bromide in parenthesis: III-7 (4-cyano-2,6-dimethyl-aniline, 4-bromomethyl-3-chloro-benzeneamide), III-11 (4-cyano-2,6-dimethyl-aniline, 4-bromomethyl-3-chloro-pyridine) and III-15 (2-chloro-4-cyano-6-methyl-aniline, 1-bromomethyl-2-chloro-4-methanesulfonyl-benzene).

III-17 was prepared analogously except in step 8, 66 was replaced with iso-propyl 4-bromomethyl-3-chloro-benzoate and after step 9 the carboxylic acid ester was hydrolyzed with LiOH in aqueous THF.

Example 14

4-{2-[(1R,5S)-8-(2-Chloro-4-methanesulfonyl-benzyl)-8-aza-bicyclo[3.2.1]oct-3-ylamino]-pyrimidin-4-ylamino}-3,5-dimethyl-benzonitrile (III-12)

109b + 80 —step 1→

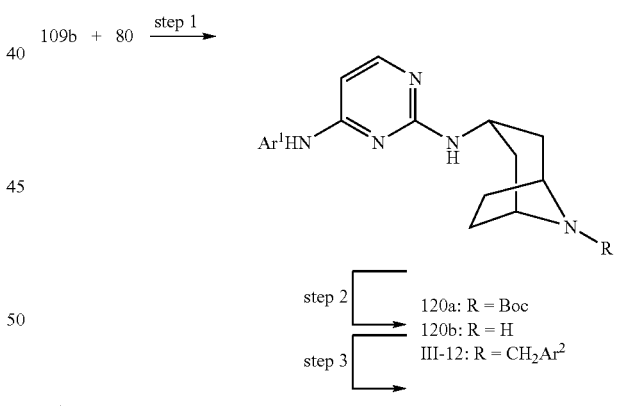

step 2  120a: R = Boc
        120b: R = H
step 3  III-12: R = $CH_2Ar^2$

Ar¹ = 4-cyano-3,5-dimethyl-phenyl
Ar² = 2-chloro-4-methanesulfonyl-phenyl step 1—A mixture of compound 109b (1.9 mmol) and 80 (2 mmol) in NMP (5 mL) was stirred at 150° C. overnight. The crude reaction mixture was purified by preparative HPLC on a 30×100 mm C18 ODB column eluting with $MeCN/H_2O$ to afford 0.502 g (56%) of 120a as white solid.

step 2—TFA (2 mL) was added to a solution of compound 120a (1 mmol) in DCM (10 mL) at RT and stirred overnight. The volatile material was removed in vacuo to afford 0.709 g (100%) of 120b which was used without additional purification.

step 3—A mixture of 120b (0.1 mmol), 66 (0.1 mmol) and TEA (0.1 mL) in MeCN (2 mL) was stirred at RT overnight. The solvent was evaporated and the product purified by preparative HPLC on a 30×100 mm C18 ODB column eluting with MeCN/H$_2$O to afford 0.042 g (76%) of III-12

Example 15

(E)-3-(4-{2-[1-(2-Chloro-4-methanesulfonyl-benzyl)-piperidin-4-ylamino]-pyrimidin-4-ylamino}-3,5-dimethyl-phenyl)-acrylonitrile (III-9)

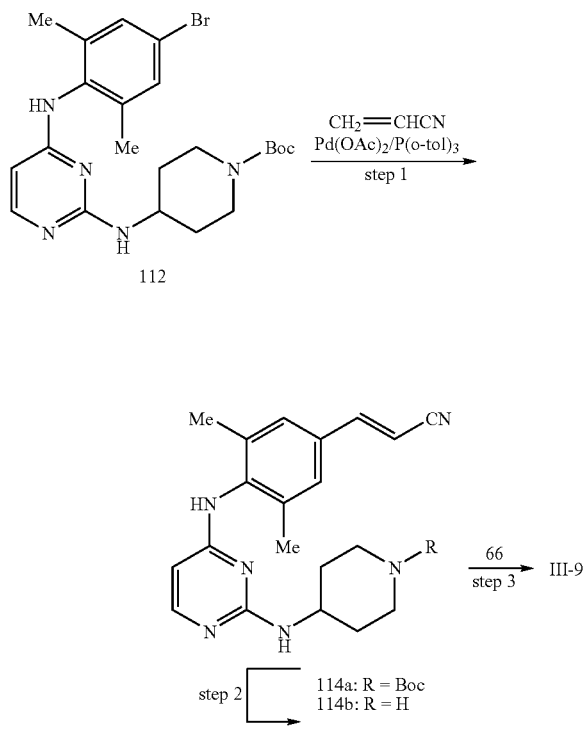

The starting material was prepared analogously to 108 (Example 13) except 4-bromo-2,6-dimethyl-aniline was used in place of 4-cyano-2,6-dimethyl-aniline in step 4.

step 1—A mixture of 112 (4.18 mmol), Pd(0)(OAc)$_2$ (0.836 mmol), tri-o-tolylphosphine (4.18 mmol), acrylonitrile (16.7 mmol) and TEA (16.7 mmol) in MeCN (20 mL) was stirred at 140° C. in a sealed tube for 48 h. The mixture was cooled, filtered and concentrated in vacuo. The residue was purified by SiO$_2$ chromatography eluting with EtOAc/hexane (1:3) to afford 0.560 g (30%) of 114a as white solid.

step 2—TFA (1 mL) was added to a solution of 114a (1.25 mmol) in DCM (10 mL) at RT. The mixture was stirred at RT overnight. The solvent was removed to afford 0.920 g (100%) of 114b.

step 3—A mixture of 114b (0.2 mmol), 66 (0.2 mmol) and TEA (1 mL) in NMP (2 mL) was stirred at RT for 2 h. The reaction mixture was concentrated and purified by preparative HPLC on a 30×100 mm C18 ODB column eluting with MeCN/H$_2$O to afford 0.080 g (72%) of III-9 as white solid.

III-10 was prepared analogously except in step 3, 66 was replaced with 4-bromomethyl-3-chloro-benzamide (84).

1H-16 was prepared by treating 1H-9 with NBS as described in step 9 of Example 13.

Example 16

3-{4-[4-(4-Cyano-2,6-dimethyl-phenylamino)-pyrimidin-2-ylamino]-piperidin-1-yl}-benzamide (IV-4)

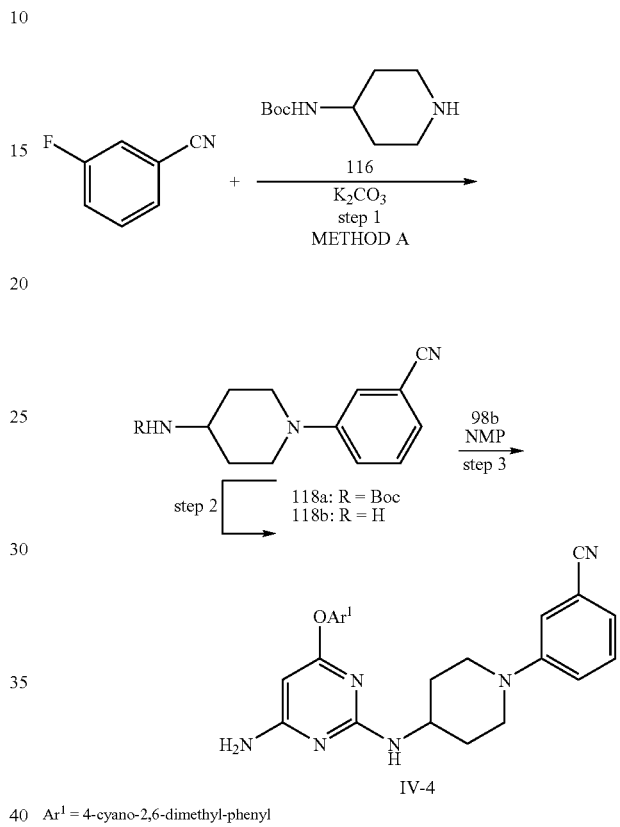

Ar$^1$ = 4-cyano-2,6-dimethyl-phenyl step 1 (Method A)—A mixture of 3-fluorobenzonitrile (24.8 mmol), 116 (37.2 mmol, CASRN 73870-95-0) and K$_2$CO$_3$ (49.6 mmol) in DMSO (21 mL) was stirred at 140° C. overnight. The cooled mixture was partitioned between water and EtOAc. The aqueous layer was extracted with EtOAc. The combined organic layers were washed with brine, dried (Na$_2$SO$_4$), filtered and concentrated in vacuo. The residue was purified by SiO$_2$ chromatography eluting with EtOAc/hexane (1:3) to afford 6.5 g (87%) of 118a.

step 2—TFA (5 mL) was added to a mixture of 118a (21.5 mmol) in DCM (100 mL). The mixture was stirred at RT overnight then evaporated to afford 12 g (100%) of 118b which was used without further purification.

step 3—The mixture of compound 118b (0.5 mmol), 98b (0.6 mmol) and TEA (1 mmol) in NMP (2 mL) was stirred at 150° C. overnight. It was purified by preparative HPLC on a 30×100 mm C18 ODB column eluting with MeCN/H$_2$O to afford 0.100 g (48%) of IV-4.

IV-5 and IV-6 was prepared analogously except in step 3, 98b was replaced with 4-(5-bromo-2-chloro-pyrimidin-4-yloxy)-2,6-dimethyl-benzonitrile (52) and 4-(2-chloro-pyrimidin-4-yloxy)-2,6-dimethyl-benzonitrile (68b), respectively.

IV-7 and IV-8 were prepared analogously utilizing 68b and 52 in place of 98b respectively and condensing each pyrimidine with 124 (see Example 18).

Example 17

4-{2-[1-(3-Methanesulfonyl-phenyl)-piperidin-4-ylamino]-pyrimidin-4-yloxy}-3,5-dimethyl-benzonitrile (IV-10)

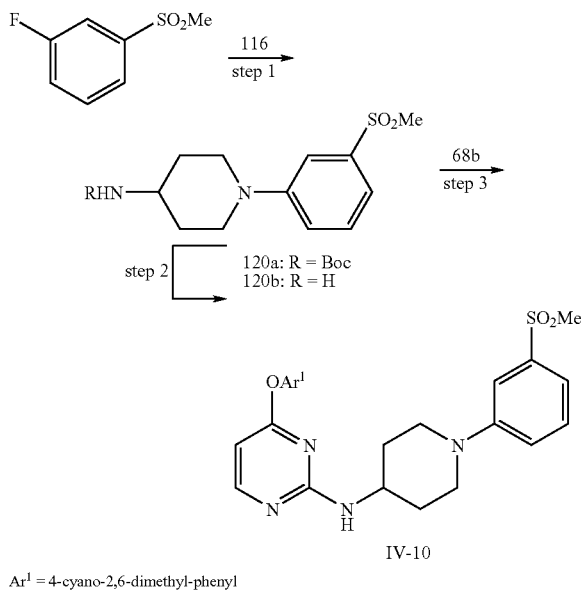

$Ar^1$ = 4-cyano-2,6-dimethyl-phenyl step 1—A mixture of 1-fluoro-3-methanesulfonyl-benzene (5 mmol) and 116 (5 mmol) in DIPEA (1 mL) and DMSO (10 mL) was heated at reflux for 48 h. After cooling, the mixture was poured into water (50 mL) and extracted with EtOAc. The organic phase was ($Na_2SO_4$), filtered and concentrated in vacuo. The residue was purified by $SiO_2$ chromatography eluting with EtOAc/hexane (1:2) to afford 0.970 g (77%) of 120a as white solid.

step 2—TFA (1 mL) was added to a solution of 120a (3.85 mmol) in DCM (10 mL) at RT. and stirred at RT overnight. The solvent was removed to afford 2.3 g (100%) of 120b which was used in the next step without further purification.

step 3—A mixture of 68b (0.0774 mmol), 120b (0.156 mmol) and DIPEA (0.2 µL) was heated at 130° C. in a sealed tube for 5 h. After cooling, the mixture was concentrated and purified by $SiO_2$ chromatography eluting with EtOAc/hexane (1:2) to afford 0.033 g (89%) of IV-10 as white solid.

4-(5-bromo-2-chloro-pyrimidin-4-yloxy)-3-chloro-5-methyl-benzonitrile (121a) and 3-chloro-4-(2-chloro-pyrimidin-4-yloxy)-5-methyl-benzonitrile (121b) was prepared by treating 5-bromo-2,4-dichloro-pyrimidine (CASRN 36082-50-5) and 68c, respectively, with 60c as described in step 1 of Example 6.

The following were prepared analogously using the substituted pyrimidine in parenthesis in place of 68b in step 3: IV-9 (4-(5-bromo-2-chloro-pyrimidin-4-yloxy)-2,6-dimethyl-benzonitrile, 52), IV-11 (121b), IV-12 (121a), IV-19 (4-(2-chloro-5-fluoro-pyrimidin-4-yloxy)-3,5-dimethyl-benzonitrile, 92), IV-20 (4-(2,5-dichloro-pyrimidin-4-yloxy)-3,5-dimethyl-benzonitrile), IV-21 (4-(2-chloro-5-trifluoromethyl-pyrimidin-4-yloxy)-3,5-dimethyl-benzonitrile).

The following were prepared analogously using 124 in place of 120b and using the substituted pyrimidine in parenthesis in place of 68a in step 3: IV-13 (4-(5-bromo-2-chloro-pyrimidin-4-yloxy)-3-chloro-5-methyl-benzonitrile), 4-(5-Bromo-2-chloro-pyrimidin-4-yloxy)-3-chloro-5-methyl-benzonitrile), IV-14 (3-chloro-4-(2-chloro-pyrimidin-4-yloxy)-5-methyl-benzonitrile), IV-15 (4-(2-chloro-5-fluoro-pyrimidin-4-yloxy)-3,5-dimethyl-benzonitrile, 92), IV-16 (4-(2,5-dichloro-pyrimidin-4-yloxy)-3,5-dimethyl-benzonitrile), IV-17 (4-(2-chloro-5-trifluoromethyl-pyrimidin-4-yloxy)-3,5-dimethyl-benzonitrile).

The following were prepared analogously using the substituted pyrimidine and 1-aryl-4-amino-piperidine (see Example 20) in parenthesis in step 3: IV-22 (121a, 134k), IV-23 (109b, 134k), IV-24 (121a, 135a), IV-25 (109b, 135a), IV-26 (109b, 135c), IV-27 (109b, 135b).

The following were prepared analogously using 121b in place of 68b in step 3 and the 1-aryl-4-aminopiperidine (see Example 20) in parentheses: IV-28 (134a), IV-29 (134c), IV-30 (134d)

IV-18 was prepared analogously using 68a and 1-(3-nitrophenyl)-piperidin-4-ylamine (CAS Reg No. 461720-07-0 for TFA salt, U.S. Pub. No. 20040106622). IV-31 is prepared by reduction of IV-18. Numerous methods for reduction of a nitro group to a primary amine exist and are well known within the art.

Example 18

3-{4-[4-(4-Cyano-2,6-dimethyl-phenylamino)-pyrimidin-2-ylamino]-piperidin-1-yl}-benzamide (V-4)

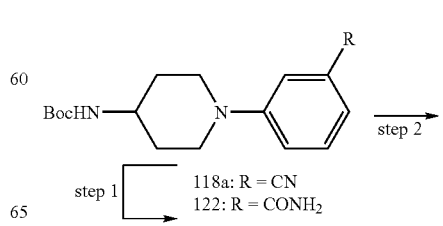

-continued

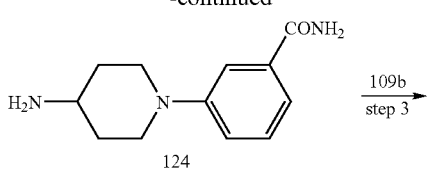

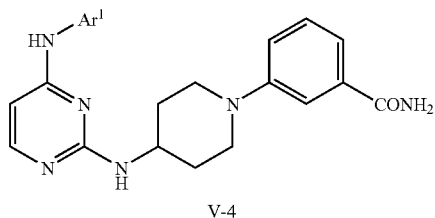

Ar¹ = 4-cyano-2,6-dimethyl-phenyl step 1—To a mixture of 118a (8.71 mmol) and NaOH (8.71 mmol) in EtOH (10 mL) was added $H_2O_2$ (10 mL) dropwise at RT. The mixture was stirred at 50° C. for 0.5 h. The aqueous layer was extracted with EtOAc. The combined extracts were washed with brine, dried ($Na_2SO_4$), filtered and concentrated in vacuo. The residue was purified by $SiO_2$ chromatography eluting with EtOAc/hexane (2:1) to afford 2.51 g (90%) of 122.

step 2—TFA (5 mL) was added to a solution of 122 (8.3 mmol) in DCM (100 mL). The solution was stirred at RT overnight then evaporated in vacuo to afford 124 which was used in the next step without further purification.

step 3—To a solution of 109b (0.2 mmol) in NMP was added the TFA salt of 124 (0.2 mmol) and TEA (0.4 mmol). The reaction was stirred at 150° C. overnight, cooled and the solvent removed in vacuo. The residue was purified by preparative HPLC on a 30×100 mm C18 ODB column eluting with $MeCN/H_2O$ to afford 0.023 g (26%) of V-4.

The following were prepared analogously using the substituted pyrimidine and piperidine in parenthesis in step 3: V-1 (109b, 118a), V-6 (3 4-(4-bromo-2,6-dimethyl-phenoxy)-2-methanesulfonyl-pyrimidine, 120b) and V-12 (109a, 134a).

V-9 was prepared analogously except in step 3 109b was replaced with 3-chloro-4-(2-methanesulfonyl-pyrimidin-4-yloxy)-5-methyl-benzonitrile. The latter is prepared by the condensation of 26a and 3-chloro-4-hydroxy-5-methyl-benzonitrile followed by MCPBA oxidation.

V-2 was prepared by condensation of 109b and 118a (from Example 20) as described in step 3 of the present example followed by NBS mediated bromination as described in step 9 of Example 13.

V-13 was prepared by condensation of 109b and 134b (from Example 20) as described in step 3 of the present example. V-14 was prepared by condensation of 4-(5-bromo-2-methanesulfonyl-pyrimidin-4-ylamino)-3,5-dimethyl-benzonitrile, which was prepared by NBS mediated bromination of 109b, and 134b (see example 20) as described in step 3 of the present example.

V-5 and V-3 were prepared by NBS mediated bromination of V-1 and V-4, respectively, as described in step 9 of Example 13.

Example 19

3-(4-{4-[4-((E)-2-Cyano-vinyl)-2,6-dimethyl-phenylamino]-pyrimidin-2-ylamino}-piperidin-1-yl)-benzamide (V-7)

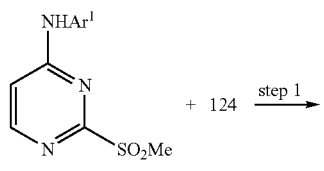

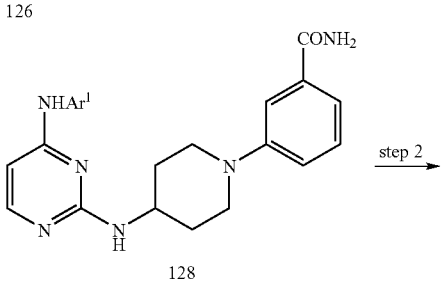

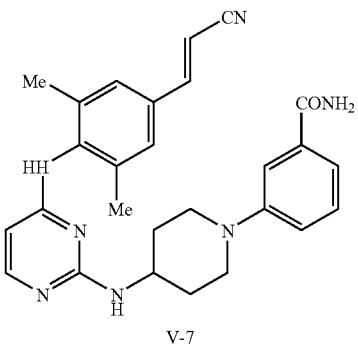

Ar¹ = 4-bromo-3,5-dimethyl-phenyl (4-Bromo-2,6-dimethyl-phenyl)-(2-methanesulfonyl-pyrimidin-4-yl)-amine (126) was prepared by the procedures described in as described in steps 4 and 5, respectively, of example 13 except 107 was replaced with 4-bromo-3,5-dimethyl-aniline.

step 1—A mixture of 126 (4 mmol) and 124 (4.3 mmol) in NMP (8 mL) was stirred at 150° C. overnight. The solvent was evaporated and the crude product was purified by preparative HPLC on a 30×100 mm C18 ODB column eluting with $MeCN/H_2O$ to afford 0.475 g (24%) of 128 as white solid.

step 2—A mixture of 128 (0.12 mmol), Pd(0)(OAc)$_2$ (0.024 mmol), tri-o-tolylphosphine (0.12 mmol) and acrylonitrile (0.5 mL) in TEA (0.5 mL) and MeCN (5 mL) was stirred at 140° C. in a sealed tube for 48 h. After cooling, the mixture was filtered and the filtrate was concentrated. The residue was purified by $SiO_2$ chromatography eluting with EtOAc to afford 0.0215 g (38%) of V-7 as a white solid.

V-8 was prepared analogously except (4-bromo-2-chloro-6-methyl-phenyl)-(2-methanesulfonyl-pyrimidin-4-yl)-amine (prepared from 4-bromo-2-chloro-6-methyl-phenylamine, CAS Reg. No 30273-42-8 and 26a as described in steps 4 and 5 of example 13) was used in step 1 in place of 126.

Example 20

4-[5-Bromo-2-(1-pyrimidin-5-yl-piperidin-4-ylamino)-pyrimidin-4-ylamino]-3,5-dimethyl-benzonitrile (V-15)

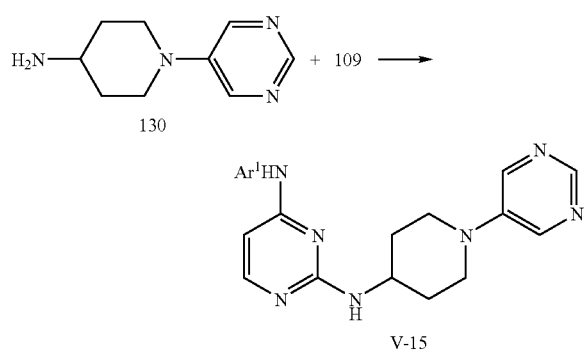

$Ar^1$ = 4-cyano-2,6-dimethyl-phenyl

General Procedure for CuI Catalyzed Coupling (Method B-Scheme E)

A mixture of aryl- or heteroaryl halide (1 mmol), 116 (1.2 mmol), $K_2CO_3$ (2 mmol), CuI (0.2 mmol) and L-proline (0.3 mmol) in DMSO (3 mL) was stirred at 90° C. for 20 h. The cooled mixture was partitioned between water and EtOAc. The organic layer was separated and the aqueous layer was again extracted with EtOAc. The combined organic extracts were washed with brine, dried ($Na_2SO_4$) and concentrated. The crude product was purified by $SiO_2$ chromatography to afford corresponding protected 1-(hetero)aryl-piperidin-4-ylamine derivative (yield: 20-80%).

The tert-butoxycarbonyl protecting group was removed from the coupled product with TFA and DCM as described in step 2 of Example 17.

To a solution of 109 (0.2 mmol) in NMP was added the TFA salt of 130 (0.2 mmol) and TEA (0.4 mmol). The reaction was stirred at 150° C. overnight, cooled and the solvent removed in vacuo. The residue was purified by preparative HPLC on a 30×100 mm C18 ODB column eluting with MeCN/$H_2O$ to afford 0.023 g (26%) of V-15.

The following 4-amino-1-(hetero)aryl-piperidines were prepared using the general schemes described above.

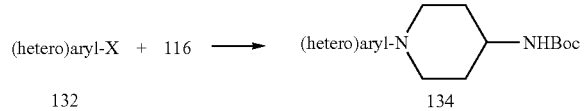

| Product 134 | Starting Material 132 | |
|---|---|---|
| 3,4,5,6-tetrahydro-2H-[1,3']bipyridinyl-4-ylamine (134a) | 3-iodo-pyridine | B[1] |
| 1-pyrimidin-5-yl-piperidin-4-ylamine (134b) | 5-bromo-pyrimidine | B |
| 1-pyrimidin-2-yl-piperidin-4-ylamine (134c) | 2-bromo-pyrimidine | B |
| [3-(4-amino-piperidin-1-yl)-phenyl]-acetonitrile (134d) | 3-bromo-phenyl-acetonitrile | B |

-continued

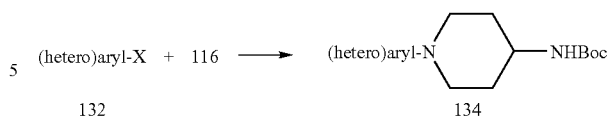

| Product 134 | Starting Material 132 | |
|---|---|---|
| (4-amino-3,4,5,6-tetrahydro-2H-[1,3']bipyridinyl-5'-yl)-acetonitrile (134f) | (5-bromo-pyridin-3-yl)-acetonitrile | B |
| 3-(4-amino-piperidin-1-yl)-benzenesulfonamide (134g) | 3-bromo-benzenesulfonamide | B |
| 4-(4-amino-piperidin-1-yl)-benzenesulfonamide (134h) | 4-bromo-benzenesulfonamide | B |
| 4-amino-3,4,5,6-tetrahydro-2H-[1,2']bipyridinyl-4'-carboxylic acid, methyl ester (134j) | 4-iodo-nicotinic acid, methyl ester | B |
| 3-(4-amino-piperidin-1-yl)-5-chloro-benzonitrile (134k) | 3-chloro-5-fluoro-benzonitrile | A[1] |
| 3-(4-amino-piperidin-1-yl)-5-fluoro-benzonitrile (134m) | 3,5-difluoro-benzaldehyde | A |
| 4-(4-Amino-piperidin-1-yl)-benzonitrile (134n) | 4-fluoro-benzonitrile | A |
| 2-(4-Amino-piperidin-1-yl)-benzonitrile (134o) | 2-fluoro-benzonitrile | A |

1. Method B - see Example 20
2. Method A - see Example 16

3-(4-Amino-piperidin-1-yl)-5-chloro-benzamide (135a), 4-(4-amino-piperidin-1-yl)-benzamide (135b) and 2-(4-amino-piperidin-1-yl)-benzamide (135c) were prepared from 134k, 134n, 134o, respectively, using the procedure described in step 1 of example 18.

Example 21

4-[4-(4-Cyano-2,6-dimethyl-phenylamino)-pyrimidin-2-ylamino]-3,4,5,6-tetrahydro-2H-[1,3']bipyridinyl-5'-carboxylic acid methyl ester (V-10) and 4-[4-(4-cyano-2,6-dimethyl-phenylamino)-pyrimidin-2-ylamino]-3,4,5,6-tetrahydro-2H-[1,3']bipyridinyl-5'-carboxylic acid (V-11)

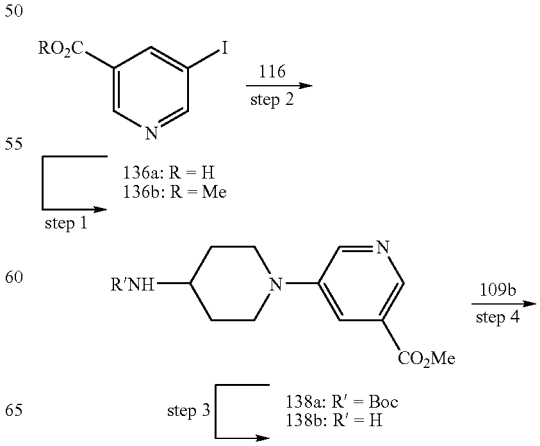

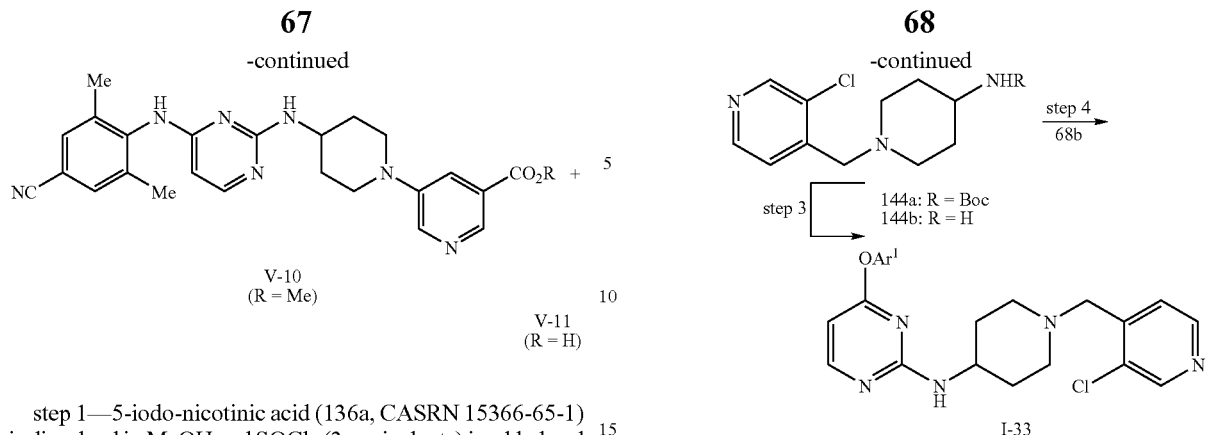

V-10 (R = Me)
V-11 (R = H)

step 1—5-iodo-nicotinic acid (136a, CASRN 15366-65-1) is dissolved in MeOH and SOCl$_2$ (3 equivalents) is added and the reaction is heated at reflux for 4 h. The reaction mixture is cooled and the volatile solvents evaporated. The residue is partitioned between DCM and saturated NaHCO$_3$ and the DCM is dried (Na$_2$SO$_4$), filtered and evaporated to afford 136b.

step 2—Cu(I) mediated condensation of 116 and 136b is carried our as using Method B as described in Example 20 to afford 138a.

steps 3 & 4 are carried out as described in steps 2 & 3 of example 18 to afford V-10. V-11 was isolated as a byproduct of this reaction.

Example 22

4-{5-Bromo-2-[1-(1-phenyl-ethyl)-piperidin-4-ylamino]-pyrimidin-4-yloxy}-3,5-dimethyl-benzonitrile (I-61)

To a solution of the TFA salt of 56 (1 mmol) in MeCN was added TEA (1.5 mmol) and (1-bromo-ethyl)-benzene (1 mmol) and the resulting mixture was stirred at RT for 6 h. After the reaction was complete, the solvent was removed and the residue was purified by preparative HPLC on a 30×100 mm C18 ODB column eluting with MeCN/H$_2$O to afford 0.120 g (24.6%) of I-61.

Example 23

4-{2-[1-(3-Chloro-pyridin-4-ylmethyl)-piperidin-4-ylamino]-pyrimidin-4-yloxy}-3,5-dimethyl-benzonitrile (I-33)

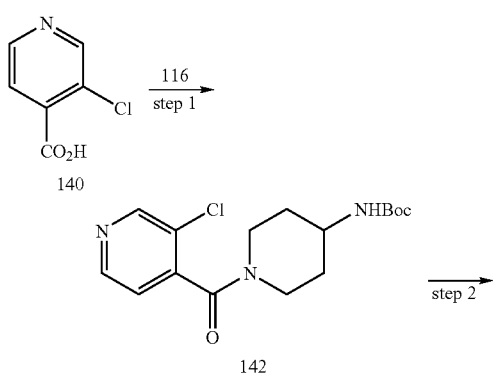

I-33
Ar$^1$ = 4-cyano-2,6-dimethyl-phenyl step 1—To a solution of 140 (1 mmol) in DCM (10 ml) was added EDC-HCl (1.1 mmol), HOBt (1.1 mmol), NMP (2.5 mmol). The resulting mixture was stirred at RT for 5 min, then 116 (1 mmol) was added and the reaction was stirred for 5 h. The mixture was quenched with a solution of 2% NaOH (10 mL) and extracted with DCM (3×10 mL). The combined organic extracts was washed with brine (15 mL), dried (Na$_2$SO$_4$), filtered, and evaporated to afford 659 mg (97.4%) of 142 a white solid.

step 2—To a solution of 142 (1 mmol) in THF was added BH$_3$-THF (1M, 4 mmol). The resulting mixture was stirred at 80° C. overnight. The reaction mixture was cooled to 0° C. and quenched by adding MeOH. After the solution was evaporated to dryness, the residue was purified by SiO$_2$ chromatography eluting with EtOAc/hexane (1:1) to afford 194 mg (60%) of 144a.

step 3—To a solution of 144a (0.3 mmol) in DCM was added TFA (1 mL) and the resulting solution was stirred at RT for 5 h. The solvents were concentrated in vacuo to afford a yellow oil (100%) which was used in the next step without further purification.

step 4—A solution of 68b (0.2 mmol) and 144b in DIPEA was heated to 120° C. in sealed tube for 5 h. The reaction mixture was purified by preparative HPLC to afford 29 mg (32%) of I-33 as white solid.

Example 24

3-{4-[5-Bromo-4-(4-cyano-2-methoxy-6-methyl-phenoxy)-pyrimidin-2-ylamino]-piperidin-1-yl}-benzamide (IV-40)

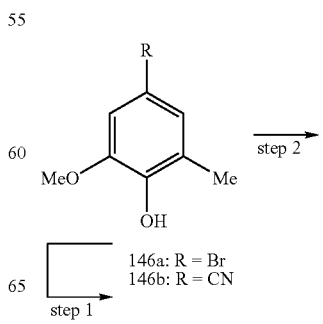

146a: R = Br
146b: R = CN

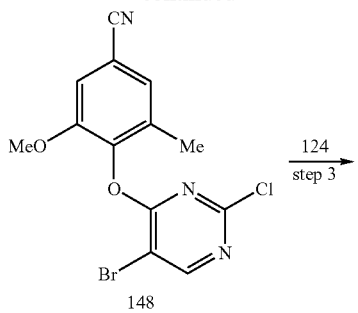

148

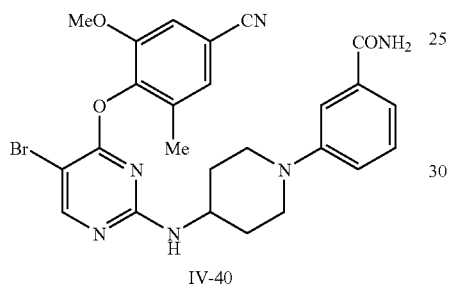

IV-40 step 1—A mixture of 146a (100 mmol) and CuCN (200 mmol) in DMSO (50 mL) was stirred at 150° C. overnight. The mixture was poured into a mixture of water (200 mL) and EtOAc (200 mL). The precipitate was filtered and the filtrate was separated. The aqueous layer was extracted with EtOAc. The combined organic extracts were dried ($Na_2SO_4$), filtered and concentrated in vacuo. The residue was purified by $SiO_2$ chromatography to afford product 146b (yield: 71.6%).

step 2—A mixture of 146b (10 mmol), 2,4-dichloro-5-bromo-pyrimidine (150, 10 mmol) and $K_2CO_3$ (15 mmol) in DMF (20 mL) was stirred at RT for 6 h. The mixture was poured into water (50 mL) and extracted with EtOAc. The organic phase was washed with brine, dried ($Na_2SO_4$), filtered and concentrated in vacuo. The residue was used in the next step without further purification.

step 3—A mixture of 124 (0.0774 mmol), 148 (0.0774 mmol) and DIPEA (0.2 mL) was heated at 110° C. in a sealed tube for 5 h. After cooling, the mixture was concentrated and purified by $SiO_2$ chromatography to afford 0.037 g (89%) of IV-40 as white solid.

IV-32, IV-33, IV-34 and IV-35 were prepared using the same procedure except 124 was replaced with 3-(4-amino-piperidin-1-yl)-benzoic acid methyl ester which is prepared from methyl 3-bromobenzoate and 116 utilizing the conditions described in step 1 of example 27. Hydrolysis of the ester and conversion to the amide was carried out by EDCI catalyzed coupling of the resulting acid with methylamine, cyclopropylamine, 2-amino-ethanol and 2-dimethylamino-ethane-amine. A representative coupling procedure is described in step 5 of example 27.

Example 25

3-{4-[4-(4-Cyano-2,6-dimethyl-phenoxy)-5-methyl-pyrimidin-2-ylamino]-piperidin-1-yl}-benzamide (IV-45)

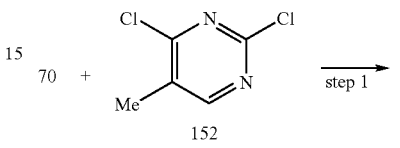

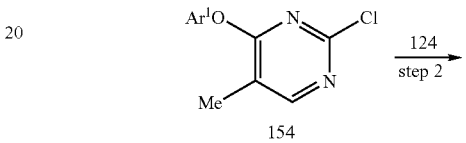

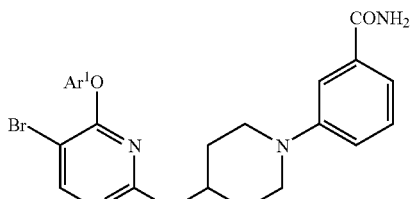

IV-45

$Ar^1$ = 4-cyano-2,6-dimethylphenyl step 1—Condensation of 70 and 152 (CASRN 1780-31-0) to afford 154 was carried out as described in step 2 of example 24.

step 2—A mixture of 124 (0.1 mmol), 154 (0.1 mmol) and DIPEA (0.2 mL) in DMSO (1 mL) was heated at 150° C. in a sealed tube overnight. After cooling, the mixture was concentrated and purified by $SiO_2$ chromatography to afford 0.033 g (73%) of IV-45.

Example 26

3-{4-[5-Bromo-4-(4-cyano-2-fluoro-6-methyl-phenoxy)-pyrimidin-2-ylamino]-piperidin-1-yl}-benzamide (IV-48)

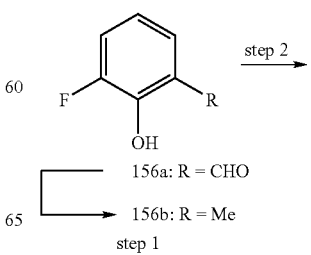

156a: R = CHO
156b: R = Me step 1

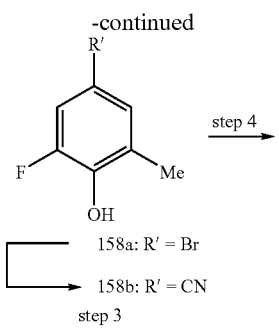

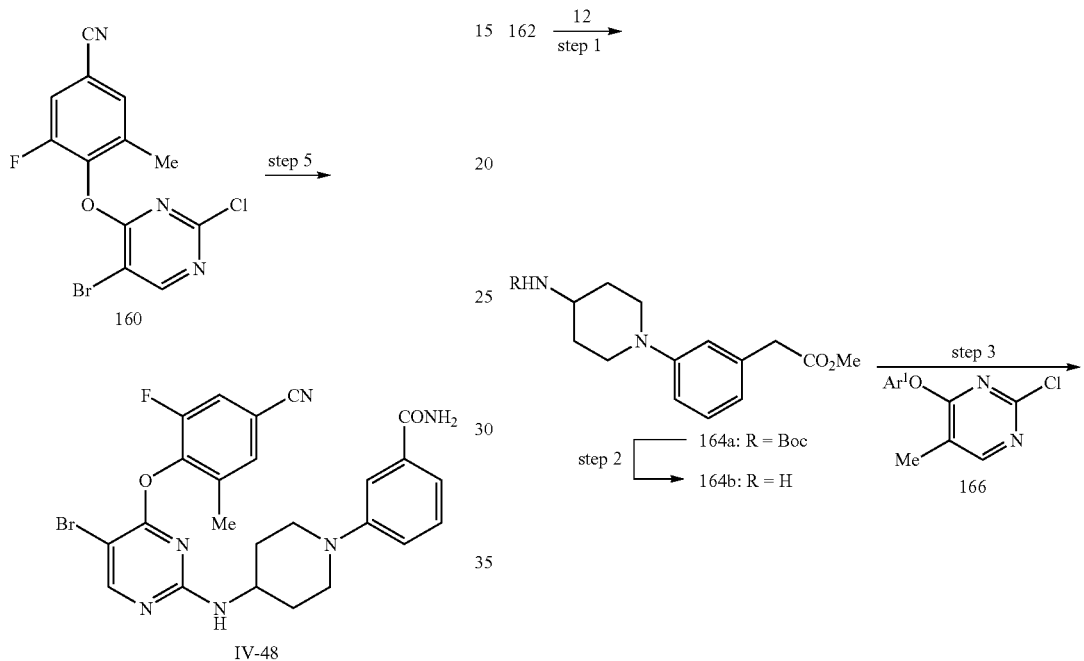

step 1—To a solution of 156a (3.0 g, 21.5 mmol, CASRN 394-50-3) in MeOH (250 mL) was added Pd/C (300 mg) under an argon atmosphere. The mixture was heated at 50° C. for 3 d under a 50 psi hydrogen atmosphere. The catalyst was filtered and the filtrate was concentrated in vacuo to afford 156b which was used in the next step without further purification.

step 2—To a solution of 156b (ca. 21.5 mmol from step 1) in HOAc (30 mL) in ice-water bath was added in portions NBS (4.0 g, 22.6 mmol). The mixture was warmed to RT and stirred overnight. Most of solvent was removed in vacuo. The residue was diluted with EtOAc then washed with water and brine. The organic phase was dried and concentrated in vacuo. The residue was purified by SiO₂ chromatography to afford 2.8 g (63.7% for two steps) of 158a as a white solid.

step 3—To a solution of 158a (2.8 g, 13.7 mmol) in DMSO (16 mL) was added CuCN (3.68 g, 41 mmol). The mixture was heated at 140° C. under an Ar atmosphere overnight. The mixture was cooled to about 100° C. and poured slowly to stirred EtOAc. The mixture was filtrated. The filtrate was washed with H₂O and the water phase was extracted with EtOAc. The combined organic extracts were washed with brine. The mixture was dried (Na₂SO₄), filtered and concentrated in vacuo. The crude product was purified by SiO₂ chromatography to afford to 1.72 g (80%) of 158b.

The phenol 158b was condensed with 150 as described in step 2 of example 24 to afford 160 which was condensed with 124 as described in step 3 of example 24 to afford II-48.

Example 27

2-(3-{4-[4-(2-Chloro-4-cyano-6-methyl-phenoxy)-5-methyl-pyrimidin-2-ylamino]-piperidin-1-yl}-phenyl)-acetamide (IV-46)

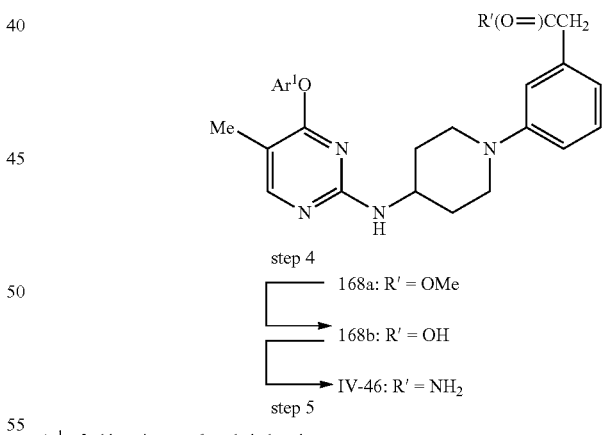

Ar¹ = 2-chloro-4-cyano-6-methyl-phenyl step 1—A mixture of (3-bromo-phenyl)-acetic acid methyl ester (162, 5 mmol), 116 (7 mmol), K₂CO₃ (10 mmol), CuI (0.5 mmol) and L-proline (1 mmol) in DMSO (10 mL) was heated at 90° C. overnight. The cooled mixture was partitioned between water and EtOAc. The organic layer was separated, and the aqueous layer was extracted with EtOAc. The combined organic extracts were washed with brine, dried (Na₂SO₄) and concentrated in vacuo. The residue was purified by SiO₂ chromatography to afford 0.91 g (74%) of 164a.

Step 2 was carried out as described in step 6 of example 5 to afford 164b. Condensation of 164b and 166 (step 3) was carried out as described in step 3 of example 24 to afford 168a. The requisite pyrimidine 166 was prepared by condensation of 3-chloro-4-hydroxy-5-methyl-benzonitrile and 152 as described in step 2 of example 24.

step 4—A mixture of 168a (1 mmol) and LiOH (10 mmol) in THF (3 mL) and H$_2$O (1 mL) was heated to reflux and stirred overnight. TLC indicated that starting material was consumed. The solvent was removed and the mixture was diluted with water and pH adjusted to ca. 3 with 2 N HCl. The product was filtered and dried in vacuo to afford 458 mg (93%) of 168b (93%).

step 5—A mixture of 168b (0.1 μmol), EDCI (0.15 mmol) and HOBt (0.15 mmol) in DCM was stirred at RT for 1 h then ammonia was added and the mixture was stirred overnight. The mixture was diluted with DCM and washed with 2 N NaOH solution. The organic layer was dried (Na$_2$SO$_4$), filtered and concentrated in vacuo. The residue was purified by SiO$_2$ chromatography to afford 0.040 g (82%) of IV-46.

IV-43 was prepared analogously to IV-46 except 152 was replaced with 150 to afford the corresponding 5-bromo-pyrimidine and in step 5 ammonia was replaced with 2-aminopropan-1-ol. IV-42 was prepared analogously to IV-43 except step 5 was omitted.

IV-36 was prepared analogously except 166 was replaced with 4-(5-bromo-2-chloro-pyrimidin-4-yloxy)-3,5-dimethyl-benzonitrile. IV-41 was prepared analogously to IV-36 except in step 5 ammonium was replaced with 2-dimethylamino-ethaneamine.

Example 28

4-{2-[1-(3-Cyanomethyl-phenyl)-piperidin-4-ylamino]-pyrimidin-4-ylamino}-3,5-dimethyl-benzonitrile (V-17)

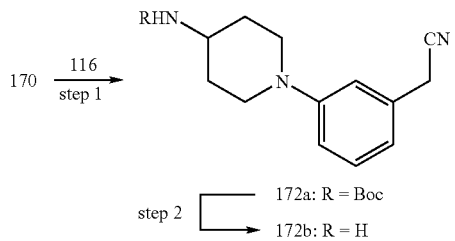

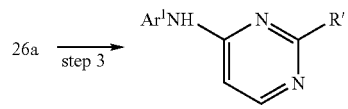

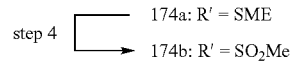

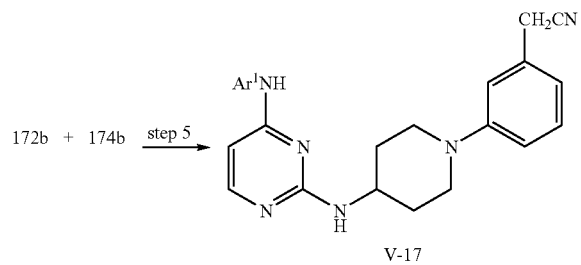

Ar$^1$ = 2,6-dimethyl-4-cyano-pphenyl

The preparation of 172b was carried out as described in step 1 of example 27 except (3-bromo-phenyl)-acetonitrile was used in place of 162. Step 2 was carried out as described in step 6 of example 5 to afford 172b.

step 3—A mixture of 26a (2 mmol) and 4-amino-3,5-dimethylbenzonitrile (2 mmol) was heated neat in a sealed tube at 160° C. The reaction mixture became clear solution after 30 min and start to solidify as the product formed. After 6 h, TLC indicated that no starting material remained. The crude product was used in next step without further purification.

step 4—m-CPBA (6 mmol) was added portion wise to a solution of 174a (2 mmol) in DCM (15 mL) at 0° C. After the reaction mixture was warmed to RT and stirred for 3 h. The reaction mixture was quenched with $Na_2S_2O_3$, diluted with DCM and washed sequentially with saturated $Na_2CO_3$, water, and brine. The organic phase was dried ($Na_2SO_4$), filtered and the solvent was evaporated. The residue was purified by $SiO_2$ chromatography to afford 0.573 g (95% for two steps) of 174b.

step 5—A mixture of 172b (0.1 mmol), 174b (0.1 mmol) and DIPEA (0.2 mL) in DMSO (2 mL) was heated at 150° C. in a sealed tube overnight. After cooling, the mixture was concentrated and purified by prep-HPLC to afford 0.024 g (56%) of V-17.

Example 29

N-(3-{4-[5-Bromo-4-(4-cyano-2,6-dimethyl-phenoxy)-pyrimidin-2-ylamino]-piperidin-1-yl}-phenyl)-acetamide (IV-39)

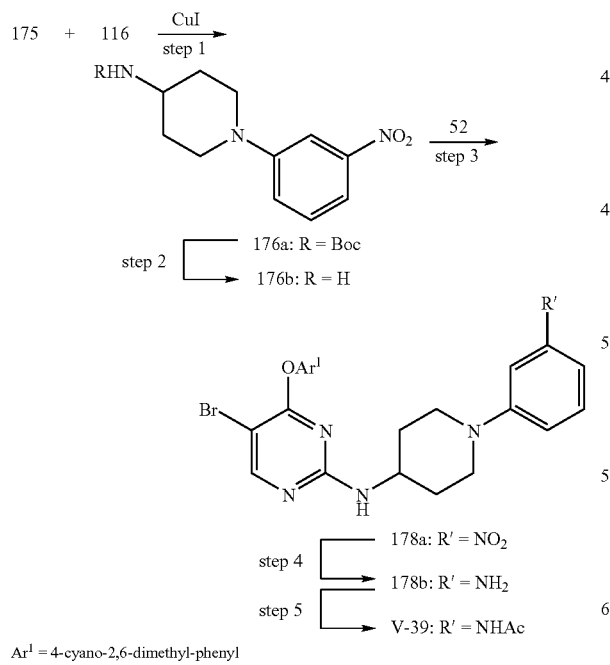

$Ar^1$ = 4-cyano-2,6-dimethyl-phenyl

The preparation of 176b was carried out as described in step 1 of example 27 except 3-bromo-nitrobenzene was used in place of 162. Step 2 was carried out as described in step 6 of example 5 to afford 176b. 4-(2-Amino-5-bromo-pyrimidin-4-yloxy)-3,5-dimethyl-benzonitrile (52) was prepared by condensation of 3,5-dimethyl-4-hydroxy-benzonitrile (177) and 150 as described in step 2 of example 24 except 146b was replaced by 177. Condensation of 176b and 52 (step 3) was carried out by the procedure described in step 3 of example 24.

step 4—A mixture of 178a (2 mmol) and $SnCl_2$ (6 mmol) in EtOAc (10 mL) was refluxed overnight. The mixture was washed with $Na_2CO_3$ solution (10 mL) and brine. The organic solution was dried ($Na_2SO_4$), filtered and concentrated to afford 178b which was used in the next step without additional purification.

step 5—To a solution of 178b (0.1 mmol) and DIPEA (0.2 mL) in DCM (5 mL) was added acetyl chloride (0.12 mmol) at 0° C. The reaction mixture was warmed to RT and stirred for 1 h. The solvent was evaporated and the residue was purified by $SiO_2$ chromatography to afford 0.40 g (74% for 2 steps) of IV-39.

IV-38 was prepared in analogous fashion except in step 5, acetyl chloride was replaced with methanesulfonyl chloride.

Example 30

2-(3-{4-[5-Bromo-4-(4-cyano-2,6-dimethyl-phenylamino)-pyrimidin-2-ylamino]-piperidin-1-yl}-phenyl)-N,N-dimethyl-acetamide (V-19)

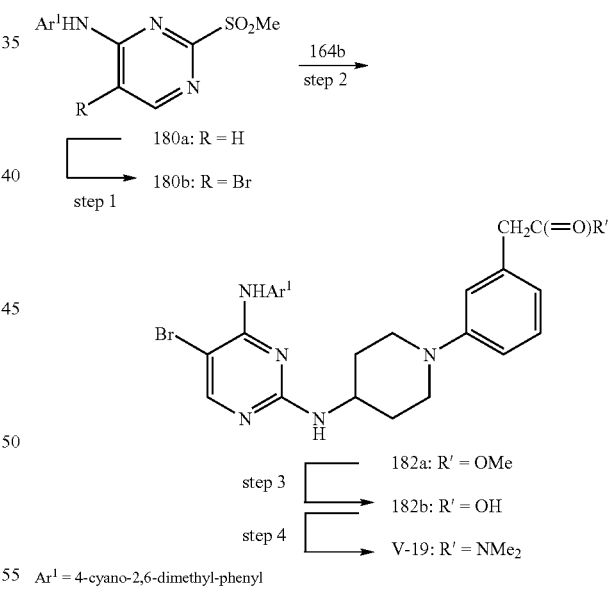

$Ar^1$ = 4-cyano-2,6-dimethyl-phenyl step 1—To a solution of 180a (0.5 mmol) in DCM was added NBS (1 mmol). The resulting mixture was stirred overnight at RT. The reaction was quenched with water and the mixture was extracted with DCM. The organic extract was dried ($Na_2SO_4$), filtered and solvents were evaporated. The residue was purified by $SiO_2$ chromatography to afford 0.169 g (85%) of 180b.

Condensation of 164b and 180b (step 2) was carried out by the procedure described in step 5 of example 28 to afford 182a. Steps 4 and 5 were carried out as described in steps 4 and 5 of example 27 except in step 5, ammonia was replaced by dimethylamine.

Example 31

4-{4-[5-Bromo-4-(4-cyano-2,6-dimethyl-phenylamino)-pyrimidin-2-ylamino]-piperidin-1-ylmethyl}-3-chloro-N-(2-dimethylamino-ethyl)-benzamide (III-19)

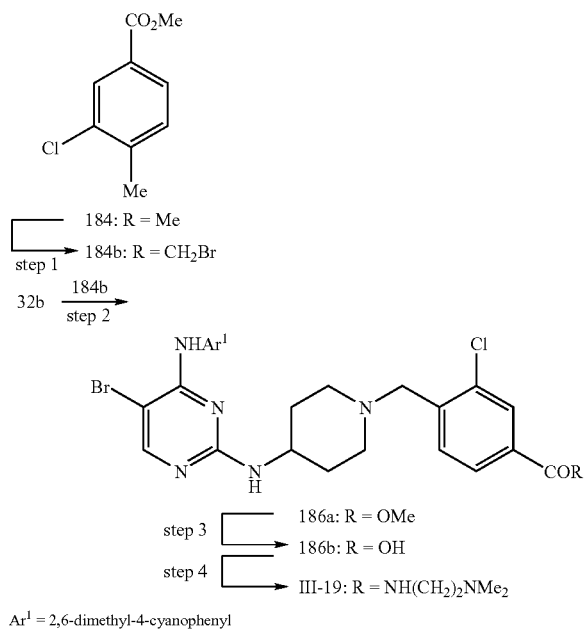

Ar¹ = 2,6-dimethyl-4-cyanophenyl step 1—A mixture of 184a (2 mmol), NBS (2.2 mmol) and AIBN (100 mg) in CCl₄ (20 mL) was heated at reflux for 4 h. The mixture was cooled, filtered and the filtrate was concentrated in vacuo. The residue was purified by SiO₂ chromatography to afford 0.395 g (75%) of 184b.

step 2—A mixture of 32b (1 mmol), 184b (1 mmol) and TEA (0.1 mL) in DCM (2 mL) was stirred at RT overnight. The mixture was concentrated and purified by SiO₂ chromatography to afford 0.467 g (80%) of 186a.

Steps 3 and 4 were carried out by the procedures described in steps 4 and 5 of example 27 except in step 5, ammonia was replaced with N¹,N¹-dimethyl-ethane-1,2-diamine.

Example 32

4-{5-Bromo-2-[1-(1-oxy-pyridin-4-ylmethyl)-piperidin-4-ylamino]-pyrimidin-4-yloxy}-3-chloro-5-methyl-benzonitrile (I-62)

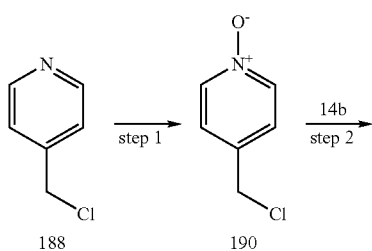

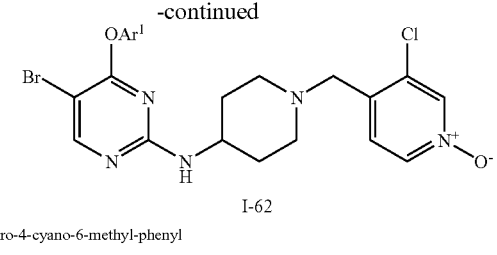

Ar¹ = 2-chloro-4-cyano-6-methyl-phenyl
Y¹ = Br step 1—To a solution of 188 (5 mmol) in DCM (20 mL) was added MCPBA (15 mmol) at RT and the reaction was stirred for 24 h. The precipitate was filtered and the filtrate was washed with Na2CO3. The organic layer was dried (Na₂SO₄), filtered and concentrated in vacuo. The residue was purified with SiO₂ chromatography to afford 0.066 g (92%) of 190.

Alkylation of 14b with 190 was carried as described in step 2 of example 31 to afford I-62.

Example 33

4-{5-Bromo-2-[1-(3-hydroxymethyl-phenyl)-piperidin-4-ylamino]-pyrimidin-4-yloxy}-3,5-dimethyl-benzonitrile (IV-37)

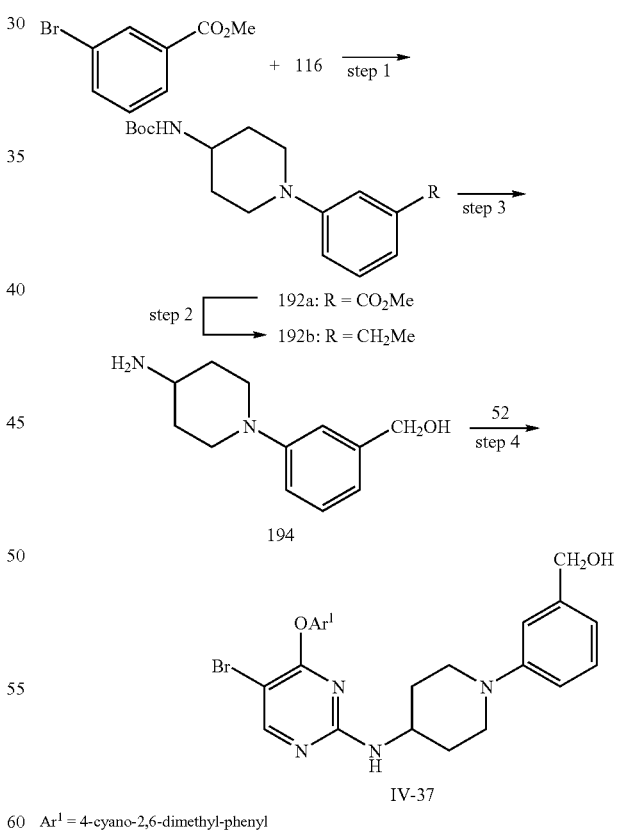

Ar¹ = 4-cyano-2,6-dimethyl-phenyl step 1—Condensation of methyl 3-bromoacetate and 116 was carried out by the procedure described in step 1 of example 27.

step 2—To a solution of 192a (5 mmol) in THF (15 mL) at RT was added LiAlH₄ (5 mmol) portion wise. After stirring for 4 h, the reaction mixture was cooled to 0° and quenched by addition of water (0.25 mL), 15% NaOH (0.25 mL), water (1 mL). The precipitate was filtered and the filtrate was concentrated. The residue was purified by SiO₂ chromatography to afford 1.12 g (73%) of 192b.

Removal of the Boc-protecting group (step 3) was accomplished by the procedure described in step 6 of example 5 to afford 194. Condensation of 194 and 52 (step 4) was carried out by the procedure described for step 36 of example 24 to afford IV-37

Example 34

4-(5-Bromo-2-{1-[3-(1,2-dihydroxy-ethyl)-phenyl]-piperidin-4-ylamino}-pyrimidin-4-yloxy)-3,5-dimethyl-benzonitrile (IV-44)

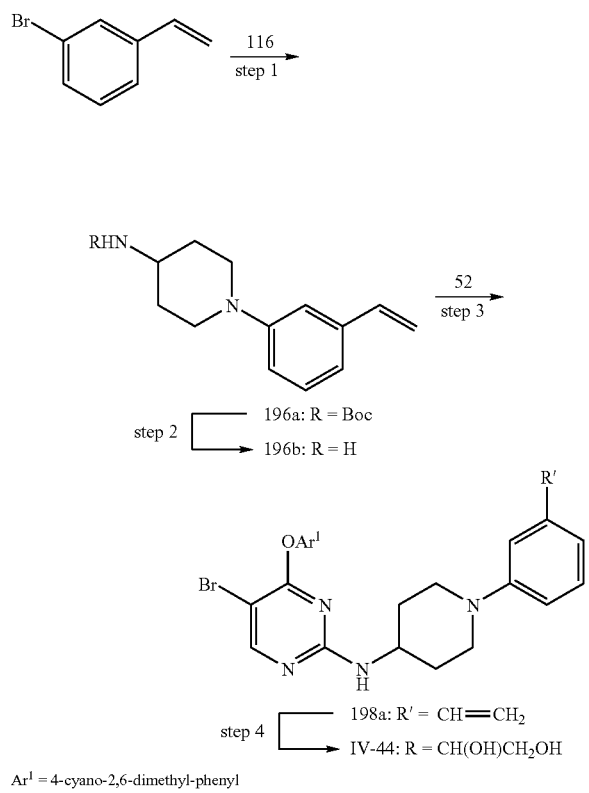

Ar¹ = 4-cyano-2,6-dimethyl-phenyl

Condensation of 3-bromo-styrene and 116 (step 1) was carried out by the procedure described in step 1 of example 27. Removal of the Boc-protecting group (step 2) was accomplished by the procedure described in step 6 of example 5 to afford 196b. Condensation of 196b and 52 (step 3) was carried out by the procedure described for step 3 of example 24 to afford 198a.

step 4—To a solution of 198a (0.5 mmol) and acetone (3 mL) at RT was added N-methyl-morpholine (1 mmol) and OsO₄ (5 mg). The mixture was stirred for 2 h, then Na₂S₂O₃ solution was added to quench the reaction and the mixture was stirred for 30 min. The mixture was partitioned between water and EtOAc. The organic layer was dried (Na₂SO₄), filtered and concentrated in vacuo. The residue was purified by preparative HPLC to afford 0.269 g (40%) of IV-44.

Example 35

2-(3-{4-[5-Bromo-4-(4-cyano-2,6-dimethyl-phenoxy)-pyrimidin-2-ylamino]-piperidin-1-yl}-phenyl)-propionic acid (IV-52)

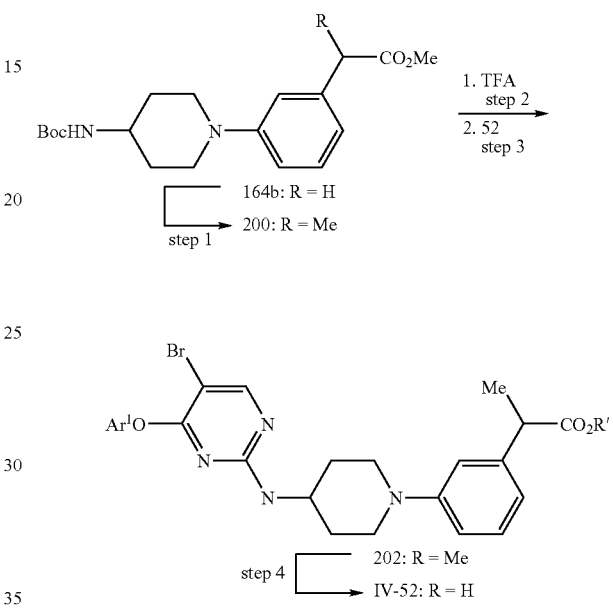

step 1—To a solution of 164b (300 mg, 0.86 mmol) in THF (2 mL) in ice-water bath was added dropwise a solution of potassium hexamethyldisilazane (2 mL, 0.5 mol/L, 1 mmol, KHMDS). The mixture was stirred at 0° C. for 30 min. Methyl iodide (246 mg, 1.72 mmol) was added and the mixture was warmed to RT for 1 h. Aqueous NH₄Cl was added to quench the reaction and the resulting mixture was extracted with EtOAc. The organic phase was dried (Na₂SO₄), filtered and concentrated in vacuo. The residue was purified by SiO₂ chromatography to afford 0.180 g (58%) of 200 as a yellow oil.

step 2—To a solution of 200 (180 mg, 0.5 mmol) in DCM (2 mL) was added TFA (0.5 mL) at RT. The mixture was stirred at RT for 2 h. The solvent was removed in vacuo and the residue was used in the next step without additional purification.

step 3—To the mixture of the TFA salt of 200 in DMSO (2 mL) was added DIPEA (646 mg, 5 mmol) followed by 52 (120 mg, 0.5 mmol). The mixture was heated at 120° C. overnight. The reaction mixture was cooled and poured into water then extracted with DCM. The organic phase was dried (Na₂SO₄), filtered and concentrated in vacuo. The residue was purified by SiO₂ chromatography to afford 0.150 g (53.2%) of 202 as an oil.

step 4—To a solution of compound 202 (150 mg, 0.27 mmol) in MeOH (2 mL) was added 2M aqueous NaOH (0.52 mL, 1.04 mmol). The mixture was heated at 45° C. for 2 h. After removal of most of solvents in vacuo, the mixture was acidified with diluted aqueous HCl. The mixture was concentrated in vacuo and the residue was dissolved in DMF. The solution was purified by preparative HPLC to afford 0.067 g (46.2%) of IV-52.

Example 36

2-(3-{4-[5-Bromo-4-(4-cyano-2,6-dimethyl-phenoxy)-pyrimidin-2-ylamino]-piperidin-1-yl}-phenyl)-3-hydroxy-propionic acid (IV-51)

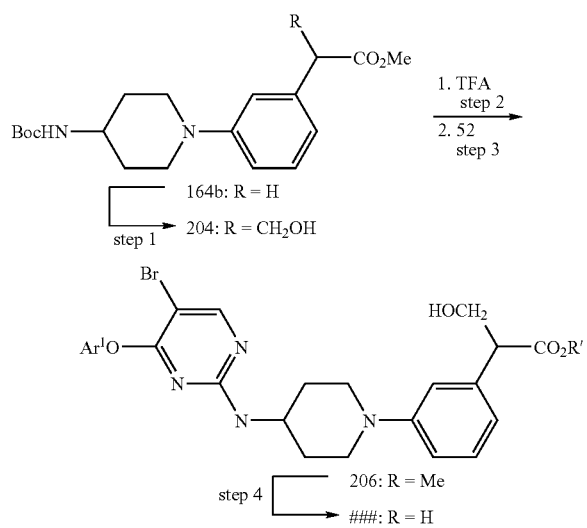

step 1—To a solution of 164 (200 mg, 0.57 mmol) in DMSO (1 mL) under Ar was added of NaHCO₃ (2.4 mg, 0.03 mmol) followed by paraformaldehyde (22 mg, 0.69 mmol). The mixture was stirred at RT for 2 h then heated at 45° C. for 12 h. The mixture was cooled, poured into water and extracted with ether. The organic phase was dried (Na₂SO₄), filtered and concentrated. The residue was purified by SiO₂ chromatography to afford 0.130 g (62.5%) of 204 as oil.

Steps 2-4 were carried out by the procedure described in steps 24 of example 35 to afford IV-51.

Example 37

(3-{4-[5-Bromo-4-(4-cyano-2,6-dimethyl-phenoxy)-pyrimidin-2-ylamino]-piperidin-1-yl}-phenyl)-difluoro-acetic acid (IV-55)

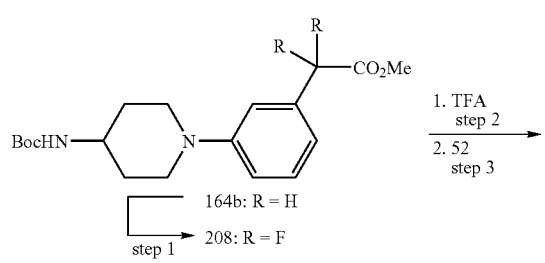

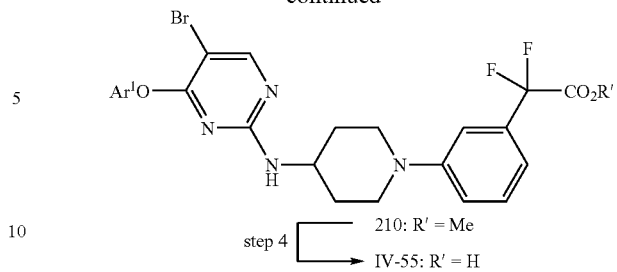

step 1—To a solution of 164b (400 mg, 1.14 mmol) in THF (6.8 mL) at −70° C. was added dropwise a solution of KHMDS (6.8 mL, 0.5 mol/L, 3.44 mmol). The mixture was stirred at −70° C. for 20 min. N-fluorobenzenesulfinimide (1.08 g, 1.72 mmol, CASRN 133745-75-2) was added in portions and the mixture was stirred at −70° C. for 30 min then warmed to −10° C. for 10 min. Water was added to quench the reaction and the resulting mixture extracted with EtOAc. The combined organic extracts were dried (Na₂SO₄), filtered and concentrated. The residue was purified by SiO₂ chromatography to afford 0.380 g (86.7%) of 210 as an oil.

Steps 2-4 were carried out as described in steps 2-4 of example 35 to afford IV-55.

Example 38

(3-{4-[5-Bromo-4-(4-cyano-2,6-dimethyl-phenoxy)-pyrimidin-2-ylamino]-piperidin-1-yl}-phenyl)-hydroxy-acetic acid (IV-54)

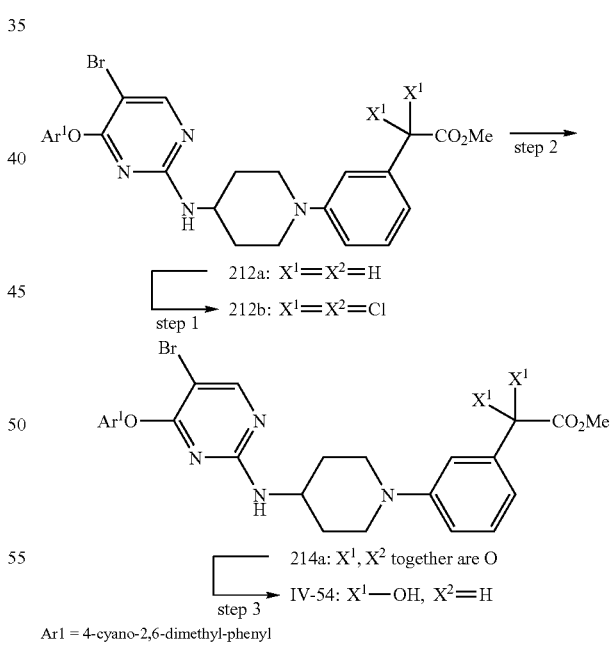

Ar1 = 4-cyano-2,6-dimethyl-phenyl step 1—To a solution of 212a (626 mg, 1.14 mmol) in THF (2 mL) at −70° C. was added dropwise a solution of KHMDS (5.5 mL, 0.5 mol/L, 2.74 mmol). The mixture was stirred at −70° C. for 20 min. N-chlorosuccimide (335 mg, 2.51 mmol, NCS) was added portion wise then the mixture was stirred at −70° C. for 30 min then warmed to 0° C. for 10 min. The reaction was quenched with aqueous NH₄Cl and the resulting mixture extracted with EtOAc. The organic phase was dried (Na₂SO₄), filtered and concentrated in vacuo to afford 0.680 g of 212b which was used directly in next step.

step 2—To a solution of compound 212b (230 mg, 0.37 mmol) in MeOH (2 mL) was added aqueous NaOH (1.8 mL, 2 mol/L, 3.6 mmol). The mixture was stirred at RT the cooled to RT. After removal of most of solvents in vacuo, the mixture was acidified with diluted aqueous HCl and filtered. The resulting solid is unstable and was used directly in the next step.

step 3—To a solution of 214a (120 mg, 0.21 mmol) from step 2 in MeOH (2 mL) at RT was added in portions NaBH₄ (75 mg, 2.1 mmol). The mixture was stirred at RT for 30 min. Aqueous HCl was added to quench the reaction and the resulting solution was concentrated in vacuo and the product was purified by preparative HPLC to afford 0.045 g (38.9%) of IV-54.

Example 39

(3-{4-[5-Bromo-4-(4-cyano-2,6-dimethyl-phenoxy)-pyrimidin-2-ylamino]-piperidin-1-yl}-phenyl)-methoxy-acetic acid (IV-53)

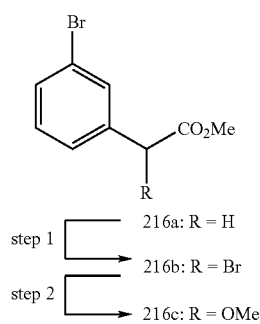

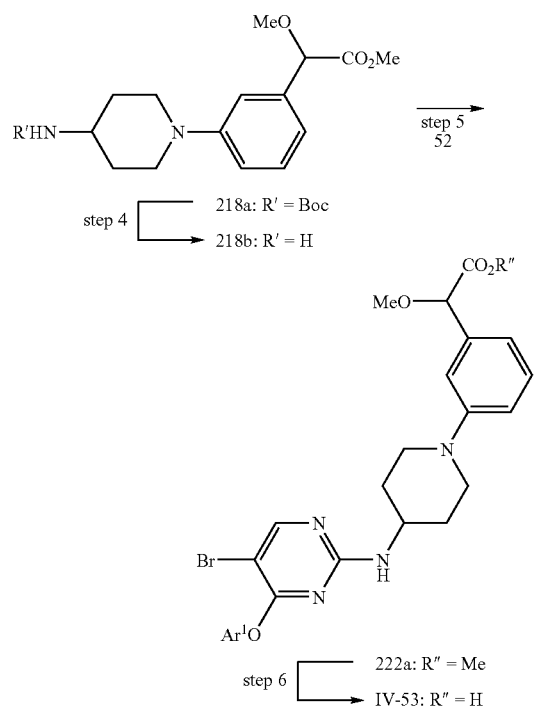

Ar¹ = 4-cyano-2,6-dimethyl-phenyl step 1—To a solution of 216a (1.19 g, 5 mmol) in CCl₄ (30 mL) was added NBS (1.08 g, 6 mmol) followed by benzoyl peroxide (catalytic quantity). The mixture was heated at 80° C. overnight. Then the mixture was cooled, filtered and the solid washed with hexane. The combined filtrates were concentrated in vacuo to afford 1.58 g (100%) of 216b as yellow oil.

step 2—To a sodium methoxide-MeOH solution from Na metal (0.44 g, 18.9 mmol) and MeOH (50 mL) was added 216b (4.86 g, 15.8 mmol) and the mixture was heated at 80° C. for 30 min. The resulting mixture was cooled and concentrated in vacuo. The residue was purified by SiO₂ chromatography to afford 2.5 g (62%) of 216c as an oil.

step 3—To a mixture of 216c (2.5 g, 9.6 mmol), CuI (164 mg, 0.96 mmol), L-proline (221 mg, 1.92 mg) and K₂CO₃ (2.65 g, 19.2 mmol) in DMSO (40 mL) was added 116 (2.7 g, 13.5 mmol). The mixture was heated at 100° C. overnight. The mixture was poured into water and extracted with EtOAc. The organic phase was dried (Na₂SO₄) and concentrated in vacuo. The residue was purified by SiO₂ chromatography to afford 0.670 g (18.4%) of compound 218a.

steps 4-6—Removal of the Boc-protecting group was accomplished by the procedure described in step 3 of example 24 to afford 218b. Condensation of 5-bromo-2,4-dichloro-pyrimidine (CASRN 36082-50-5) and 3,5-dimethyl-4-hydroxy-benzonitrile using the procedure described in step 2 of example 24 afforded 4-(5-bromo-2-chloro-pyrimidin-4-yloxy)-3,5-dimethyl-benzonitrile (220). Condensation of 52 and 218b and subsequent hydrolysis of the ester to afford IV-53 was carried out as described in steps 3 and 4 of example 34.

IV-56 and IV-57 were prepared by an analogous route except 5-bromo-2,4-dichloro-pyrimidine was replaced with 2,4,5-trichloro-pyrimidine and 2,4-dichloro-5-methyl-pyrimidine respectively.

Example 40

HIV-1 Reverse Transcriptase Assay Inhibitor IC₅₀ Determination

RNA-dependent DNA polymerase activity was measured using a biotinylated primer oligonucleotide and tritiated dNTP substrate. Newly synthesized DNA was quantified by capturing the biotinylated primer molecules on streptavidin coated Scintillation Proximity Assay (SPA) beads (Amersham). The sequences of the polymerase assay substrate were: 18 nt DNA primer, 5'-Biotin/GTC CCT GTT CGG GCG CCA-3'; 47 nt RNA template, 5'-GGG UCU CUC UGG UUA GAC CAC UCU AGC AGU GGC GCC CGA ACA GGG AC-3'. The biotinylated DNA primer was obtained from the Integrated DNA Technologies Inc. and the RNA template was synthesized by Dharmacon. The DNA polymerase assay (final volume 50 μl) contained 32 nM biotinylated DNA primer, 64 nM RNA substrate, dGTP, dCTP, dTTP (each at 5 μM), 103 nM [³H]-dATP (specific activity=29 μCi/mmol), in 45 mM Tris-HCl, pH 8.0, 45 mM NaCl, 2.7 mM Mg(CH₃COO)₂, 0.045% Triton X-100 w/v, 0.9 mM EDTA. The reactions contained 5 μl of serial compound dilutions in 100% DMSO for IC₅₀ determination and the final concentrations of DMSO were 10%. Reactions were initiated by the addition of 301 of the HIV-RT enzyme (final concentrations of 1-3 nM). Protein concentrations were adjusted to provide linear product formation for at least 30 min of incubation. After incubation at 30° for 30 min, the reaction was quenched by addition of 50 μl of 200 mM EDTA (pH 8.0) and 2 mg/ml SA-PVT SPA beads (Amersham, RPNQ0009, reconstituted in 20 mM Tris-HCl, pH 8.0, 100 mM EDTA and 1% BSA).

The beads were left to settle overnight and the SPA signals were counted in a 96-well top counter-NXT (Packard). IC$_{50}$ values were obtained by sigmoidal regression analysis using GraphPad Prism 3.0 (GraphPad Software, Inc.).

Example 41

Recombinant HIV-1 Antiviral Assay

The sensitivity of a wild-type laboratory strain HIV-1HXB2 to described compounds was determined by the 3-[4,5-dimethylthiazol-2yl]-2,5-diphenyltetrazolium bromide (MTT) cell viability assay with MT-4 cells (R. Pauwels et al., "Rapid and automated tetrazolium-based colorimetric assay for the detection of anti-HIV compounds," *J. Virological Methods* 1988 20:309-321). Briefly, MT-4 cells were incubated with virus (MOI 0.0001) for 1 h at 37° C. and then resuspended at 7.5×10$^5$/mL in RPMI 1640 (with out phenol) (Gibco) with 10% FCS and antibiotics and plated out onto a 96 well plate (Corning Costar, USA). After 5 days incubation 20 µL of MTT (Sigma-Aldrich) (5 mg/mL in PBS) was added and the plates were incubated for 2 h before the addition of 170 µL of acidified IPA. The absorbance was measured at 540 nm and the TCID$_{50}$ determined by Spearman-Karber method.

TABLE VI

| Compd. No. | HIVRT inhibition IC$_{50}$(µM) | Antiviral Activity IC$_{50}$(µM) |
| --- | --- | --- |
| I-3 | 0.0341 | 0.003 |
| IV-3 | 0.0147 | 0.0004 |
| V-5 | 0.0281 | 0.0015 |
| III-1 | 0.0257 | 0.0022 |
| I-24 | 0.0268 | 0.0039 |
| IV-13 | 0.0279 | 0.0058 |
| II-1 | 0.105 | 0.0086 |
| IV-23 | 0.0377 | — |
| V-3 | 0.04 | — |

Example 26

Pharmaceutical compositions of the subject compounds for administration via several routes were prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

(d) $C_{1-6}$ haloalkoxy,
(e) carboxyl,
(f) $CONR^{7a}R^{7b}$,
(g) $C_{1-6}$ alkoxycarbonyl,
(h) cyano,
(i) $SO_2$—$C_{1-6}$ alkyl,
(j) $SO_2NR^{8a}R^{8b}$,
(k) halogen,
(l) nitro,
(m) $C_{1-3}$ cyanoalkyl,
(n) $NR^{10a}R^{10b}$,
(o) $NR^{10a}SO_2C_{1-6}$ alkyl,
(p) $CHR^{11a}R^{11b}COR^{12}$,

---

---

We claim:

1. A compound according to formula I

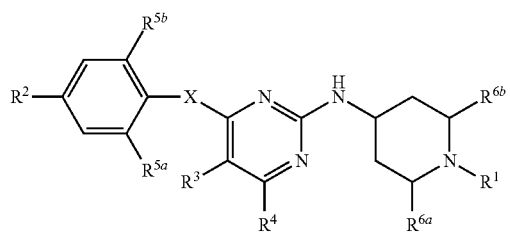

(I)

wherein:
$R^1$ is $CO_2$-tert-Bu, phenyl $C_{1-3}$ alkyl, heteroaryl $C_{1-3}$ alkyl, phenyl or heteroaryl wherein said heteroaryl group is selected from the group consisting of pyridinyl, pyridine-N-oxide, pyrimidinyl, thiophenyl, pyrrolyl, thiazolinyl, imidazolinyl or quinolyl and said phenyl or said heteroaryl is optionally substituted with one to three groups independently selected from the group consisting of:
(a) $C_{1-6}$ alkyl,
(b) $C_{1-6}$ alkoxy,
(c) $C_{1-6}$ haloalkyl, (q) hydroxyl, and
(r) $C_{1-6}$ heteroalkyl;
$R^2$ is —CN, —CH═CHCN, $C_{1-3}$ alkyl or halogen;
$R^3$ is hydrogen, halogen, amino or $C_{1-6}$ haloalkyl;
$R^4$ is hydrogen or amino;
$R^{5a}$ and $R^{5b}$ are independently hydrogen, $C_{1-6}$ alkyl, $C_{1-6}$ alkoxy or halogen;
$R^{6a}$ and $R^{6b}$ independently are hydrogen or together are ethylene;
$R^{7a}$ and $R^{7b}$
(i) taken independently, one of $R^{7a}$ and $R^{7b}$ is hydrogen, $C_{1-6}$ alkyl or $C_{3-7}$ cycloalkyl and the other of $R^{7a}$ and $R^{7b}$ is selected from the group consisting of hydrogen, $C_{1-6}$ alkyl, $C_{1-6}$ heteroalkyl, $C_{1-6}$ alkylsulfonyl, $C_{1-6}$ hydroxyalkyl, $C_{1-3}$ aminoalkyl-$C_{1-6}$ alkyl, $C_{1-3}$ dialkylamino-$C_{1-6}$ alkylalkyl and $C_{1-6}$ aminoalkyl;
(ii) taken together with the nitrogen atom to which they are attached, form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or,
(iii) taken together are $(CH_2)_2$—$X^1$—$(CH_2)_2$;
$R^{8a}$ and $R^{8b}$
(i) taken independently, one of $R^{8a}$ and $R^{8b}$ is hydrogen or $C_{1-6}$ alkyl and the other of $R^{8a}$ and $R^{8b}$ is selected from the group consisting of hydrogen, $C_{1-6}$ alkyl, $C_{1-6}$ acyl and $C_{1-6}$ heteroalkyl;

(ii) taken together with the nitrogen atom to which they are attached, form an azetidine, pyrrolidine, piperidine or azepine ring said azetidine, pyrrolidine, piperidine or azepine ring optionally substituted with hydroxy, amino, $C_{1-3}$ alkylamine or $C_{1-3}$ dialkylamine; or, (iii) taken together are $(CH_2)_2$—$X^1$—$(CH_2)_2$;

$R^9$ is hydrogen, $C_{1-3}$ alkyl or $C_{1-3}$ acyl;

$R^{10a}$ and $R^{10b}$ are independently hydrogen, $C_{1-3}$ alkyl or $C_{1-6}$ acyl;

$R^{11a}$ is hydrogen or halogen;

$R^{11b}$ is hydrogen, halogen, $C_{1-6}$ alkyl, $C_{1-6}$ alkoxy or $C_{1-6}$ hydroxyalkyl;

$R^{12}$ is hydroxyl, $C_{1-6}$ alkoxy or $NR^{7a}R^{7b}$;

X is NH or O;

$X^1$ is O, S(O)p or $NR^9$ p is an integer from 0 to 2; or, pharmaceutically acceptable salts thereof.

2. A compound according to claim 1 where $R^{7a}$, $R^{8a}$, $R^{8b}$ are hydrogen.

3. A compound according to claim 1 wherein $R^1$ is optionally substituted phenyl.

4. A compound according to claim 3 wherein $R^1$ is phenyl substituted with $CONR^7R^{7b}$, $SO_2NR^{8a}R^{8b}$ or $SO_2$—$C_{1-6}$ alkyl and optionally further substituted with one or two groups selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acylamino, (j) halogen, and, (k) nitro; and $R^{5a}$ and $R^{5b}$ are $CH_3$.

5. A compound according to claim 4 wherein $R^1$ is phenyl substituted with $CONH_2$, $SO_2NH_2$ or $SO_2$—$C_{1-3}$ alkyl and optionally further substituted with one or two groups selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro.

6. A compound according to claim 5 wherein $R^3$ is hydrogen or bromine; $R^4$ is hydrogen.

7. A compound according to claim 5 wherein $R^1$ is phenyl substituted at the three position by $CONH_2$, $SO_2NH_2$ or $C_{1-6}$ alkyl sulfonyl and optionally further substituted with one or two groups selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (l) $C_{1-6}$ alkoxycarbonyl, (h) cyano, (i) $C_{1-6}$ acylamino, (j) halogen, and, (k) nitro.

8. A compound according to claim 7 wherein $R^1$ is 3-carboxamido-phenyl, 3-aminosulfonyl-phenyl or 3-methanesulfonyl-phenyl, $R^3$ is hydrogen or bromine, and $R^4$ is hydrogen.

9. A compound according to claim 1 wherein $R^1$ is optionally substituted phenyl $C_{1-3}$ alkyl or optionally substituted heteroaryl $C_{1-3}$ alkyl and $R^{10a}$ and $R^{10b}$ are hydrogen.

10. A compound according to claim 9 wherein $R^1$ is optionally substituted phenyl $C_{1-3}$ alkyl.

11. A compound according to claim 10 wherein $R^1$ is phenyl $C_{1-3}$ alkyl substituted with $CONR^{7a}R^{7b}$, $SO_2NR^{8a}R^{8b}$ or $C_{1-6}$ alkyl sulfonyl and optionally further substituted with one or two groups selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acylamino, (j) halogen, and, (k) nitro; and $R^{Ra}$ and $R^{5b}$ are $CH_3$.

12. A compound according to claim 10 wherein $R^1$ is phenyl $C_{1-3}$ alkyl substituted at the four position by $CONH_2$, $SO_2NH_2$ or $C_{1-6}$ alkyl sulfonyl and optionally further substituted with one or two groups selected from the group consisting of (a) $C_{1-6}$ alkyl, (b) $C_{1-6}$ alkoxy, (c) $C_{1-6}$ haloalkyl, (d) $C_{1-6}$ haloalkoxy, (e) carboxyl, (f) $C_{1-6}$ alkoxycarbonyl, (h) cyano, (i) $C_{1-6}$ acyl-amino, (j) halogen, and, (k) nitro; and $R^{5a}$ and $R^{5b}$ are $CH_3$.

13. A compound according to claim 12 wherein $R^3$ is hydrogen or bromine; $R^4$ is hydrogen.

14. A compound according to claim 1 wherein $R^1$ is optionally substituted heteroaryl $C_{1-3}$ alkyl or heteroaryl, $R^4$, $R^{7a}$, $R^{7b}$, $R^{8a}$ and $R^{8b}$ are hydrogen.

15. A compound according to claim 1 wherein $R^1$ is phenyl substituted $CR^{11a}R^{11b}COR^{12}$, $R^{11a}$ and $R^{11b}$ are hydrogen and $R^{12}$ is $C_{1-6}$ alkoxy or $NR^{7a}R^{7b}$.

16. A compound according to claim 1 which compound is a free base or a pharmaceutically acceptable salt of a compound selected from the group consisting of:

4-[2-(1-Benzyl-piperidin-4-ylamino)-pyrimidin-4-yloxy]-3,5-dimethyl-benzonitrile, 4-[2-(1-Benzyl-piperidin-4-ylamino)-5-bromo-pyrimidin-4-yloxy]-3,5-dimethyl-benzonitrile, {2-[1-(4-Methanesulfonyl-benzyl)-piperidin-4-ylamino]-pyrimidin-4-yloxy}-3,5-dimethyl-benzonitrile, 4-{4-[5-Bromo-4-(4-cyano-2,6-dimethyl-phenoxy)-pyrimidin-2-ylamino]-piperidin-1-ylmethyl}-benzoic acid; compound with trifluoro-acetic acid, 4-[5-Bromo-2-(1-pyridin-4-ylmethyl-piperidin-4-ylamino)-pyrimidin-4-yloxy]-3,5-dimethyl-benzonitrile; compound with trifluoro-acetic acid, 4-{5-Bromo-2-(1-thiophen-2-ylmethyl-piperidin-4-ylamino)-pyrimidin-4-yloxy}-3,5-dimethyl-benzonitrile; compound with trifluoro-acetic acid, 4-[5-Bromo-2-(1-thiophen-3-ylmethyl-piperidin-4-ylamino)-pyrimidin-4-yloxy]-3,5-dimethyl-benzonitrile; compound with trifluoro-acetic acid, 4-[5-Bromo-2-(1-thiazol-2-ylmethyl-piperidin-4-ylamino)-pyrimidin-4-yloxy]-3,5-dimethyl-benzonitrile; compound with trifluoro-acetic acid, 4-{5-Bromo-2-[1-(4-cyano-benzyl)-piperidin-4-ylamino]-pyrimidin-4-yloxy}-3,5-dimethyl-benzonitrile; compound with trifluoro-acetic acid, N-(4-{4-[5-Bromo-4-(4-cyano-2,6-dimethyl-phenoxy)-pyrimidin-2-ylamino]-piperidin-1-ylmethyl}-phenyl)-acetamide; compound with trifluoro-acetic acid, 4-{5-Bromo-2-[1-(1H-pyrrol-2-ylmethyl)-piperidin-4-ylamino]-pyrimidin-4-yloxy}-3,5-dimethyl-benzonitrile; compound with trifluoro-acetic acid, 4-{5-Bromo-2-[1-(3H-imidazol-4-ylmethyl)-piperidin-4-ylamino]-pyrimidin-4-yloxy}-3,5-dimethyl-benzonitrile; compound with trifluoro-acetic acid, N-(3-{4-[5-Bromo-4-(4-cyano-2,6-dimethyl-phenoxy)-pyrimidin-2-ylamino]-piperidin-1-ylmethyl}-phenyl)-acetamide; compound with trifluoro-acetic acid, 4-{5-Bromo-2-[1-(3-fluoro-benzyl)-piperidin-4-ylamino]-pyrimidin-4-yloxy}-3,5-dimethyl-benzonitrile; compound with trifluoro-acetic acid, 4-{5-Bromo-2-[1-(3-nitro-benzyl)-piperidin-4-ylamino]-pyrimidin-4-yloxy}-3,5-dimethyl-benzonitriletrifluoro-acetic acid, 4-{5-Bromo-2-[1-(4-methanesulfonyl-benzyl)-piperidin-4-ylamino]-pyrimidin-4-yloxy}-3,5-dimethyl-benzonitrile, 4-{5-Bromo-2-[1-(2-chloro-4-methanesulfonyl-benzyl)-piperidin-4-ylamino]-pyrimidin-4-yloxy}-3,5-dimethyl-benzonitrile, 4-{5-Bromo-2-[1-(4-nitro-benzyl)-piperidin-4-ylamino]-pyrimidin-4-yloxy}-3,5-dimethyl-benzonitriletrifluoro-acetic acid, 4-{5-Bromo-2-[1-(2-cyano-benzyl)-piperidin-4-ylamino]-pyrimidin-4-yloxy}-3,5-dimethyl-benzonitrile; compound with trifluoro-acetic acid, 4-{5-Bromo-2-[1-(3-cyano-benzyl)-piperidin-4-ylamino]-pyrimidin-4-yloxy}-3,5-dimethyl-benzonitrile; trifluoroacetate salt, {4-[5-Bromo-4-(4-cyano-2,6-dimethyl-phenoxy)-pyrimidin-2-ylamino]-piperidin-1-ylmethyl}-3-chloro-benzenesulfonamide, 4-{4-[5-Bromo-4-(4-cyano-2,6-dimethyl-phenoxy)-pyrimidin-2-ylamino]-piperidin-1-ylmethyl}-3-chloro-benzoic acid, 3-Chloro-4-{4-[4-(4-cyano-2,6-dimethyl-phenoxy)-pyrimidin-2-ylamino]-piperidin-1-ylmethyl}-benzenesulfonamide, 3-Chloro-4-{4-[4-(2-chloro-4-cyano-6-methyl-phenoxy)-pyrimidin-2-ylamino]-piperidin-1-ylmethyl}-benzenesulfonamide, 3-Chloro-4-{4-[4-(2-chloro-4-cyano-phenoxy)-pyrimidin-2-ylamino]-piperidin-1-ylmethyl}-benzenesulfonamide, 3-Chloro-4-{4-[4-(4-cyano-2,6-dimethyl-phenoxy)-pyrimidin-2-ylamino]-piperidin-1-ylmethyl}-benzamide, 4-{2-[1-(2-Chloro-4-methanesulfonyl-benzyl)-piperidin-4-ylamino]-pyrimidin-4-yloxy}-3,5-dimethyl-benzonitrile, 4-{4-[5-Bromo-4-(4-cyano-2,6-dimethyl-phenoxy)-pyrimidin-2-ylamino]-piperidin-1-ylmethyl}-3-chloro-benzamide, 4-{2-[1-(2-Chloro-4-cyano-benzyl)-piperidin-4-ylamino]-pyrimidin-4-yloxy}-3,5-dimethyl-benzonitrile, 4-{5-Bromo-2-[1-(2-chloro-4-cyano-benzyl)-piperidin-4-ylamino]-pyrimidin-4-yloxy}-3,5-dimethyl-benzonitrile, 4-{5-Bromo-2-[1-(2,3-difluoro-benzyl)-piperidin-4-ylamino]-pyrimidin-4-yloxy}-3,5-dimethyl-benzonitrile, 4-{5-Bromo-2-[1-(3-chloro-pyridin-4-ylmethyl)-piperidin-4-ylamino]-pyrimidin-4-yloxy}-3,5-dimethyl-benzonitrile, 4-{2-[1-(3-Chloro-pyridin-4-ylmethyl)-piperidin-4-ylamino]-pyrimidin-4-yloxy}-3,5-dimethyl-benzonitrile, {5-Bromo-2-[1-(4-tert-butyl-benzyl)-piperidin-4-ylamino]-pyrimidin-4-yloxy}-3,5-dimethyl-benzonitrile, 4-{5-Bromo-2-[1-(3-trifluoromethyl-benzyl)-piperidin-4-ylamino]-pyrimidin-4-yloxy}-3,5-dimethyl-benzonitrile, 4'-{4-[5-Bromo-4-(4-cyano-2,6-dimethyl-phenoxy)-pyrimidin-2-ylamino]-piperidin-1-ylmethyl}-biphenyl-2-carbonitrile, 4-{5-Bromo-2-[1-(4-trifluoromethoxy-benzyl)-piperidin-4-ylamino]-pyrimidin-4-yloxy}-3,5-dimethyl-benzonitrile, 4-{5-Bromo-2-[1-(3-trifluoromethoxy-benzyl)-piperidin-4-ylamino]-pyrimidin-4-yloxy}-3,5-dimethyl-benzonitrile, 4-{5-Bromo-2-[1-(3-chloro-benzyl)-piperidin-4-ylamino]-pyrimidin-4-yloxy}-3,5-dimethyl-benzonitrile, 4-{5-Bromo-2-[1-(4-chloro-benzyl)-piperidin-4-ylamino]-pyrimidin-4-yloxy}-3,5-dimethyl-benzonitrile, 4-{2-[1-(2,4-Bis-trifluoromethyl-benzyl)-piperidin-4-ylamino]-5-bromo-pyrimidin-4-yloxy}-3,5-dimethyl-benzonitrile, 4-{5-Bromo-2-[1-(3,5-dimethoxy-benzyl)-piperidin-4-ylamino]-pyrimidin-4-yloxy}-3,5-dimethyl-benzonitrile, 4-[5-Bromo-2-(1-quinolin-8-ylmethyl-piperidin-4-ylamino)-pyrimidin-4-yloxy]-3,5-dimethyl-benzonitrile, 4-{5-Bromo-2-[1-(3-chloro-4-fluoro-benzyl)-piperidin-4-ylamino]-pyrimidin-4-yloxy}-3,5-dimethyl-benzonitrile, 4-{2-[1-(3-Chloro-pyridin-4-ylmethyl)-piperidin-4-ylamino]-pyrimidin-4-ylamino}-3,5-dimethyl-benzonitrile, 3-Chloro-4-{(1R,5S)-3-[4-(4-cyano-2,6-dimethyl-phenoxy)-pyrimidin-2-ylamino]-8-aza-bicyclo[3.2.1]oct-8-ylmethyl}-benzamide, 4-{2-[(1R,5S)-8-(2-Chloro-4-methanesulfonyl-benzyl)-8-aza-bicyclo[3.2.1]oct-3-ylamino]-pyrimidin-4-yloxy}-3,5-dimethyl-benzonitrile, 3-Chloro-4-{1-(2-chloro-4-methanesulfonyl-benzyl)-piperidin-4-ylamino}-pyrimidin-4-yloxy}-5-methyl-benzonitrile, 4-{5-Bromo-2-[(1R,5S)-8-(2-chloro-4-methanesulfonyl-benzyl)-8-aza-bicyclo[3.2.1]oct-3-ylamino]-pyrimidin-4-yloxy}-3,5-dimethyl-benzonitrile, 4-{(1R,5S)-3-[5-Bromo-4-(4-cyano-2,6-dimethyl-phenoxy)-pyrimidin-2-ylamino]-8-aza-bicyclo[3.2.1]oct-8-ylmethyl}-3-chloro-benzamide, 4-{5-Bromo-2-[1-(2-chloro-4-methanesulfonyl-benzyl)-piperidin-4-ylamino]-pyrimidin-4-yloxy}-3-chloro-5-methyl-benzonitrile, 4-{4-[5-Bromo-4-(4-cyano-2,6-dimethyl-phenylamino)-pyrimidin-2-ylamino]-piperidin-1-ylmethyl}-3-chloro-benzoic acid isopropyl ester, 3-Chloro-4-{4-[4-(2-chloro-4-cyano-6-methyl-phenoxy)-pyrimidin-2-ylamino]-piperidin-1-ylmethyl}-benzamide, 4-[5-Bromo-2-(1-pyrimidin-4-ylmethyl-piperidin-4-ylamino)-pyrimidin-4-yloxy]-3,5-dimethyl-benzonitrile, 4-{2-[1-(2-Chloro-4-methanesulfonyl-benzyl)-piperidin-4-ylamino]-5-trifluoromethyl-pyrimidin-4-yloxy}-3,5-dimethyl-benzonitrile, 4-[2-(8-Benzyl-8-aza-bicyclo [3.2.1]oct-3-ylamino)-5-bromo-pyrimidin-4-yloxy]-3,5-dimethyl-benzonitrile 4-{2-[1-(2-Chloro-4-methanesulfonyl-benzyl)-piperidin-4-ylamino]-5-fluoro-pyrimidin-4-yloxy}-3,5-dimethyl-benzonitrile, 4-{5-Chloro-2-[1-(2-chloro-4-methanesulfonyl-benzyl)-piperidin-4-ylamino]-pyrimidin-4-yloxy}-3,5-dimethyl-benzonitrile, 4-{4-[5-Bromo-4-(2-chloro-4-cyano-6-methyl-phenoxy)-pyrimidin-2-ylamino]-piperidin-1-ylmethyl}-3-chloro-benzamide, 4-{4-[5-Bromo-4-(2-chloro-4-cyano-6-methyl-phenoxy)-pyrimidin-2-ylamino]-piperidin-1-ylmethyl}-3-chloro-benzenesulfonamide, 4-{5-Bromo-2-[1-(1-phenyl-ethyl)-piperidin-4-ylamino]-pyrimidin-4-yloxy}-3,5-dimethyl-benzonitrile, 4-{5-Bromo-2-[1-(1-oxy-pyridin-4-ylmethyl)-piperidin-4-ylamino]-pyrimidin-4-yloxy}-3-chloro-5-methyl-benzonitrile, 4-{4-[4-Amino-5-bromo-644-cyano-2,6-dimethyl-phenoxy)-pyrimidin-2-ylamino]-piperidin-1-ylmethyl}-3-chloro-benzenesulfonamide, 4-{4-[4-Amino-5-bromo-6-(4-cyano-2,6-dimethyl-phenoxy)-pyrimidin-2-ylamino]-piperidin-1-ylmethyl}-3-chloro-benzamide,
4-{6-Amino-5-bromo-2-[1-(2-chloro-4-methanesulfonyl-benzyl)-piperidin-4-ylamino]-pyrimidin-4-yloxy}-3,5-dimethyl-benzonitrile,
4-{2-[1-(2-Chloro-4-methanesulfonyl-benzyl)-piperidin-4-ylamino]-pyrimidin-4-ylamino}-3,5-dimethyl-benzonitrile,
3-Chloro-4-{4-[4-(4-cyano-2,6-dimethyl-phenylamino)-pyrimidin-2-ylamino]-piperidin-1-ylmethyl}-benzenesulfonamide,
5-Bromo-$N^4$-(4-bromo-2,6-dimethyl-phenyl)-$N^2$-[1-(2-chloro-4-methanesulfonyl-benzyl)-piperidin-4-yl]-pyrimidine-2,4-diamine,
4-{4-[4-(4-Bromo-2,6-dimethyl-phenylamino)-pyrimidin-2-ylamino]-piperidin-1-ylmethyl}-3-chloro-benzenesulfonamide,
4-{5-Bromo-2-[1-(2-chloro-4-methanesulfonyl-benzyl)-piperidin-4-ylamino]-pyrimidin-4-ylamino}-3,5-dimethyl-benzonitrile,
3-Chloro-4-{4-[4-(4-cyano-2,6-dimethyl-phenylamine)-pyrimidin-2-ylamino]-piperidin-1-ylmethyl}-benzamide,
4-{4-[5-Bromo-4-(4-cyano-2,6-dimethyl-phenylamino)-pyrimidin-2-ylamino]-piperidin-1-ylmeth}-3-chloro-benzamide,
$N^4$-(4-Bromo-2,6-dimethyl-phenyl)-$N^2$-[1-(2-chloro-4-methanesulfonyl-benzyl)-piperidin-4-yl]-pyrimidine-2,4-diamine,
(E)-3-(4-{2-[1-(2-Chloro-4-methanesulfonyl-benzyl)-piperidin-4-ylamino]-pyrimidin-4-ylamino}-3,5-dimethyl-phenyl)-acrylonitrile,
3-Chloro-4-(4-{4-[4-((E)-2-cyano-vinyl)-2,6-dimethyl-phenylamino]-pyrimidin-2-ylamino}-piperidin-1-ylmethyl)-benzamide,
4-{5-Bromo-2-[1-(3-chloro-pyridin-4-ylmethyl)-piperidin-4-ylamino]-pyrimidin-4-ylamino}-3,5-dimethyl-benzonitrile,
4-{2-[(1R,5S)-8-(2-Chloro-4-methanesulfonyl-benzyl)-8-aza-bicyclo [3.2.1]oct-3-ylamino]-pyrimidin-4-ylamino}-3,5-dimethyl-benzonitrile,
3-Chloro-4-{4-[4-(4-cyano-2,6-dimethyl-phenylamino)-pyrimidin-2-ylamino]-piperidin-1-ylmethyl}-benzoic acid isopropyl ester,
3-Chloro-4-{4-[4-(4-cyano-2,6-dimethyl-phenylamino)-pyrimidin-2-ylamino]-piperidin-1-ylmethyl}-benzoic acid,
4-{5-Bromo-2-[1-(2-chloro-4-methanesulfonyl-benzyl)-piperidin-4-ylamino]-pyrimidin-4-ylamino}-3-chloro-5-methyl-benzonitrile,
(E)-3-(4-{5-Bromo-2-[1-(2-chloro-4-methanesulfonyl-benzyl)-piperidin-4-ylamino]-pyrimidin-4-ylamino}-3,5-dimethyl-phenyl)-acrylonitrile,
4-{4-[5-Bromo-4-(4-cyano-2,6-dimethyl-phenylamino)-pyrimidin-2-ylamino]-piperidin-1-ylmethyl}-3-chloro-benzoic acid,
3-Chloro-4-{4-[4-(4-cyano-2-methyl-phenylamino)-pyrimidin-2-ylamino]-piperidin-1-ylmethyl}-benzene sulfonamide,
4-{4-[5-Bromo-4-(4-cyano-2,6-dimethyl-phenylamino)-pyrimidin-2-ylamino]-piperidin-1-ylmethyl}-3-chloro-N-(2-dimethylamino-ethyl)-benzamide,
4-{4-[4-(4-Cyano-2,6-dimethyl-phenoxy)-pyrimidin-2-ylamino]-piperidin-1-yl}-benzenesulfonamide,
3-{4-[4-(4-Cyano-2,6-dimethyl-phenoxy)-pyrimidin-2-ylamino]-piperidin-1-yl}-benzenesulfonamide,
4-{6-Amino-2-[1-(3-cyano-phenyl)-piperidin-4-ylamino]-pyrimidin-4-yloxy}-3,5-dimethyl-benzonitrile,
4-{5-Bromo-2-[1-(3-cyano-phenyl)-piperidin-4-ylamino]-pyrimidin-4-yloxy}-3,5-dimethyl-benzonitrile,
4-{2-[1-(3-Cyano-phenyl)-piperidin-4-ylamino]-pyrimidin-4-yloxy}-3,5-dimethyl-benzonitrile,
3-{4-[4-(4-Cyano-2,6-dimethyl-phenoxy)-pyrimidin-2-ylamino]-piperidin-1-yl}-benzamide,
3-{4-[5-Bromo-4-(4-cyano-2,6-dimethyl-phenoxy)-pyrimidin-2-ylamino]-piperidin-1-yl}-benzamide,
4-{5-Bromo-2-[1-(3-methanesulfonyl-phenyl)-piperidin-4-ylamino]-pyrimidin-4-yloxy}-3,5-dimethyl-benzonitrile,
3-Chloro-4-{2-[1-(3-methanesulfonyl-phenyl)-piperidin-4-ylamino]-pyrimidin-4-yloxy}-5-methyl-benzonitrile,
4-{5-Bromo-2-[1-(3-methanesulfonyl-phenyl)-piperidin-4-ylamino]-pyrimidin-4-yloxy}-3-chloro-5-methyl-benzonitrile,
3-{4-[5-Bromo-4-(2-chloro-4-cyano-6-methyl-phenoxy)-pyrimidin-2-ylamino]-piperidin-1-yl}-benzamide,
3-{4-[4-(2-Chloro-4-cyano-6-methyl-phenoxy)-pyrimidin-2-ylamino]-piperidin-1-yl}-benzamide,
3-{4-[4-(4-Cyano-2,6-dimethyl-phenoxy)-5-fluoro-pyrimidin-2-ylamino]-piperidin-1-yl}-benzamide,
4-[5-Bromo-2-(1-pyrimidin-5-yl-piperidin-4-ylamino)-pyrimidin-4-ylamino]-3,5-dimethyl-benzonitrile,
3-{4-[5-Chloro-4-(4-cyano-2,6-dimethyl-phenoxy)-pyrimidin-2-ylamino]-piperidin-1-yl}-benzamide,
3-{4-[4-(4-Cyano-2,6-dimethyl-phenoxy)-5-trifluoromethyl-pyrimidin-2-ylamino]-piperidin-1-yl}-benzamide,
3,5-Dimethyl-4-{2-[1-(3-nitro-phenyl)-piperidin-4-ylamino]-pyrimidin-4-yloxy}-benzonitrile,
4-{5-Fluoro-2-[1-(3-methanesulfonyl-phenyl)-piperidin-4-ylamino]-pyrimidin-4-yloxy}-3,5-dimethyl-benzonitrile,
4-{5-Chloro-2-[1-(3-methanesulfonyl-phenyl)-piperidin-4-ylamino]-pyrimidin-4-yloxy}-3,5-dimethyl-benzonitrile,
4-{2-[1-(3-Methanesulfonyl-phenyl)-piperidin-4-ylamino]-5-trifluoromethyl-pyrimidin-4-yloxy}-3,5-dimethyl-benzonitrile,
4-{5-Bromo-2-[1-(3-chloro-5-cyano-phenyl)-piperidin-4-ylamino]-pyrimidin-4-yloxy}-3,5-dimethyl-benzonitrile,
4-{2-[1-(3-Chloro-5-cyano-phenyl)-piperidin-4-ylamino]-pyrimidin-4-yloxy}-3,5-dimethyl-benzonitrile,
3-{4-[5-Bromo-4-(4-cyano-2,6-dimethyl-phenoxy)-pyrimidin-2-ylamino]-piperidin-1-yl}-5-chloro-benzamide,
3-Chloro-5-{4-[4-(4-cyano-2,6-dimethyl-phenoxy)-pyrimidin-2-ylamino]-piperidin-1-yl}-benzamide,
2-{4-[5-Bromo-4-(4-cyano-2,6-dimethyl-phenoxy)-pyrimidin-2-ylamino]-piperidin-1-yl}-benzamide,
4-{4-[5-Bromo-4-(4-cyano-2,6-dimethyl-phenoxy)-pyrimidin-2-ylamino]-piperidin-1-yl}-benzamide,
3-Chloro-5-methyl-4-[2-(3,4,5,6-tetrahydro-2H-[1,3']bipyridinyl-4-ylamino)-pyrimidin-4-yloxy]-benzonitrile,
3-Chloro-5-methyl-4-[2-(1-pyrimidin-2-yl-piperidin-4-ylamino)-pyrimidin-4-yloxy]-benzonitrile,
3-Chloro-4-{2-[1-(3-cyanomethyl-phenyl)-piperidin-4-ylamino]-pyrimidin-4-yloxy}-5-methyl-benzonitrile, 4-{2-[1-(3-Amino-phenyl)-piperidin-4-ylamino]-5-bromo-pyrimidin-4-yloxy}-3-chloro-5-methyl-benzonitrile,
3-{4-[5-Bromo-4-(4-cyano-2,6-dimethyl-phenoxy)-pyrimidin-2-ylamino]-piperidin-1-yl}-N-methyl-benzamide,
3-{4-[5-Bromo-4-(4-cyano-2,6-dimethyl-phenoxy)-pyrimidin-2-ylamino]-piperidin-1-yl}-N-cyclopropyl-benzamide,
3-{4-[5-Bromo-4-(4-cyano-2,6-dimethyl-phenoxy)-pyrimidin-2-ylamino]-piperidin-1-yl}-N-(2-hydroxy-ethyl)-benzamide,
3-{4-[5-Bromo-4-(4-cyano-2,6-dimethyl-phenoxy)-pyrimidin-2-ylamino]-piperidin-1-yl}-N-(2-dimethylamino-ethyl)-benzamide,
2-(3-{4-[5-Bromo-4-(4-cyano-2,6-dimethyl-phenoxy)-pyrimidin-2-ylamino]-piperidin-1-yl}-phenyl)-acetamide,
4-{5-Bromo-2-[1-(3-hydroxymethyl-phenyl)-piperidin-4-ylamino]-pyrimidin-4-yloxy}-3,5-dimethyl-benzonitrile,
N-(3-{4-[5-Bromo-4-(4-cyano-2,6-dimethyl-phenoxy)-pyrimidin-2-ylamino]-piperidin-1-yl}-phenyl)-methanesulfonamide,
N-(3-{4-[5-Bromo-4-(4-cyano-2,6-dimethyl-phenoxy)-pyrimidin-2-ylamino]-piperidin-1-yl}-phenyl)-acetamide,
3-{4-[5-Bromo-4-(4-cyano-2-methoxy-6-methyl-phenoxy)-pyrimidin-2-ylamino]-piperidin-1-yl}-benzamide,
2-(3-{4-[5-Bromo-4-(4-cyano-2,6-dimethyl-phenoxy)-pyrimidin-2-ylamino]-piperidin-1-yl}-phenyl)-N-(2-dimethylamino-ethyl)-acetamide,
(3-{4-[5-Bromo-4-(2-chloro-4-cyano-6-methyl-phenoxy)-pyrimidin-2-ylamino]-piperidin-1-yl}-phenyl)-acetic acid,
2-(3-{4-[5-Bromo-4-(2-chloro-4-cyano-6-methyl-phenoxy)-pyrimidin-2-ylamino]-piperidin-1-yl}-phenyl)-N-(2-hydroxy-1-methyl-ethyl)-acetamide,
4-(5-Bromo-2-{1-[3-(1,2-dihydroxy-ethyl)-phenyl]-piperidin-4-ylamino}-pyrimidin-4-yloxy)-3,5-dimethyl-benzonitrile,
3-{4-[4-(4-Cyano-2,6-dimethyl-phenoxy)-5-methyl-pyrimidin-2-ylamino]-piperidin-1-yl}-benzamide,
2-(3-{4-[4-(2-Chloro-4-cyano-6-methyl-phenoxy)-5-methyl-pyrimidin-2-ylamino]-piperidin-1-yl}-phenyl)-acetamide,
3-{4-[5-Bromo-4-(4-cyano-2-fluoro-6-methyl-phenoxy)-pyrimidin-2-ylamino]-piperidin-1-yl}-benzamide,
N-[2-(3-{4-[5-Bromo-4-(4-cyano-2,6-dimethyl-phenoxy)-pyrimidin-2-ylamino]-piperidin-1-yl}-phenyl)-acetyl]-methanesulfonamide,
3-{4-[5-Bromo-4-(4-cyano-2,6-dimethyl-phenoxy)-pyrimidin-2-ylamino]-piperidin-1-yl}-benzenesulfonamide,
2-(3-{4-[5-Bromo-4-(4-cyano-2,6-dimethyl-phenoxy)-pyrimidin-2-ylamino]-piperidin-1-yl}-phenyl)-3-hydroxy-propionic acid,
2-(3-{4-[5-Bromo-4-(4-cyano-2,6-dimethyl-phenoxy)-pyrimidin-2-ylamino]-piperidin-1-yl}-phenyl)-propionic acid,
(3-{4-[5-Bromo-4-(4-cyano-2,6-dimethyl-phenoxy)-pyrimidin-2-ylamino]-piperidin-1-yl}-phenyl)-methoxy-acetic acid,
(3-{4-[5-Bromo-4-(4-cyano-2,6-dimethyl-phenoxy)-pyrimidin-2-ylamino]-piperidin-1-yl}-phenyl)-hydroxy-acetic acid,
(3-{4-[5-Bromo-4-(4-cyano-2,6-dimethyl-phenoxy)-pyrimidin-2-ylamino]-piperidin-1-yl}-phenyl)-difluoro-acetic acid,
(3-{4-[5-Chloro-4-(4-cyano-2,6-dimethyl-phenoxy)-pyrimidin-2-ylamino]-piperidin-1-yl}-phenyl)-methoxy-acetic acid,
(3-{4-[4-(4-Cyano-2,6-dimethyl-phenoxy)-5-methyl-pyrimidin-2-ylamino]-piperidin-1-yl}-phenyl)-methoxy-acetic acid,
4-[5-Bromo-4-(4-cyano-2,6-dimethyl-phenoxy)-pyrimidin-2-ylamino]-3,4,5,6-tetrahydro-2H-[1,2']bipyridinyl-4'-carboxylic acid amide,
4-[4-(4-Cyano-2,6-dimethyl-phenoxy)-pyrimidin-2-ylamino]-3,4,5,6-tetrahydro-2H-[1,2']bipyridinyl-6'-carboxylic acid amide,
4-{5-Bromo-2-[1-(3-cyano-phenyl)-piperidin-4-ylamino]-pyrimidin-4-ylamino}-dimethyl-benzonitrile,
3-{4-[4-(4-Cyano-2,6-dimethyl-phenylamino)-pyrimidin-2-ylamino]-piperidin-1-yl}-benzamide
3-{4-[5-Bromo-4-(4-cyano-2,6-dimethyl-phenylamino)-pyrimidin-2-ylamino]-piperidin-1-yl}-benzamide,
$N^4$-(4-Bromo-2,6-dimethyl-phenyl)-$N^2$-[1-(3-methanesulfonyl-phenyl)-piperidin-4-yl]-pyrimidine-2,4-diamine,
3-(4-{4-[4-((E)-2-Cyano-vinyl)-2,6-dimethyl-phenylamino]-pyrimidin-2-ylamino}-piperidin-1-yl)-benzamide,
3-(4-{4-[2-Chloro-4-((E)-2-cyano-vinyl)-6-methyl-phenylamino]-pyrimidin-2-ylamino}-piperidin-1-yl)-benzamide,
3-{4-[4-(2-Chloro-4-cyano-6-methyl-phenylamino)-pyrimidin-2-ylamino]-piperidin-1-yl}-benzamide,
4-[4-(4-Cyano-2,6-dimethyl-phenylamino)-pyrimidin-2-ylamino]-3,4,5,6-tetrahydro-2H-[1,3']bipyridinyl-5'-carboxylic acid methyl ester,
4-[4-(4-Cyano-2,6-dimethyl-phenylamino)-pyrimidin-2-ylamino]-3,4,5,6-tetrahydro-2H-[1,3']bipyridinyl-5'-carboxylic acid,
3,5-Dimethyl-4-[2-(3,4,5,6-tetrahydro-2H-[1,3']-bipyridinyl-4-ylamino)-pyrimidin-4-ylamino]-benzonitrile,
3,5-Dimethyl-4-[2-(1-pyrimidin-2-yl-piperidin-4-ylamino)-pyrimidin-4-ylamino]-benzonitrile,
4-[5-Bromo-2-(1-pyrimidin-2-yl-piperidin-4-ylamino)-pyrimidin-4-ylamino]-3,5-dimethyl-benzonitrile,
4-{5-Amino-2-[1-(3-amino-phenyl)-piperidin-4-ylamino]-pyrimidin-4-ylamino}-3,5-dimethyl-benzonitrile,
4-{2-[1-(3-Cyanomethyl-phenyl)-piperidin-4-ylamino]-pyrimidin-4-ylamino}-3,5-dimethyl-benzonitrile,
3-{4-[5-Bromo-4-(2-chloro-4-cyano-6-fluoro-phenylamino)-pyrimidin-2-ylamino]-piperidin-1-yl}-benzamide, and,
2-(3-{4-[5-Bromo-4-(4-cyano-2,6-dimethyl-phenylamino)-pyrimidin-2-ylamino]-piperidin-1-yl}-phenyl)-N,N-dimethyl-acetamide.

17. A method for treating an HIV-1 infection comprising administering to a host in need thereof a therapeutically effective amount of a compound according to claim 1.

18. A pharmaceutical composition comprising a therapeutically effective quantity of a compound according to claim 1 and at least one carrier, excipient or diluent.

* * * * *

UNITED STATES PATENT AND TRADEMARK OFFICE
CERTIFICATE OF CORRECTION

PATENT NO. : 7,998,969 B2  Page 1 of 1
APPLICATION NO. : 12/001947
DATED : August 16, 2011
INVENTOR(S) : Denis J. Kestesz et al.

It is certified that error appears in the above-identified patent and that said Letters Patent is hereby corrected as shown below:

Under Column 89, line 20, after "$R^{7a}$", please insert -- $R^{7b}$,--; under line 25, please delete "$CONR^7R^{7b}$", and insert -- $CONR^{7a}R^{7b}$--; under line 45, please delete "(l)", and insert --(f)--.

Under Column 92, under line 65, please delete "644" and insert --6-(4--.

Under Column 93, line 22, please delete "phenylamine", and insert --phenylamino--.

Signed and Sealed this
Thirteenth Day of December, 2011

David J. Kappos
*Director of the United States Patent and Trademark Office*

UNITED STATES PATENT AND TRADEMARK OFFICE
CERTIFICATE OF CORRECTION

PATENT NO. : 7,998,969 B2  
APPLICATION NO. : 12/001947  
DATED : August 16, 2011  
INVENTOR(S) : Denis J. Kertesz et al.

Page 1 of 1

It is certified that error appears in the above-identified patent and that said Letters Patent is hereby corrected as shown below:

Under Column 91, line 7, please insert -- 4- -- before "{4-[5-Bromo-4-(4-cyano-2,6-dimethyl-phenoxy)-pyrimi-".

Under Column 92, line 22, please delete "3-Chloro-4-{", and insert --3-Chloro-4-{2-[--.

Under Column 96, line 17, please insert --3,5-- before dimethyl-benzoni.

Signed and Sealed this  
Tenth Day of January, 2012

David J. Kappos  
*Director of the United States Patent and Trademark Office*